(12) United States Patent
Singhal

(10) Patent No.: US 6,231,893 B1
(45) Date of Patent: May 15, 2001

(54) IMMUNOSUPPRESSIVE AND TUMOUR-SUPPRESSIVE BONE MARROW FACTOR

(75) Inventor: Sharwan K. Singhal, London (CA)

(73) Assignee: London Health Services Centre, London (CA)

( * ) Notice: Subject to any disclaimer, the term of this patent is extended or adjusted under 35 U.S.C. 154(b) by 0 days.

(21) Appl. No.: 08/904,910

(22) Filed: Aug. 1, 1997

Related U.S. Application Data

(63) Continuation-in-part of application No. PCT/CA96/00077, filed on Feb. 5, 1996.

(30) Foreign Application Priority Data

Feb. 3, 1995 (GB) .................................................. 9502168

(51) Int. Cl.[7] .................................................. A61K 35/28
(52) U.S. Cl. .......................................................... 424/577
(58) Field of Search .......................... 530/351; 424/85.1, 424/577

(56) References Cited

FOREIGN PATENT DOCUMENTS

WO 91/19506    12/1991  (WO) .

OTHER PUBLICATIONS

Lau et al. Cellular Immunology 125:92–106, 1990.*
Montecucchi et al., Journal of Chromatography, 512:139–147, 1990.*
Lau et al, Cell. Immunol 125(1) 1990 92–106 (abstract only).*
Lenfant, PNAS 86:779, Feb. 1989.*
Merck Index, 1989 pp. 1356, 1357, 1360.*
Sporn et al., (1986) "Transforming Growth Factor–β: Biological Function and Chemical Structure," Science, 233:532–534.
Ahuja et al., (1993) "Effect of Transforming Growth Factor–β on Early and Late Activation Events in Human T Cells," J. Immunol., 150:3109–3118.

Hilton, (1992) "LIP: Lots of Interesting Functions," Trends. Biochem. Sci., 17:72–76.
Oppenheim et al. (1991) Properties of the Novel Proinflammatory Supergene "Intercrine" Cytokine Family[1], 9:617–648.
Broxmeyer et al., (1993) "Comparative Analysis of the Human Macrophage Inflammatory Protein Family of Cytokines (Chemokines) on Proliferation of Human Myeloid Progenitor Cells," 150:3448–3458.
Lenfant et al., (1989) "Inhibitor of Hematopoietic Pluripotent Stem Cell Proliferation: Proliferation: Purification and Determination of its Structure," Proc. Natl. Acad. Sci. 86:779–782.
Paukovits et al., (1982) "Isolation and Synthesis of a Hemoregulatory Peptide," Z. Naturforsch 37c:1297–1300.
Pelus & Strausser (1977) "Prostaglandins and the Immune Response," Life Science 20:903–914.
Rola–Pleszczynski (1985) "Immunoregulation by Leukotrienes and Other Lipoxygenase Metabolites," Immunol. Today 6:302–307.
Marcus (1984) "A Review of the Immunogenic and Immuno–Modulatory properties of Glycosphingolipids," 21:1083–1091.
Motari et al. (1986) "Immunoregulatory Activity of Human Bone Marrow," J. Immunol. 137:1133–1137.

* cited by examiner

Primary Examiner—Donna C. Wortman
Assistant Examiner—Brenda G. Brumback
(74) Attorney, Agent, or Firm—Klarquist Sparkman Campbell Leigh & Whinston, LLP

(57) ABSTRACT

A novel immunosuppressive factor derived from mammalian bone marrow is described, which inhibits T lymphocyte activation and TNF-α production by activated macrophages and also inhibits tumour and leukemia cell growth. The factor provides a novel therapeutic composition for treatment of tumours and of disorders associated with inflammatory reactions or T lymphocyte activation.

7 Claims, 42 Drawing Sheets

FIG. 19B
FIG. 19C
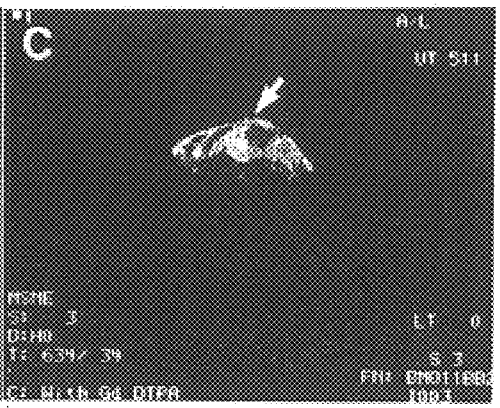
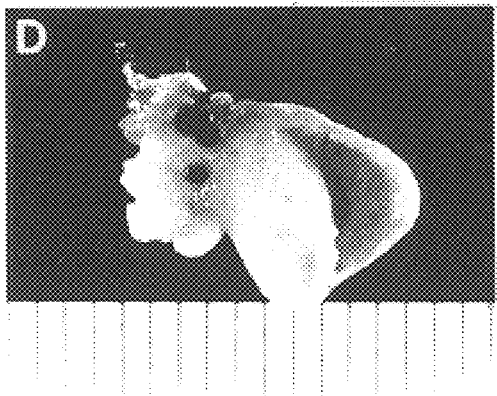
FIG. 19D
FIG. 19E

The Dose Dependent Suppression of IL-2 Production By Reptimed in MBP-Specific T Cell Hybridomas

| Culture Condition | Absorbance (450 nm) | IL-2 Conc. (pg/ml) | % Suppression |
|---|---|---|---|
| T Cells + APC | 0 | 0 | — |
| T Cells + APC + MBP | 0.364 | 160 | — |
| Reptimed (5 μ/cul) | 0.188 | 75 | 53 |
| Reptimed (2.5 μ/cul) | 0.304 | 130 | 19 |
| Reptimed (1.25 μ/cul) | 0.350 | 150 | 6 |
| Reptimed (0.625 μ/cul) | 0.376 | 170 | — |
| Reptimed (0.313 μ/cul) | 0.369 | 165 | — |

Note: T Cells: $2.0 \times 10^4$ cells/well
APC: $2.5 \times 10^5$ cells/well
MBP: 50 μg/ml

IMMUNOSUPPRESSIVE AND TUMOUR-SUPPRESSIVE BONE MARROW FACTOR

This is a continuation-in-part of PCT International Application No. PCT/CA96/00077, filed Feb. 5, 1996.

This invention relates to a new immunosuppressive and tumour-suppressive factor obtained from mammalian bone marrow. This factor appears to belong to a previously undescribed class of immunosuppressive molecules.

BACKGROUND OF THE INVENTION

A number of negative regulators of immune responses, cellular proliferation and hematopoiesis have been described. Protein or peptide negative regulators include transforming growth factor-beta (1,2), leukemia inhibitory factor (3), macrophage inflammatory protein-1-alpha (4,5), Ac-Ser-Asp-Lys-Pro (6), and pGlu-Glu-Asp-Cys-Lys (7). Lipid and lipid-related negative regulators include the prostaglandins (8), the leukotrienes (9), and the glycosphingolipids (10).

Preparations derived from bone marrow cells and showing immunosuppressive activity have also been described (11 and PCT application number WO91/19506).

The new factor described herein is distinguishable from all of these previously described factors both by chemical properties and by its biological activity, as will be more fully described below.

SUMMARY OF THE INVENTION

In accordance with the present invention, a novel immunosuppressive material of molecular weight less than 1000 Da, produced by mammalian bone marrow (BM) cells, has been identified and its biological properties described.

The new bone marrow factor described herein has been named Reptimed, in view of its source and immunosuppressive activity. The name Reptimed has been derived from the following Latin words: reprimere (to suppress); temperate (to modulate); immunitas (freedom from disease); and medulla (the bone marrow). "Reptimed" as used herein means a bone marrow-derived factor having the chemical, physical and biological properties described herein.

Reptimed has been purified using solid-phase extraction, gel filtration, gradient reverse-phase high performance liquid chromatography (RP-HPLC), and isocratic RP-HPLC, as described in Example 1 and has molecular weight less than 1000 daltons. Ionspray mass spectrometry indicates a molecular weight of about 625 daltons when protonated, as described in Example 3.

Reptimed is fully soluble in water and methanol but insoluble in hexans or chloroform.

An alternate method or purification has also been used, employing solid-phase extraction, gel filtration, anion exchange fast phase liquid chromatography (FPLC), $NH_2$-HPLC and reverse phase HPLC, as described in Example 3.

Reptimed can be distinguished from previously described, naturally occurring compounds with immunosuppressive or cancer-suppressive properties.

Reptimed is an effective immunosuppressor and has been shown to suppress T cell activation in response to a variety of stimulants.

Reptimed has also been demonstrated to have tumour-suppressing activity against mammalian tumours.

A further activity of Reptimed is its inhibition of the development of autoimmune responses.

Reptimed is highly conserved across species and can be obtained from bone marrow of the human, rat, mouse, cow, pig, and rabbit. Rat Reptimed has been most highly characterised to date but c18 cartridge-purified material has been isolated from bone marrow of all the above-noted species and in each case has ben shown to have the same biological activity in the WEHI-3 cell assay described in Example 1 (data not shown).

The biological activity of Reptimed is not species restricted. As seen in the examples herein, Reptimed obtained from rat bone marrow was active against human and mouse cell lines, indicating its cross-species effectiveness.

Reptimed has also been shown to interfere with early T cell signalling events involving activation of tyrosine kinases.

In accordance with one embodiment of the invention, a purified, water soluble immunosuppressive factor is provided characterised by a molecular weight less than 1000 daltons and movement as a single peak on reverse phase high performance liquid chromatography.

In accordance with a further embodiment of the invention, a factor is provided having the following biological activities:
(a) prevention or reduction of IL-2 production by activated T lymphocytes;
(b) prevention or reduction of TNF-α production by activated macrophages;
(c) prevention or reduction of proliferation of activated T lymphocytes; and
(d) inhibition of mixed lymphocyte reaction.

In accordance with another embodiment of the invention, a factor is provided having the following further biological activity:
(a) inhibition of tumour growth in a mammal.

In accordance with a further embodiment of the invention, a factor is provided having the following further biological activity:
(a) inhibition of leukemia cell proliferation.

In accordance with a further embodiment of the invention, a factor is provided having the following further biological activity:
(a) inhibition of a graft versus host reaction in a mammal.

In accordance with a further embodiment of the invention, a method is provided for inhibiting T lymphocyte activation in a mammal comprising administering to the mammal an effective amount of the immunosuppressive factor described herein.

In accordance with a further embodiment of the invention, a pharmaceutical composition is provided for inhibiting T lymphocyte activation in a mammal comprising an effective amount of the factor described herein and a pharmaceutically acceptable carrier.

In accordance with a further embodiment of the invention, a composition is provided comprising an effective amount of the factor described herein and a pharmaceutically acceptable carrier for use to inhibit T lymphocyte activation in a mammal.

In accordance with a further embodiment of the invention, a method is provided for treating or preventing a disorder associated with undesirable or excessive T lymphocyte activation, in a mammal, comprising administering to the mammal an effective amount of the factor described herein.

In accordance with a further embodiment of the invention, there is provided a pharmaceutical composition for treating or preventing a disorder associated with undesirable or excessive T lymphocyte activation comprising an effective amount of the factor described herein and a pharmaceutically acceptable carrier.

In accordance with a further embodiment of the invention, composition is provided comprising an effective amount of the factor described herein and a pharmaceutically acceptable carrier for use to treat or prevent a disorder associated with undesirable or excessive T lymphocyte activation.

In accordance with a further embodiment of the invention, a method is provided for inhibiting TNF-α production in a mammal comprising administering to the mammal an effective amount of the factor described herein.

In accordance with a further embodiment of the invention, a pharmaceutical composition is provided for inhibiting TNF-α production in a mammal comprising an effective amount of the factor described herein and a pharmaceutically acceptable carrier.

In accordance with a further embodiment of the invention, a composition is provided comprising an effective amount of the factor described herein and a pharmaceutically acceptable carrier for use to inhibit TNF-α production in a mammal.

In accordance with a further embodiment of the invention, a method is provided for treating or preventing a disorder associated with undesirable or excessive TNF-α production, in a mammal, comprising administering to the mammal an effective amount of the factor described herein.

In accordance with a further embodiment of the invention, a method is provided for inhibiting growth of a tumour in a mammal comprising administering to the mammal an effective amount of the factor described herein.

In accordance with a further embodiment of the invention, a pharmaceutical composition is provided for inhibiting growth of a tumour in a mammal comprising an effective amount of the factor described herein and a pharmaceutically acceptable carrier.

In accordance with a further embodiment of the invention, a composition is provided comprising an effective amount of the factor described herein and a pharmaceutically acceptable carrier for use to inhibit growth of a tumour in a mammal.

In accordance with a further embodiment of the invention, a method is provided for inhibiting growth of a leukemia in a mammal comprising administering to the mammal an effective amount of the factor described herein.

In accordance with a further embodiment of the invention, a pharmaceutical composition is provided for inhibiting growth of a leukemia in a mammal comprising an effective amount of the factor described herein and a pharmaceutically acceptable carrier.

In accordance with a further embodiment of the invention, a composition comprising an effective amount of the factor described herein and a pharmaceutically acceptable carrier for use to inhibit growth of a leukemia in a mammal.

In accordance with a further embodiment of the invention, a method is provided for preventing or treating, in a mammal, a disorder characterised by an abnormality in a signalling pathway, wherein the signalling pathway involves CD45 phosphatase activity, the method further comprising administering to the mammal a therapeutically effective amount of the factor described herein.

In accordance with a further embodiment of the invention, a method is provided for preparing a purified immunosuppressive factor comprising the steps of (a) culturing mammalian bone marrow cells to produce a factor-containing supernatant;

(b) subjecting the supernatant to solid phase extraction to produce a product;

(c) subjecting the product from step (b) to gel filtration to produce a product;

(d) subjecting the product from step (c) to anion exchange fast phase liquid chromatography to produce a product;

(e) subjecting the product from step (d) to amino-high performance liquid chromatography to produce a product; and (f) subjecting the product from step (e) to reverse phase high performance liquid chromatography to product purified immunosuppressive factor.

In accordance with a further embodiment of the invention, there is provided a purified immunosuppressive factor prepared in accordance with a method described herein.

In accordance with a further embodiment of the invention, a method is provided for inhibiting IL-2 production by activated T lymphocytes in a mammal comprising administering to the mammal an effective amount of the factor described herein.

In accordance with a further embodiment of the invention, a pharmaceutical composition is provided for inhibiting IL-2 production by activated T lymphocytes in a mammal comprising an effective amount of the factor described herein and a pharmaceutically acceptable carrier.

BRIEF DESCRIPTION OF THE DRAWINGS

Certain embodiments of the invention are described, reference being made to the accompanying drawings, wherein:

FIG. 16A shows IL-3-induced granulocyte-macrophage colonies.

FIGS. 19A–E show the effect of Reptimed on the growth of orthotopic MBT-2 tumours: 19A: MR image of a normal mouse in the transverse plane showing 4 contiguous 3mm slices covering the inflated bladder with a contrast agent relative to the external marker as indicated by the arrow; 19B: bladder of control 6 days after MBT-2 tumour implant (signal void caused by infusion of 1% Gadolinium-DPTA, indicated by arrow); 19C: bladder partially filled with MBT-2 tumour (arrow) 14 days after tumour implant; 19D: gross mount of bladder of Panel C; 19E: corresponding light microscopy illustrating the topography of tumour involvement.

FIG. 26 shows the suppression of IL-2 production by MBP-specific T cell hybridomas (stimulated with MBP) by Reptimed (as demonstrated with a murine IL-2 ELISA).

In FIGS. 31A to C, (–) is negative control (TPA 20 ng/ml), 0 is control culture without Reptimed, 5× and 1.25× are the Reptimed treated cultures.

DETAILED DESCRIPTION OF THE INVENTION

Figure 1:
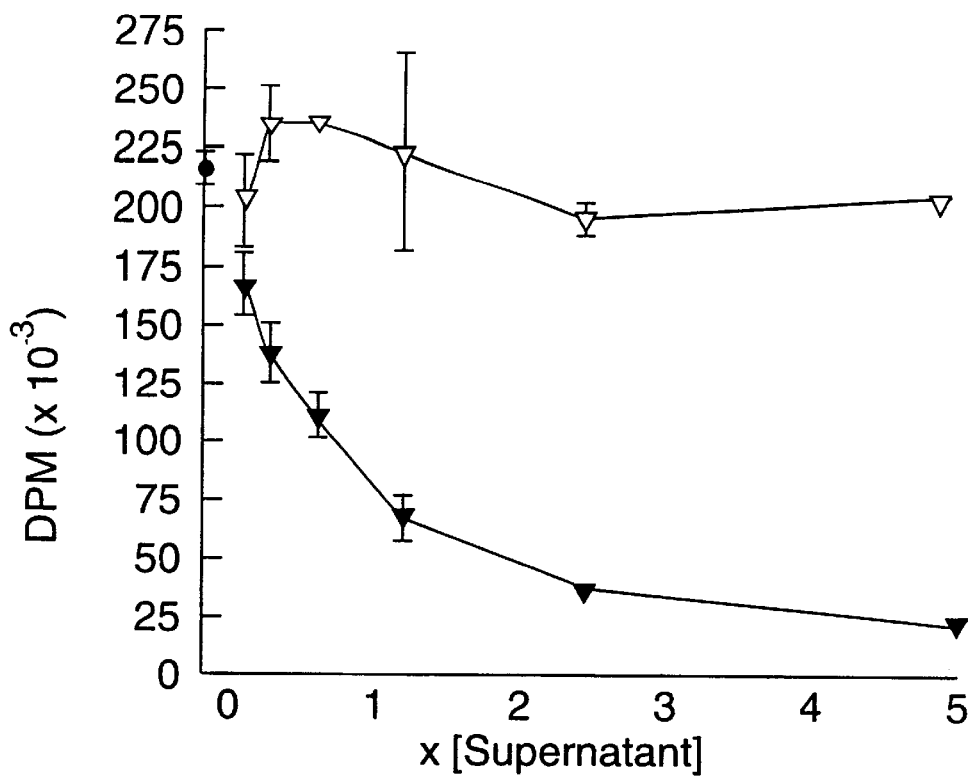
FIG. 1 shows suppression of WEHI-3 cell proliferation by $C_{18}$ cartridge-extracted Reptimed (▼) or $C_{18}$ cartridge-extracted RPMI medium as a control (▽). WEHI-3 cells alone were used as positive control (●). X axis refers to the fold increase in Reptimed concentration from the original bone marrow supernatants. Y axis is $^3$H-thymidine incorporation as a measure of cellular proliferation expressed as mean DPM×$10^{-3}$. Vertical error bars are standard deviation.

Differences Between Reptimed and Previously Described Naturally Occurring Immunosuppressive and Cancer-suppressive Compounds Proteins and Peptides Transforming growth factor-beta (TGFβ) is a 25 kDa protein with suppressive activity for growth of hepatocytes, epithelial cells, keratinocytes, and T lymphocytes (1,2). TGFβ inhibits the colony-forming assays CFU-GM, BFU-E and CFU-Meg but not CFU-E, CFU-G or CFU-M (12). In contrast, Reptimed suppresses both the CFU-GM and CFU-M assays (Example 5) and therefore has distinct biological activity.

Leukemia inhibitory factor (LIF) is a 20 kDa protein with multiple effects on various tissue types (3). LIF does not affect the proliferation of myeloid progenitor cells, but can induce differentiation in megakaryocytes and some myeloid progenitor cell lines (3). LIF blocks differentiation of embryonic stem cell lines in vitro (13). In contrast, Reptimed inhibits proliferation of several myeloid progenitor cell lines (Example 4).

Macrophage inflammatory protein-1-alpha (MIP-1α) (or SCI, for stem cell inhibitor) is an 8–10 kDa protein which is a member of the larger "chemokine" family of IL-8-related molecules (4,5). Besides its well-characterized chemotactic properties (5), MIP-1α inhibits IL-3 and erythropoietin-stimulated CFU-S and BFU-E colonies; and in combination with GM-CSF induces granulocyte-macrophage and macrophage colonies (5). MIP-1α may also act as a survival factor for pluripotent stem cells in vitro (14). In contrast to MIP-1α, Reptimed inhibits growth of IL-3-induced colonies (Example 5).

AcSDKP (sequence Ac-Ser-Asp-Lys-Pro) is a MW 487 peptide (6). AcSDKP inhibits endogenous CFU-S in mice, and therefore is an inhibitor of entry of stem cells into cell cycle (15). pEEDCK (sequence pGlu-Glu-Asp-Cys-Lys) is a MW 693 peptide purified from human leukocytes (7). pEEDCK inhibits exogenous CFU-S in mice and is therefore, like AcSDKP, an inhibitor of stem cell entry into cell cycle (16). pEEDCK suppresses GM-CFU colonies and proliferation of the HL-60 myeloid cell line (17,18). AcSDKP and pEEDCK are short peptides of known amino acid sequence and are therefore chemically distinct from Reptimed. Daughter ion analysis shows Reptimed not to have a peptide structure.

Lipid and Lipid-related Mediators

The prostaglandins are a family of 20-carbon unsaturated fatty acids, the best-understood of which is $PGE_2$ (8). Although the most important role of prostaglandins may be in stimulation of smooth muscle contraction and triggering of inflammatory reactions, Prostaglandins have also been described as being inhibitory for T and B cell responses (8). Prostaglandins also have a different cellular source than Reptimed, since prostaglandins are produced mostly by mature macrophages and neutrophils (8) while Reptimed is produced by immature, ER-MP-12$^+$, myeloid progenitor cells (Example 10).

The leukotrienes are 20-carbon unsaturated fatty acids closely related to prostaglandins, one of the best-characterized of which is $LTB_4$. All leukotrienes are classified as hydroxy-eicosatetraenoic acids, or HETEs (9). Like prostaglandins, leukotrienes are pro-inflammatory, modulating vascular permeability and mediating chemotaxis for phagocytes (9). Leukotrienes also inhibit responses of immune cells to mitogens or antigen, and may be direct inhibitors of interleukin-1 signalling (9).

The hydrophilic properties of Reptimed indicate that it is not a lipid, thus distinguishing it from the prostaglandins and the leukotrienes.

Like prostaglandins, leukotrienes are produced only in mature cells with lipooxygenase activity and would not be produced by immature cells, as is Reptimed (Example 10).

Glycosphingolipids (GSLs) are sphingolipids with long associated carbohydrate chains found mainly on the outer membrane of brain cells and erythrocytes (10). GSLs can in general be divided into the globo-, lacto-, and ganglio-families, each of which has characteristic carbohydrate sequences (10). The carbohydrate sequences can be long, and as a result, the molecular weights of typical GSLs are high (>1000). For example, the relatively simple ganglioside $GM_1$ is MW 1545. GSLs have been described as having suppressive effects for T and B cell function, either mitogen or antigen-driven (10). In addition, purified brain gangliosides can inhibit myeloid colony formation, such as the GM-CFU assay (19). The activities and chemistry of GSLs can be distinguished from Reptimed in several ways. Firstly, GSLs are of higher molecular weight than Reptimed. Secondly GSLs such as gangliosides are not water soluble, while Reptimed is fully water-soluble. Thirdly, Reptimed is produced in immature myeloid-series cells (Example 10) while glycospingolipids are found mainly on the surfaces of brain cells and erythrocytes. The mass spectrometry fragmentation of Reptimed indicates that it is not a sphingolipid.

The previously described bone marrow-derived immunosuppressive preparation, described as a lipid (11), was soluble in chloroform, insoluble in water, and had a molecular weight of over 1000. In contrast, Reptimed is fully soluble in water, insoluble in chloroform and has an apparent molecular weight of less than 1000 daltons.

Characterization of the mouse bone marrow cells which produce Reptimed has revealed them to be positive for a myeloid progenitor cell surface antigen, ER-MP12 (Example 10).

As described in Example 11, IL-3 has been shown to stimulate Reptimed production by BM cells. IL-3 is an early acting cytokine which is known to stimulate proliferation of early myeloid progenitors. The proliferation or activation of myeloid precursors by IL-3 may be responsible for increased production of Reptimed in vivo.

Immunosuppressive Activity of Reptimed

The mixed lymphocyte response (MLR) is an accepted in vitro model of T lymphocyte recognition of foreign MHC gene products. The proliferative response of a population of T lymphocytes against a stimulating allogeneic population of T lymphocytes is a relative measure of MHC disparity between the two cell populations. Therefore the MLR can be considered a predictive test for specific disease models whereby allogeneic T lymphocyte interactions initiate the disease process, such as acute graft versus host disease (GVHD), a common complication following allogeneic bone marrow transplantation.

As seen in Example 7, Reptimed can dramatically down regulate the murine MLR (C57BL/6 vs. Balb/c). A similar down regulation of rat and human MLR by rat Reptimed was also observed (data not shown). The dramatic suppression of MLR by Reptimed and its efficacy across species barriers indicates its importance as a new and effective therapeutic to suppress T lymphocyte activation in any situation in which such activation is undesirable or excessive, for example in conditions such as GVHD which involve T lymphocyte mediated inflammation.

When T lymphocytes are stimulated with specific antigen in the presence of Antigen Presenting Cells (APCs) or with antibodies that cross-link the T Cell Receptor (TCR), cellular proliferation ensues with production of various lymphokines. The hallmark lymphokine in T cell activation is IL-2, since IL-2 drives a T lymphocyte population into a state of proliferation.

Antigen (Ag)-specific T lymphocyte hybridomas effectively illustrate this concept of T lymphocyte activated production of IL-2. Example 13 demonstrates that Reptimed suppresses the proliferation of unstimulated myelin basic protein (MBP) specific T lymphocyte hybridomas (which are constantly proliferating), as well as suppresses the proliferation of these hybridomas when they are stimulated with MBP via syngeneic APCs. Furthermore, example 7 shows that Reptimed down regulates IL-2 production in the MBP stimulated (MBP-specific) T lymphocyte hybridomas. Reptimed's ability to suppress IL-2 production in activated T lymphocytes closely associates with its ability to suppress the MLR, and hence, enhances the potential for therapeutic intervention in T lymphocyte mediated disease states and undesirable inflammatory reactions involving T lymphocyte activation.

Reptimed has been shown to suppress the growth of myeloid-macrophage colonies, as well as proliferation of various cell lines of the myeloid lineage such as WEHI-3. When tested with primary peritoneal macrophages (murine Balb/c), Reptimed suppressed production of TNF-α when the macrophages were primed with interferon-gamma (IFN-γ), and subsequently activated with lipopolysaccharide (LPS). Example 9 illustrates Reptimed's ability to down regulate TNF-α in activated murine peritoneal macrophages by using the well established L-929 cytotoxicity bioassay. Example 9 also shows Reptimed's suppressive effect on transcription of TNF-α mRNA in activated macrophages by utilizing the reverse transcriptase-polymerase chain reaction (RT-PCR) technique.

Macrophages play an integral role in various disease states with autoimmune characteristics, such as acute graft-versus-host disease (GVHD), rheumatoid arthritis and multiple sclerosis, whereby they are triggered to release pathological amounts of cytostatic molecules such as TNF-α which causes severe surrounding tissue damage. Reptimed's ability to suppress TNF-α in activated macrophages indicates its therapeutic value in diseases with aberrant inflammatory reactions such as GVHD, rheumatoid arthritis and multiple sclerosis or in any disorder associated with undesired TNF-α production.

Anti-tumour Activity of Reptimed

Reptimed has been demonstrated (Example 4) to inhibit both human and murine leukemic cell lines.

Suppression of these cell lines by Reptimed is cytostatic in nature and not cytotoxic, as shown in the MTT assay of WEHI-3 cells. Since most leukemias originate as clonal proliferations of hematopoietic stem or progenitor cells, the regulatory role of Reptimed in regulation of leukemia cell proliferation is of great significance. It is also important to note that Reptimed prepared from rat bone marrow can suppress mouse as well as human cell lines, indicating its cross-species effectiveness. Although not all leukemic cell lines tested were equally sensitive to Reptimed, it is within the expertise of those skilled in the art to determine the efficacy of Reptimed in any particular patient.

The sensitivity of leukemias to Reptimed may depend on the stage of differentiation of the cell from which the malignant leukemia clone is derived. WEHI-3 (mouse) and HL-60 (human) cells, which are considered to be immature granulocyte/macrophage progenitors were highly sensitive to Reptimed whereas J774a (mouse) and U-937 (human) cells, which are considered to be relatively mature macrophage cell lines, were only moderately sensitive.

The low molecular weight and excellent water solubility of Reptimed further enhance its potential as an effective therapeutic agent for treatment of cancers, including solid tumours and leukemias, and of inflammatory and autoimmune diseases. Administration may be by oral, intravenous or subcutaneous routes.

Reptimed treatment has also been shown to give significant inhibition of growth of solid tumours (Example 6). The potency of Reptimed is indicated by the effectiveness of the dosage used, 0.1 μg per injection.

Inhibition of Autoimmune Response

NZB/W mice spontaneously develop an autoimmune lupus-like disease as they mature, with appearance of antibodies against DNA and RNA. The NZB/W mouse is an accepted animal model for lupus-like human autoimmune disease.

As seen in Example 18, treatment of these mice with Reptimed delayed the development of the autoimmune state. Anti-DNA responses were decreased in the spleens of Reptimed treatment mice. There was also a significant delay in the development of renal lesions in treated mice, compared with controls, as seen in Table 2.

Since Reptimed suppresses T cell receptor-mediated T cell activation, as well as IL-2 production, it provides a new and potent tool for therapeutic intervention in diseases associated with undesirable lymphoproliferation and T cell activation, including autoimmune diseases, some types of leukemias, and aberrant inflammatory situations.

The present invention provides a bone marrow-derived factor which suppresses all examined types of T lymphocyte activation without harming normal T lymphocytes. Reptimed is a new tool for therapeutic intervention in diseases associated with undesirable T lymphocyte activation, including autoimmune diseases such as rheumatoid arthritis, lupus, multiple sclerosis and type I diabetes, some types of leukemia and graft versus host reactions.

Suppression of In Vitro Rheumatoid Factor (RF) and Anti-ssDNA Antibodies in Cells of Normal and Rheumatoid Individuals by Reptimed The ability of Reptimed to suppress in vitro production of RF and anti-ssDNA antibodies by PBL from normal human subjects and patients with rheumatoid arthritis has been examined. Reptimed was able to suppress Epstein-Barr Virus (EBV) stimulated production of rheumatoid factor (IgM anti-IgG), and IgM anti-ssDNA antibodies by normal human cells. Furthermore, the spontaneous production of RF, and IgM anti-ssDNA antibodies by cells from rheumatoid individuals was also suppressed by Reptimed. In addition, EBV-stimulated rheumatoid cells showed significant suppression of RF and IgM anti-ssDNA antibody production in the presence of Reptimed.

Mechanism of Action of Reptimed

Reptimed has been shown to inhibit T cell proliferation induced by cell surface monoclonal antibodies: αCD3, αCD7 and αCD45 (Example 12). The inhibition was due to an arrest of cell cycle progression in the G0/G1 phase and not due to cell cytotoxicity. Reptimed has also been shown to inhibit T cells in an antigen specific manner.

Early T cell signalling events are mediated by phosphorylation of tyrosine residues on various protein substrates including both kinases and phosphatases.

The CD45 family of cell surface glycoproteins is expressed by many nucleated cells and is essential for cell activation. CD45 contains a cytoplasmic phosphatase domain. The src-related tyrosine kinases p56lck and p59fyn are the primary substrates for CD45 phosphatase activity. CD45 phosphatase removes C-terminal phosphate and leads to kinase activation. Reptimed inhibits the phosphatase activity of CD45 by up to 80% (Example 15).

Reptimed has also been shown to dephosphorylate a 55–60 kDa protein while hyperphosphorylating a 95–105 kDa protein.

Since CD45 is a crucial phosphatase involved in cell signalling and activation of early tyrosine kinases, these data suggest a specific molecular mechanism whereby Reptimed blocks cellular proliferation by inhibiting the phosphatase activity of CD45 and thereby interfering with phosphorylation of a 55–60 kDa protein required for cell signalling. These data also correlate with previous data that indicate that Reptimed affects TCR complex associated cell signalling since CD45 is linked to the TCR complex.

By arresting cells in the G0/G1 phase of the cell cycle, as seen in Example 14, Reptimed may be preventing the release of several critical cytokines that are released in the S and M phase of the cell cycle. These cytokines may be crucial for cell growth and thus this may partly explain the inhibition of T cell proliferation caused by Reptimed. Agents which elevate cyclic AMP (cAMP) and activate cAMP-dependent protein kinase inhibit lymphocyte function and growth. Increased cAMP inhibits lymphocyte Na—K—Cl cotransport. It was observed that Reptimed could inhibit Na—K—Cl cotransport and could increase levels of cAMP-dependent protein kinase, as described in Example 17. It should be understood that the usefulness of Reptimed as a therapeutic agent, as described herein, is not dependent on the precise mechanism of action, as postulated herein.

Reptimed is a novel, small, naturally produced, species and MHC unrestricted factor with cytostatic but not cytotoxic properties. The ability of Reptimed to down regulate production of rheumatoid factor, anti-DNA antibodies, and to suppress the production of TNF-α, makes it a suitable material for treatment of diseases involving inflammatory reactions.

For therapeutic use, Reptimed may be prepared by scaling up the method of preparation described herein, as will be understood by those skilled in the art. For example, a large scale bio-reactor system, as described by Glassey et al., (1988), may be used to grow mammalian bone marrow cells. Purification of Reptimed is carried out as described herein. For a small molecule such as Reptimed, a suitable sterile preparation for therapeutic use may be prepared by conventional methods, for example by filtration using a filter of suitable porosity.

The immunosuppressive properties of Reptimed also make it a useful tool for examining and disclosing intercellular and intracellular signalling mechanisms involved in regulation of the immune response. Reptimed also provides a tool to elucidate the signalling mechanisms involved in neoplastic events.

The examples are described for the purposes of illustration and are not intended to limit the scope of the invention.

EXAMPLE 1

Purification of Reptimed

Collection and culture of bone marrow cells: Wistar-Furth, Dark Agouti (DA) or Sprague-Dawley rats (Charles River, St. Constant, PQ) were used as a source of bone marrow cells. Femurs and Tibias were removed aseptically from rats sacrificed by $CO_2$ asphyxiation. Bone marrow was flushed from the bones using a 10 ml syringe and 18G needle (Terumo Medical Corp., Elkton Md.) into 10 ml plastic petri dishes (Nunc Plastics, Roskilde, Denmark) containing sterile HBSS (Gibco BRL, Burlington ON). Single cell suspensions were obtained by flushing BMC through progressively higher gauge needles, then washed once in HBSS before transfer to 20 ml glass vials. Erythrocytes and other debris were removed by layering 6 ml of Lympholyte-Rat (Cedarlane Laboratories, Hornby ON) under each BMC suspension and centrifuging at 1500 rpm for 30 minutes. Cells remaining at the interface were washed three times in HBSS and were plated in sterile 150×20 mm petri dishes (Nunc) at $1\times10^7$ cells/ml in serum-free HBSS supplemented with 100 U/ml penicillin G, 100 µg/ml streptomycin, 0.25 µg/ml fungizone, and 25 µg/ml gentamycin (Gibco). Supernatants of cultured BMC were collected at 24 hours, fresh HBSS was added, and supernatants were collected again at 48 hours. Pooled supernatants were centrifuged at 2000 rpm for 10 min to remove large debris, then filtered through a 0.8 µm Acrodisc syringe filter (Gelman Sciences, Rexdale ON) and stored at −70° C.

Solid Phase Extraction: $C_{18}$ cartridges (Mini-Spe-ed C18-14%, S.P.E. Limited, Concord ON) were prepared by washing with 10 ml of methanol followed by 10 ml 18 megaohm-cm deionized-distilled water. Up to 100 ml of supernatants of cultured BMC were passed through each cartridge before elution. After washing the cartridges with 5 ml of deionized-distilled water, material adsorbed to the $C_{18}$ cartridge was eluted with 3 ml methanol, evaporated under a stream of nitrogen, redissolved in a small volume of methanol, and stored at 4° C. Before testing the eluate for activity in vitro, the methanol was evaporated under nitrogen and replaced by culture medium.

$C_{18}$ cartridges were used to adsorb small hydrophobic molecules from the BMC culture supernatant, allowing the elimination of salts and other polar contaminants. FIG. 1 shows that potent suppressive activity was extracted from rat BMC supernatants compared to the control extract from culture buffer.

Gel Filtration: Bio-Gel P-2, nominal exclusion limit 1800 Da (Bio-Rad, Richmond Calif.) was washed and pre-swelled in 20 mM Tris-HCl buffer, pH 7.2 (Sigma) and thoroughly degassed by gentle swirling under vacuum. Bio-Gel P-2 was packed into a 1.5×54 cm glass column and equilibrated with 3 column volumes of the same buffer. Reptimed samples extracted by $C_{18}$ cartridge were evaporated to dryness under a stream of nitrogen and dissolved in 0.5 ml of 20 mM Tris buffer, pH 7.2. Samples were carefully applied to the column and the flow rate was adjusted to 7.8–8.2 ml/hr. 3.0 ml fractions were collected from the column using a model 2112 Redirac fraction collector (LKB/Wallac) and the absorbance of these fractions was measured at 215 nm. Material in each fraction was recovered using $C_{18}$ cartridges, as described above. The biological activity was tested using WEHI-3 cells as described above.

Figure 2:
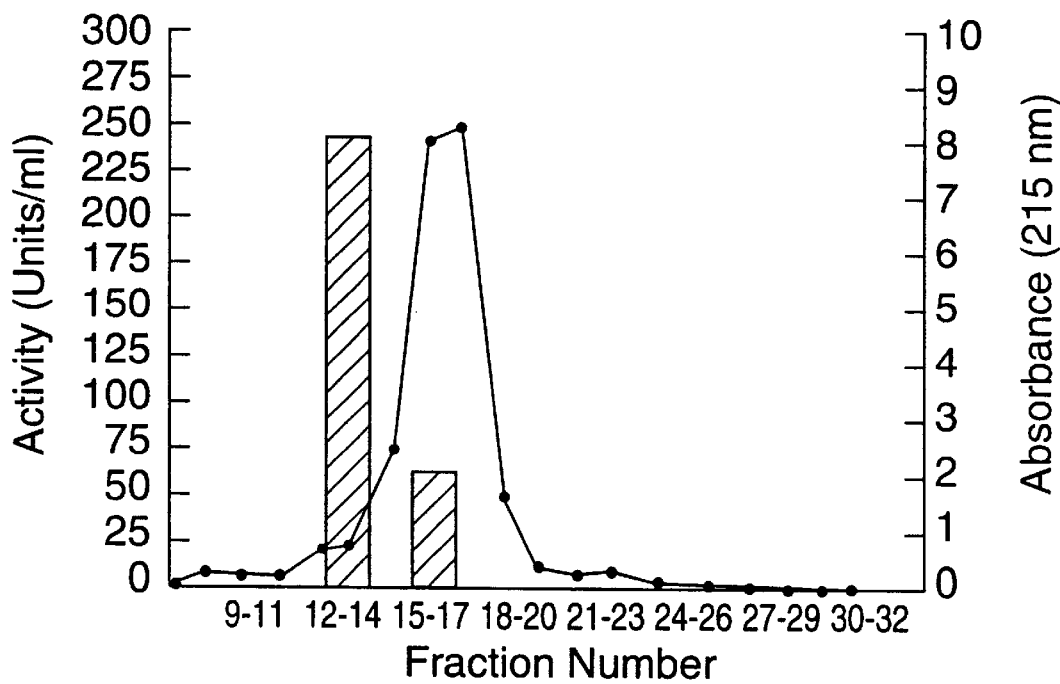
FIG. 2 shows fractionation of $C_{18}$ cartridge-purified Reptimed by Bio-gel P-2 gel filtration. Absorbance of each fraction at 215 nm is shown on the right vertical axis (●) while biological activity is shown on the left vertical axis (hatched bars).
Figure 3:
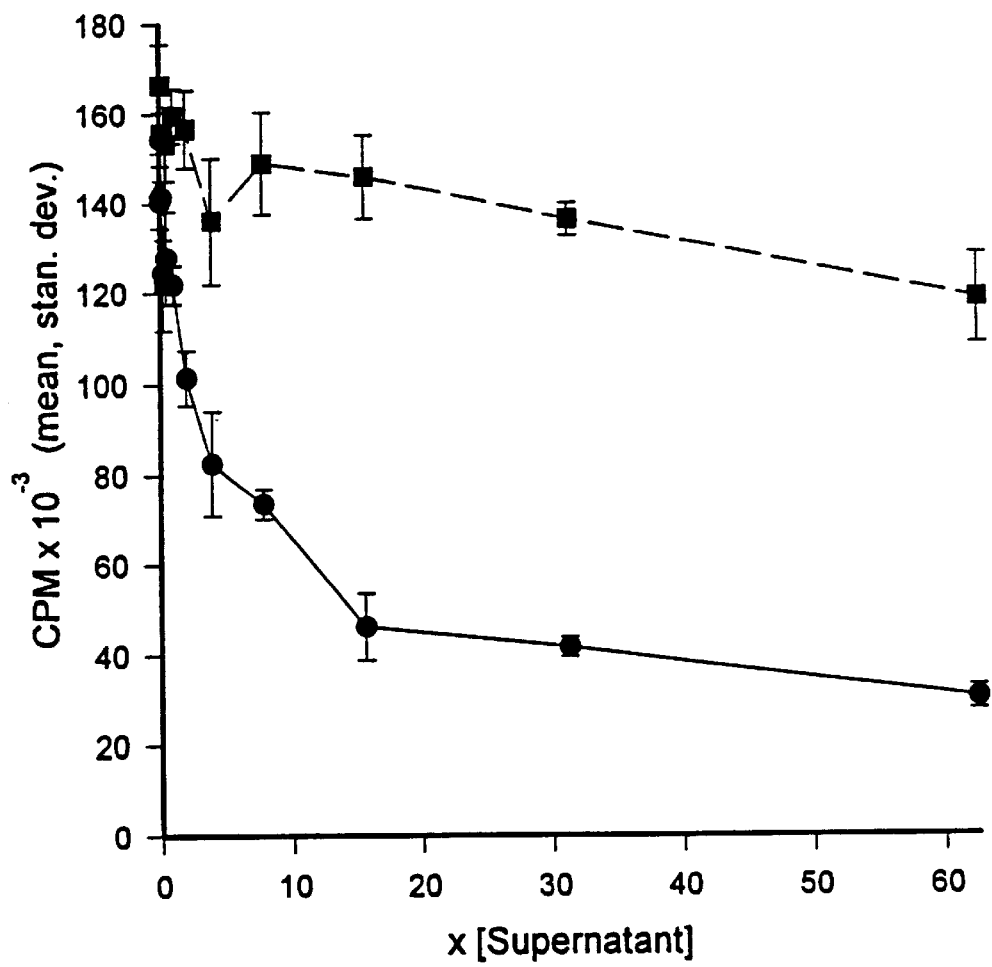
FIG. 3 shows suppression of WEHI-3 cell proliferation by $C_{18}$ cartridge and P-2 gel filtration-purified Reptimed. The Y axis indicates mean $^3$H-thymidine incorporation in CPM× $10^{-3}$ of triplicate WEHI-3 cultures treated with $C_{18}$ cartridge and P-2 gel filtration-purified Reptimed (●) or with $C_{18}$ cartridge and P-2 gel filtration-purified control buffer (■). Vertical error bars represent standard deviation. The X axis refers to the fold increase in Reptimed concentration from the original bone marrow supernatants.
Figure 4:
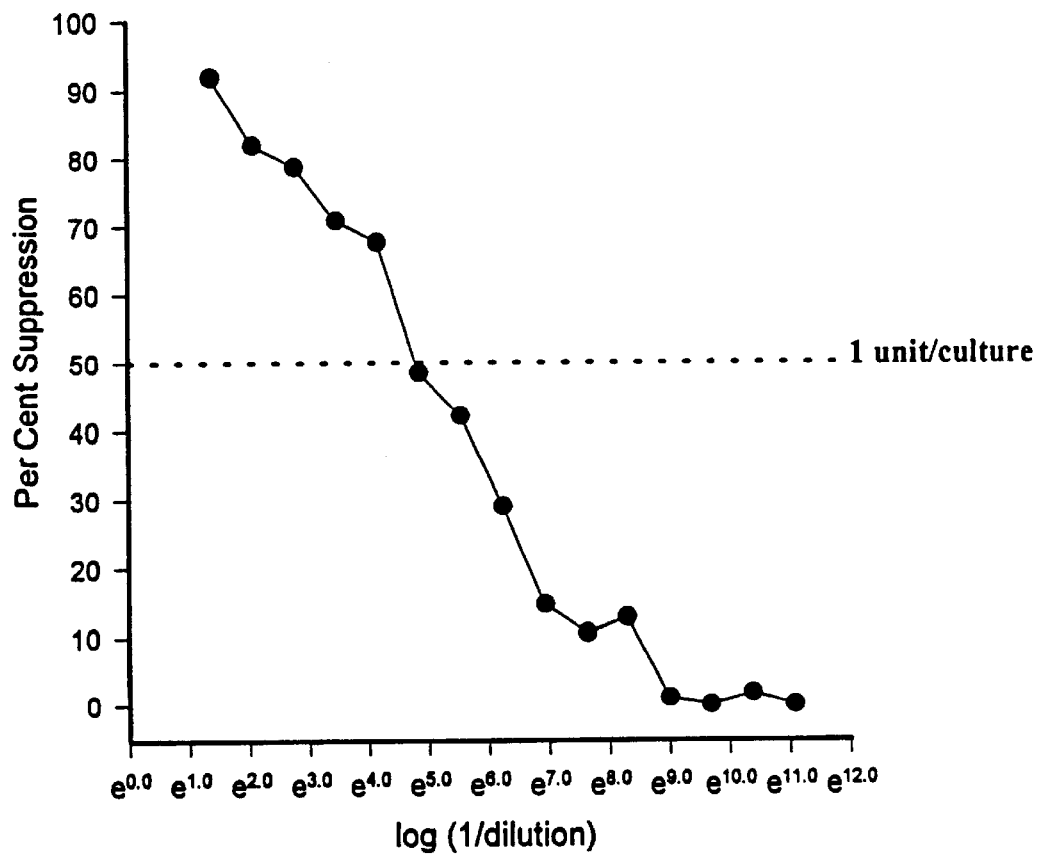
FIG. 4 shows the standard dilution curve of $C_{18}$ cartridge and P-2 gel filtration-purified Reptimed used to calculate units of activity. The Y axis shows per cent suppression of $^3$H-thymidine incorporation in WEHI-3 cells. The X axis shows the natural log of 1/dilution from the stock concentration. One unit of activity is defined as the amount of Reptimed which produces 50% inhibition of $^3$H-thymidine incorporation in the WEHI-3 cell line.

Gel filtration was used to fractionate $C_{18}$ purified material. FIG. 2 shows the result of one representative experiment. Most immunosuppressive activity eluted in fractions 12–14 while the major peak of absorbance eluted in fractions 15–20. Fractions 12–14 eluted much after the void volume. The suppressive activity was not due to thymidine, since thymidine alone elutes in fractions 21–23. The suppressive activity had no absorbance at 267 nm where thymidine absorbs most strongly. Unlike thymidine, the suppressive activity was not destroyed by hydrazine and piperidine. P-2 gel filtration-purified Reptimed is significantly more suppressive than P-2 gel filtration-purified control extracts of buffer alone (FIG. 3). Using the amount of absorbance at 215 nm as an estimate of the amount of material in the biologically active fractions compared to the non-active fractions, the active fractions were enriched in specific activity 10-fold over $C_{18}$ cartridge purified material. Reptimed purified by $C_{=1=3}$ cartridge and P-2 gel filtration was also used to establish a standard curve for measurement of biological activity in various batches. The Reptimed standard curve is shown in FIG. 4.

Reverse-Phase HPLC: Liquid chromatography was performed on a Waters Associates HPLC system consisting of a model 720 system controller, model 730 data module, two M-45 pumps, WISP 710B injector and model 481 LC spectrophotometer. Active fractions purified by gel filtration were further fractionated using a 300×3.9 mm µBondapak $C_{18}$ column (Waters/Millipore, Mississauga ON). Isocratic or gradient solvent systems consisted of redistilled acetonitrile, HPLC-grade water, and 0.1% trifluoroacetic acid (Fisher). The flow rate was 1 ml/min, and absorbance was monitored at 215 nm. Fractions were collected using a model 2211 Superrac fraction collector (LKB/Wallac) and lyophilized using a freeze-dryer (Freezemobile-12, Virtis Co. Inc., Gardiner N.Y.).

Figure 5:
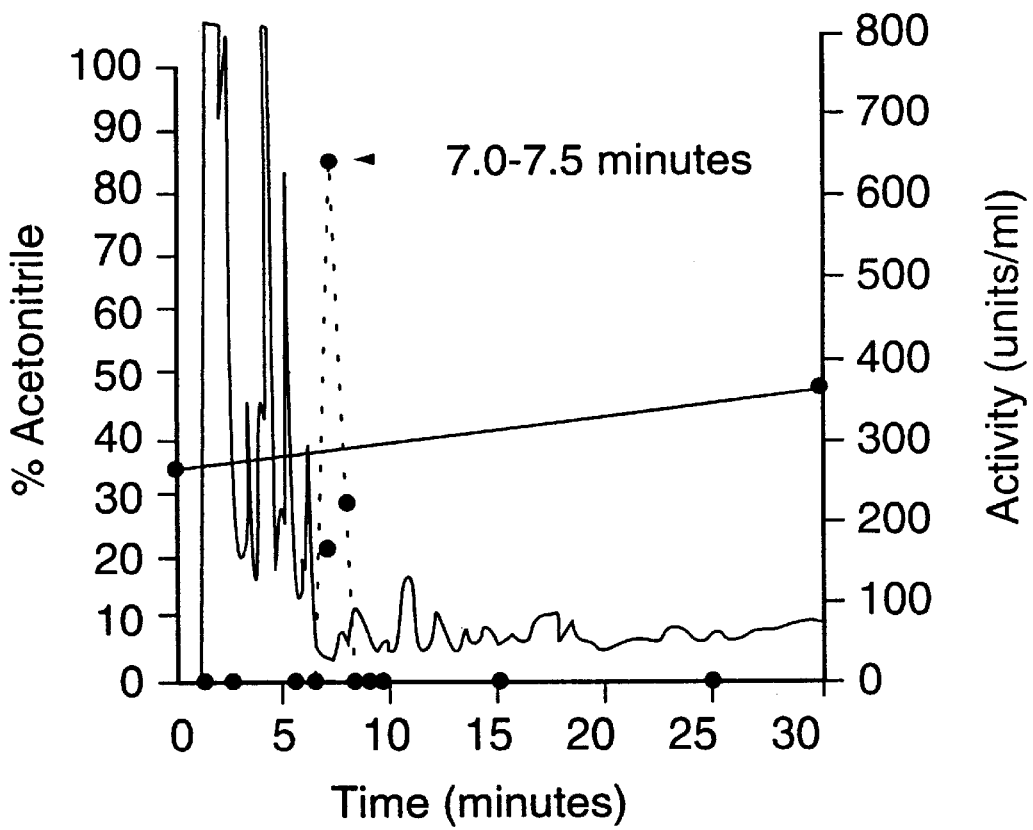
FIG. 5 shows fractionation of $C_{18}$ cartridge and P-2 gel filtration-purified Reptimed by gradient RP-HPLC. The left vertical axis and solid straight line represent the change in per cent acetonitrile over time. Time in minutes is shown on the X axis. The right vertical axis indicates biological activity, in units/ml, of the various fractions collected (●). The data represented by both left and right vertical axes are superimposed over the HPLC trace, which is measured as relative UV absorbance at 215 nm over time.

Suppressive material purified by $C_{18}$ cartridges and P-2 gel filtration as described above was first subjected to gradient RP-HPLC, using a gradient of 35–50% acetonitrile into water over 30 minutes. Both solvents also contained 0.1% trifluoroacetic acid (TFA). As shown in FIG. 5, suppressive activity eluted in the 7.0–7.5 minute fraction.

Figure 6:
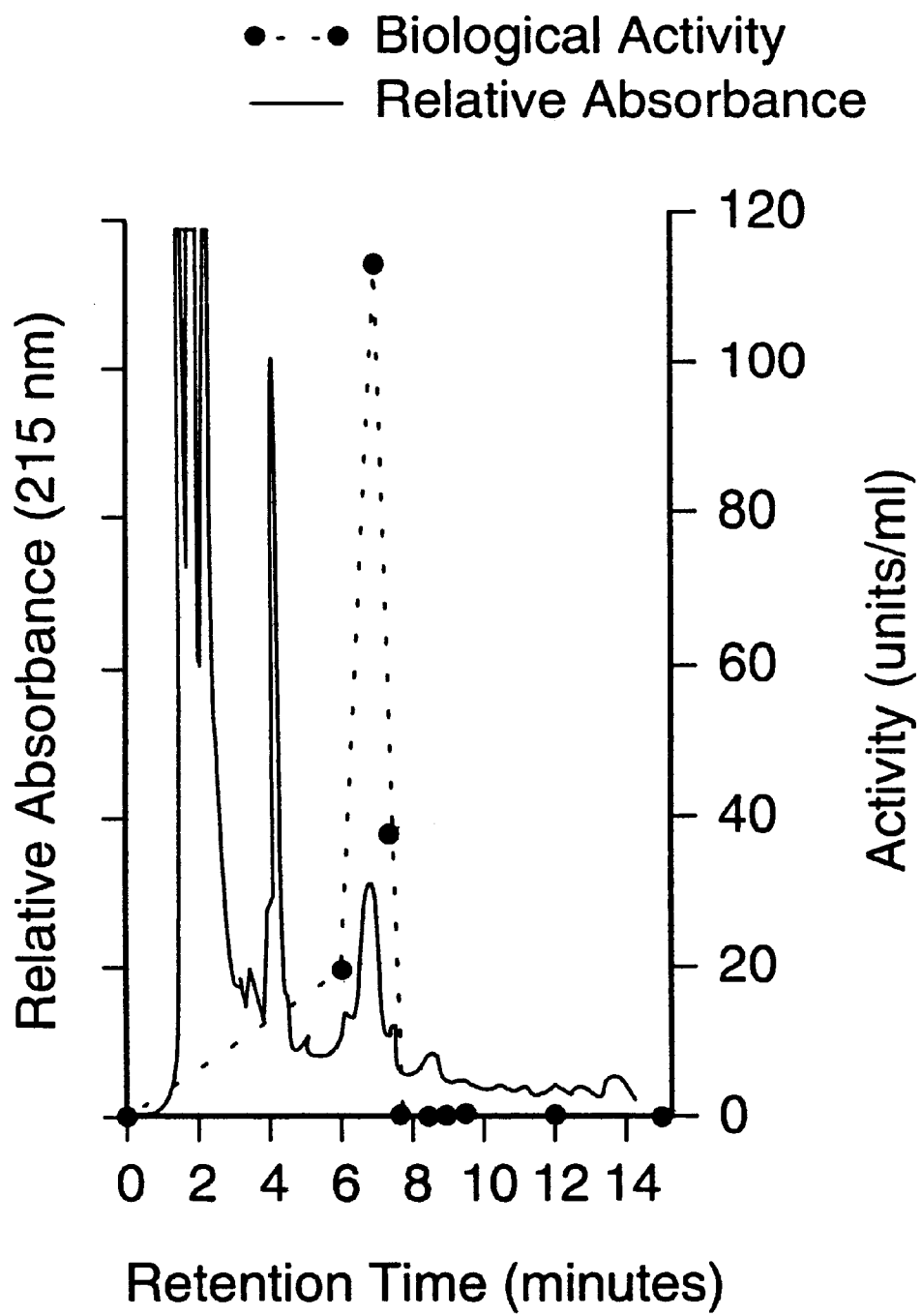
FIG. 6 shows fractionation of $C_{18}$ cartridge, P-2 gel filtration, and gradient RP-HPLC-purified Reptimed by isocratic RP-HPLC. The left vertical axis indicates relative UV absorbance at 215 nm of all material eluting from the HPLC column (solid line, no units). The X axis indicates retention time in minutes. The right vertical axis indicates biological activity, in units/ml, of the various fractions collected (●).
Figure 7:
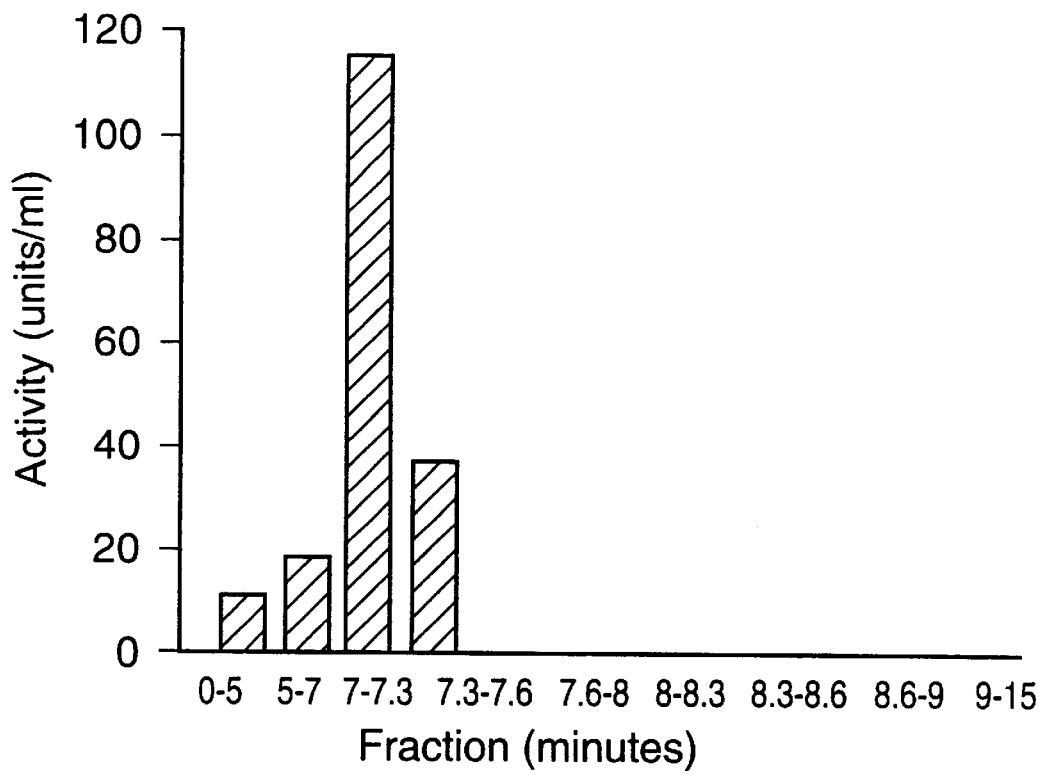
FIG. 7 shows the biological activity information from FIG. 6. The Y axis indicates biological activity in units/ml (hatched bars). The X axis indicates retention time of each collected fraction in minutes.

Suppressive material from the 7.0–7.5 minute fraction was pooled and further purified by isocratic RP-HPLC, using a solvent system consisting of 35% acetonitrile and 0.1% TFA. As shown in FIG. 6, suppressive activity eluted as a single peak of UV absorbance at 215 nm. The biological activity of the various HPLC fraction collected is shown in FIG. 7. Using the amount of UV absorbance of the active fractions compared to non-active fractions, there was a 160-fold increase in specific activity over the two RP-HPLC steps.

Material purified by solid phase extraction on a $C_{18}$ cartridge followed by gel filtration, as described above, was subjected to an alternate purification method comprising anion exchange FPLC, amino ($NH_2$) HPLC and reverse phase HPLC steps, as described below. Biologically active fractions purified by $C_{18}$ cartridge and gel filtration were concentrated, and redissolved in Tris-HCl buffer, pH 8.4, for further purification: Anion Ezchange PPLC: The Pharmacia FPLC system consisted of an LCC-500 CI liquid chromatographic controller with a 80286 PC running "TFPLC Manager", 2 P-500 pumps, an MV-7 injection motor valve, UV-M absorbance monitor, and Frac-100 fraction collector. Samples were injected and loaded on a Fast-Q Sepharose FPLC column running Tris-HCl buffer pH 8.4. Material was eluted from the column with a 0–0.5 M NaCl gradient; peaks were monitored at 280 nm. Material in each fraction was recovered using $C_{18}$ cartridges, as described above. The biological activity was tested using WEHI-3 cells as described.

Figure 9:
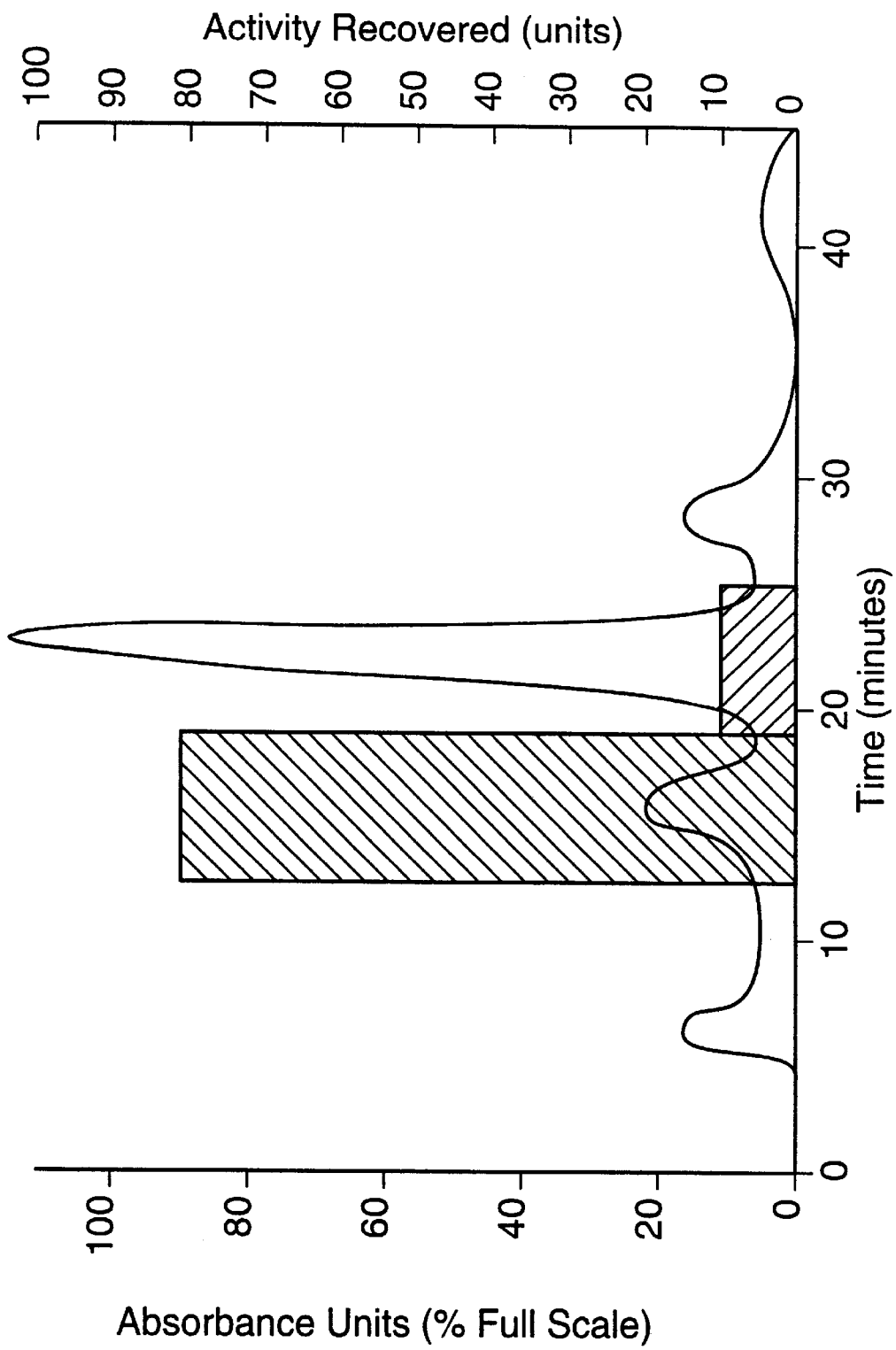
FIG. 9 shows fractionation of $C_{18}$ cartridge and P-2 gel filtration purified Reptimed by anion exchange FPLC. The left vertical axis and solid line represent the UV absorbance units at 280 nm expressed as per cent full scale. Time in minutes is shown on the X axis. The right vertical axis and shaded bars indicated biological activity, in units/ml, of the various fractions collected.

FIG. 9 shows the result of one representative experiment. Biological activity eluted mostly in fractions 13–19 while most UV absorbance at 280 nm was in fractions 20–25.

High Performance Liquid Chromatography (HPLC): Liquid chromatography was performed on a Waters Associates HPLC system consisting of a model 720 system controller, model 730 data module, two M-45 pumps, U6K injector and model 481 LC spectrophotometer.

Amino ($NH_2$) HPLC: Biologically active fractions purified by $C_{18}$ cartridge extraction, gel filtration and anion exchange FPLC were fractionated using a Waters Carbohydrate Analysis column, 3.9 mm×30 cm. The mobile phase consisted of 80% redistilled acetonitrile in HPLC-grade water. The flow rate was 1 ml/min and absorbance was measured at 215 nm. Fractions were collected using an IKB/Wallac model 2211 Superrac fraction collector. The volume of each fraction was significantly reduced by evaporation under a stream of nitrogen before recovering the activity on $C_{18}$ cartridges, as described above, and tested for biological activity.

Figure 10:
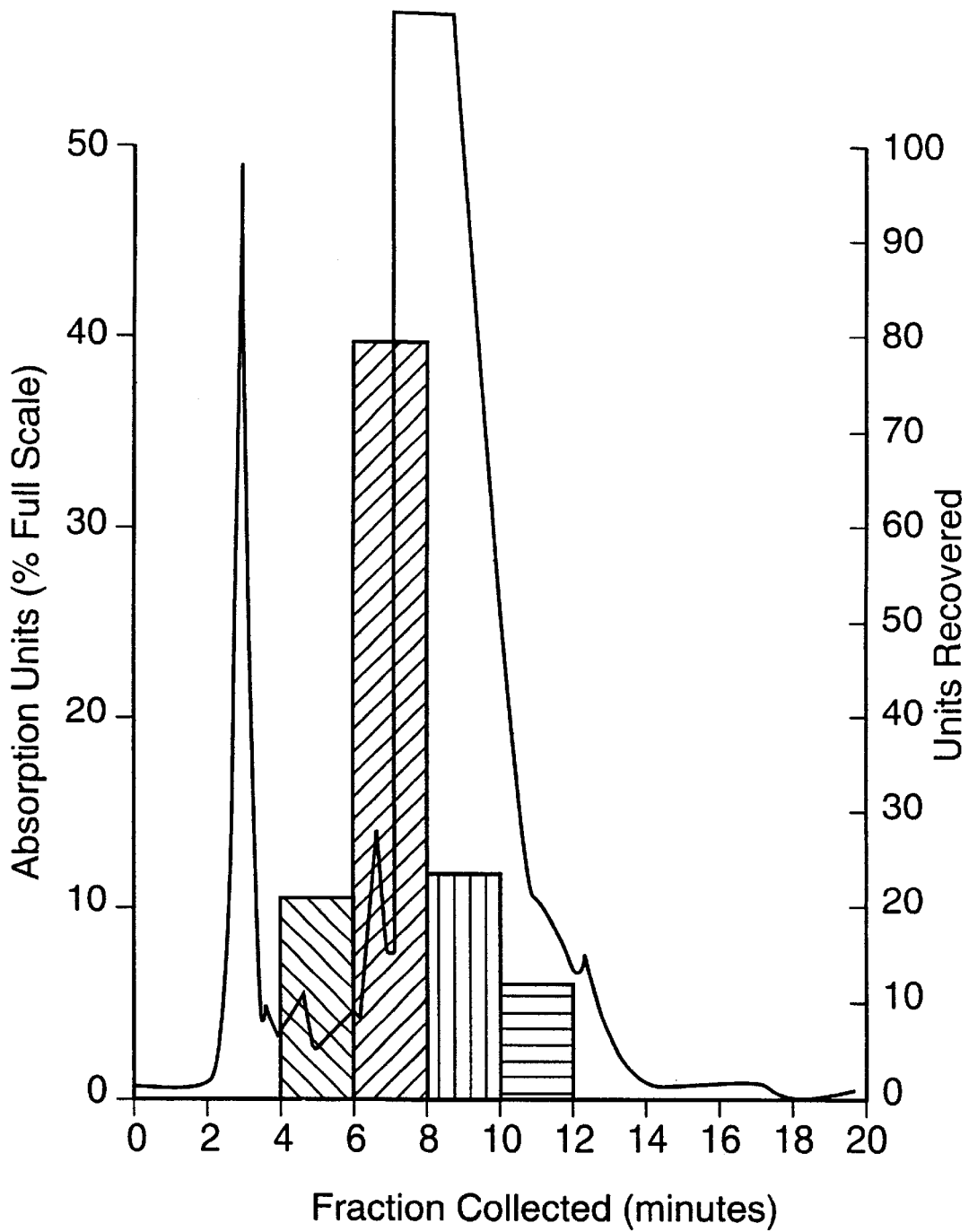
FIG. 10 shows fractionation of $C_{18}$ cartridge, P-2 gel filtration and anion exchange purified Reptimed by $NH_2$-HPLC. The left vertical axis and solid line represent the UV absorbance units at 215 nm expressed as per cent full scale. Time in minutes is shown on the X axis. The right vertical axis and shaded bars indicate biological activity, in units/ml, of the various fractions collected.

FIG. 10 shows the results of one representative experiment. Biological activity eluted primarily in fractions 6–8 while most UV absorbance at 215 nm eluted in fractions 7–12.

Reverse-Phase HPLC: Biologically active fractions purified by gel filtration, anion exchange and Amino ($NH_2$) HPLC were fractionated using a Brownlee Aquapore RP-300 C8 cartridge column, 2.1 mm×22 cm. The mobile phase consisted of 25% redistilled acetonitrile and 0.1% trifluoroacetic acid in HPLC-grade water. The flow rate was 0.2 ml/min and absorbance was measured at 215 nm. Fractions were collected using an LKB/Wallac model 2211 Superrac fraction collector. Collected fractions were dried directly under a stream of nitrogen and redissolved in methanol before testing for biological activity.

Figure 11:
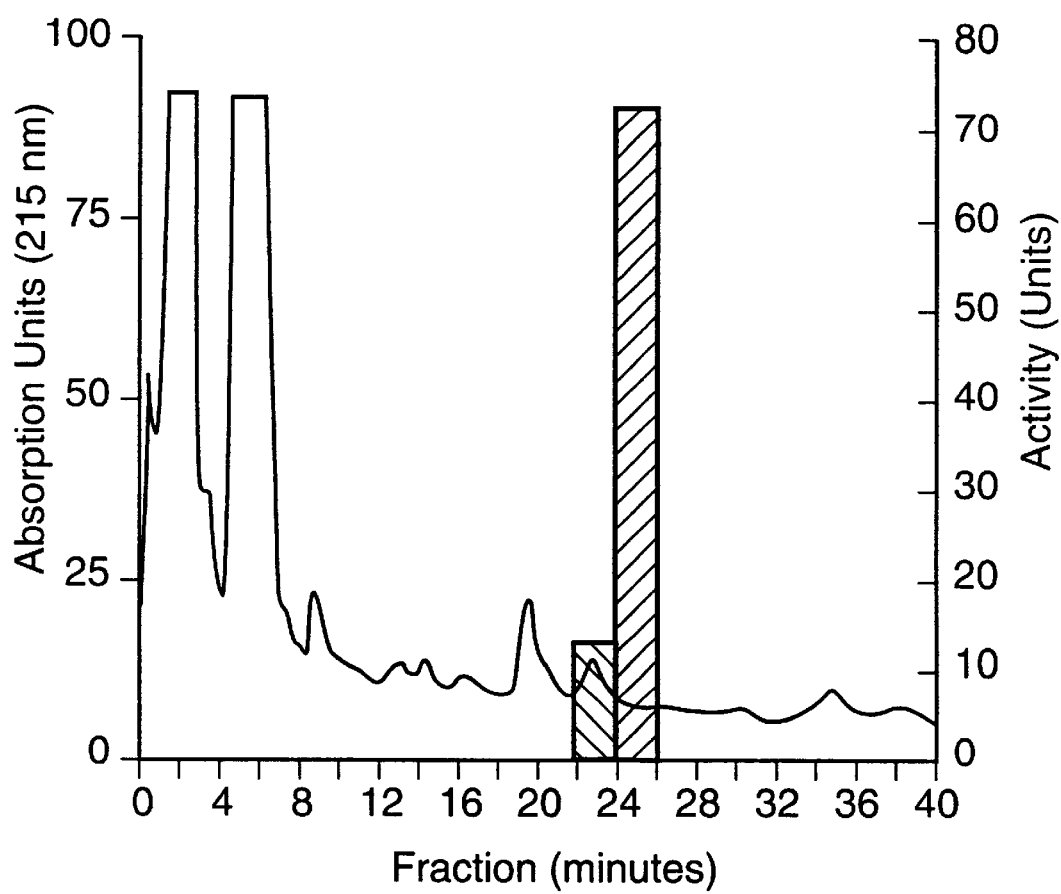
FIG. 11 shows fractionation of $C_{18}$ cartridge, P-2 gel filtration, anion exchange, and $NH_2$-HPLC by $C_8$ RP-HPLC. The left vertical axis and solid line represent the UV absorbance units at 215 nm expressed as per cent full scale. Time in minutes is shown on the X axis. The right vertical axis and shaded bars indicated biological activity, in units/ml, of the various fractions collected.

The results of one representative experiment are shown in FIG. 11. Biological activity eluted primarily in fractions 24 to 26 while UV absorbance at 215 nm eluted primarily in fractions 0–10.

Purification of Reptimed was measured by comparing the amount of UV absorption of biologically active fractions compared to biologically inactive fractions. Using this method of comparison, the relative purity of Reptimed was increased by $1.38\times10^5$-fold over 5 steps of purification. The relative enrichment in biological activity over 5 steps of purification was 920-fold. Purification is shown in Table 3.

Concentrations of Reptimed

The concentration of Reptimed in cultured BMC supernatants was generally too low for direct measurement of its biological activity. The studies of biological activity described in the following examples were carried out with concentrated supernatant or with Reptimed purified to various degrees, as indicated in each example.

"x[Supernatant]" or "Times Supernatant Concentration", as used herein, refer to the fold-concentration of the Reptimed preparation referred to, relative to the original BMC culture supernatant concentration. For example, if purified or partially purified Reptimed was obtained in a volume ⅕ of that of the original BMC supernatant, the concentration of the purified preparation is referred to as "5×supernatant".

Standard Biological Assay: The measure of biological activity used to monitor purification of the invention was inhibition of tritiated thymidine incorporation in the mouse myelomonocytic cell line, WEHI-3. WEHI-3 murine myelomonocytic leukemia cells (ATCC, Rockville Md.) were maintained by regular passage in complete RPM1 medium in 25 $cm^2$ tissue culture flasks (Nunc Plastics, Roskilde, Denmark). Complete RPM1 medium consisted of RPMI-1640 supplemented with 10% Fetal Bovine Serum, 2 mM L-Glutamine, 100 U/ml penicillin G, 100 μg/ml streptomycin, and 25 μg/ml gentamycin (Gibco-BRL, Burlington, Ont.). WEHI-3 cells were in early log phase growth at the start of each experiment. $2\times10^4$ WEHI-3 cells were cultured per well in 96-well flat bottom culture plates (Nunc) along with various dilutions of material to be tested, dilutions being made in complete RPM1 medium. The cultures were incubated at 37° C. in 5% $CO_2$ for a total of 48 hours including a four-hour pulse with 0.5 μCi/well $^3$H-thymidine (ICN, Mississauga ON). Cultures were harvested onto glass fibre filter paper (90×120 mm printed filtermat "A", Wallac, Turku Finland) on an automatic 96-well cell harvester (Tomtec 96, Orange Conn., USA) and counted on a Microbeta 1450 liquid scintillation counter (LKB/Wallac, Turku Finland) using an IBM PS/2 model 30 286 computer.

Unit of Activity: One unit of activity is defined as the amount of Reptimed which produces 50% inhibition of $^3$H-thymidine incorporation in a single WEHI-3 cell culture ($2\times10^4$ WEHI-3 cells per 200 μl well). Based on assays of Reptimed purified by $C_{18}$ cartridge, it was estimated that BMC supernatants contained an average level of about one unit of activity/100 μl supernatant.

Statistics: Unless otherwise indicated, all results shown are based on the means and standard deviations of triplicate cultures. Tests of significance were performed by the two-tailed Student's t test.

EXAMPLE 2

Assessment of Cytotozicity

The viability of WEHI-3 cells after exposure to rat Reptimed was assessed by the MTT viability assay as described in (20). MTT is (3,(4,5-dimethythiazol-2-yl)2,5-diphenyl-tetrazolium bromide, Sigma Chemical Company, St. Louis, Mo.). The assay measures the conversion of tetrazolium salt to a blue formazan product; the amount of conversion correlates closely with the number of intact mitochondria inside viable cells and therefore also correlates with the number of cells.

Figure 8:
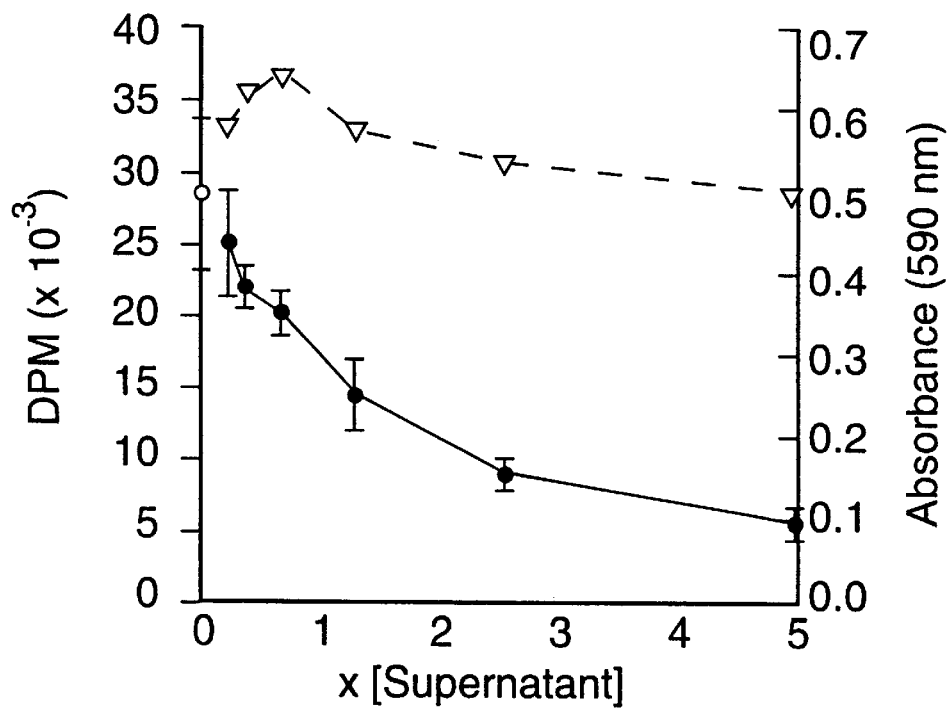
FIG. 8 shows an assay for viability of WEHI-3 cells treated with $C_{18}$ cartridge and P-2 gel filtration-purified Reptimed. The left vertical axis shows mean $^3$H-thymidine uptake in DPM×10$^{-3}$ of triplicate cultures treated with various concentrations of Reptimed and pulsed with $^3$H-thymidine (●). The right vertical axis shows mean UV absorbance at 590 nm of triplicate cultures treated with the same concentrations of Reptimed and pulsed with MTT (▽). Untreated WEHI-3 cultures included as a control were also pulsed with $^3$H-thymidine (○). Vertical bars represent standard deviation. The X axis indicates the fold increase in Reptimed concentration from the original bone marrow supernatants.

Cultures of WEHI-3 cells were incubated for 24 hours with various concentrations of $C_{18}$-cartridge and P-2 gel filtration-purified Reptimed under the conditions described in Example 1, with addition in the last four hours of either 25 ng/well MTT or 0.5 $\mu$Ci/well $^3$H-thymidine. For the MTT-treated cultures, formazan blue crystals were solubilized with developing reagent as described in (20) and absorbance was measured at 590 nm in a 96-well plate reader (Titertek Multiskan Plus, Flow Labs, Mississauga ON). $^3$H-thymidine-treated cultures were harvested and counted as described in Example 1. Results are shown in FIG. 8. Concentrations of Reptimed that produced up to 80% or greater inhibition of $^3$H-thymidine incorporation did not affect tetrazolium salt conversion, indicating that the suppression of cellular proliferation is not due to an effect on cellular viability.

EXAMPLE 3
Characterization of Reptimed

Liquid thromatography/Mass spectrometry (LC-MS):

Ionspray mass spectrometry was performed at the National Research Council Institute of Biological Sciences, Ottawa. The LC-MS equipment consisted of an Applied Biosystems solvent delivery system fluting into the ionspray ionization interface of a Sciex triplet quadrupole mass spectrometer (Perkin-Elmer/Sciex Instruments). Reptimed obtained from rat bone marrow cells and purified by solid phase extraction, gel filtration, anion exchange FPLC and reverse phase HPLC, as described in Example 1, was injected directly into the mass spectrometer.

Figure 12:
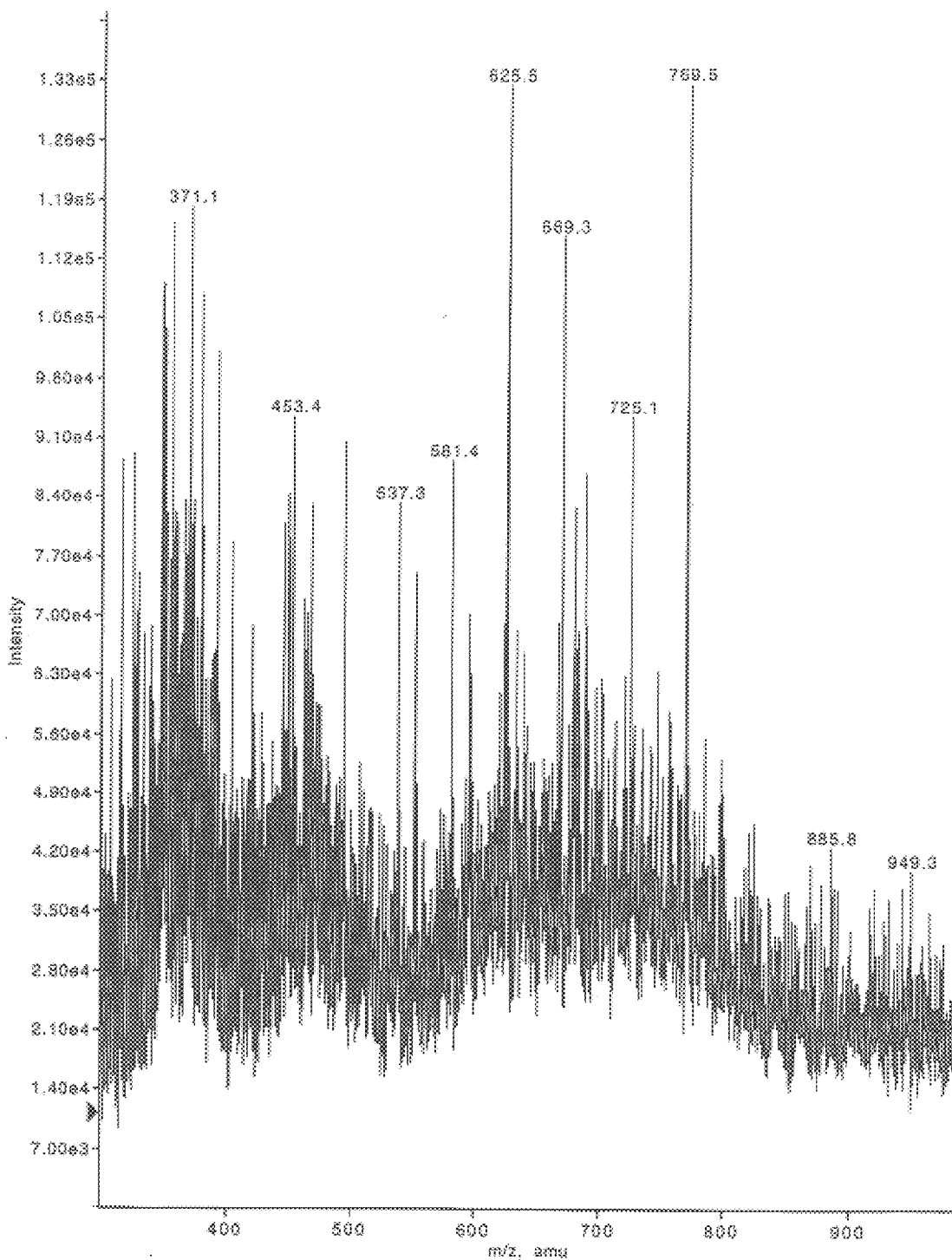
FIG. 12 shows a mass spectral analysis of the biologically active fraction from FIG. 11. The vertical axis shows per cent relative intensity. The X axis shows mass over charge ratio.

FIG. 12 shows that by direct injection. the highly purified fraction from the $C_a$ column contained a number of singly protonated ions including those at 949.3. 885.8, 769.5, 725.1, 669.3, 625.5, 581.4, 537.3, 453.4 and 371.1. Over a series of experiments, one singly protonated ion at 625.5 was found to be consistently associated with biological activity.

Figure 13:
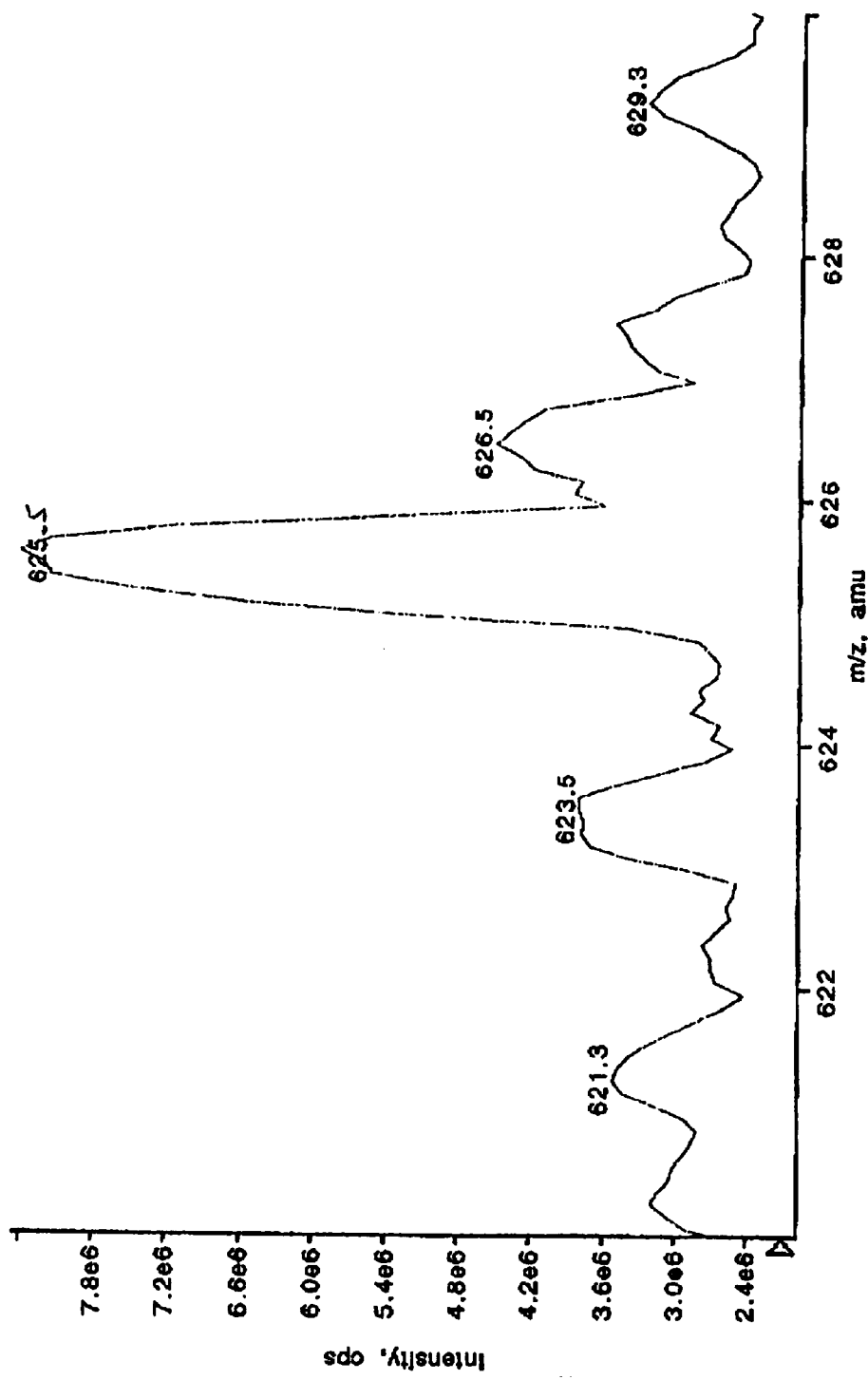
FIG. 13 shows a mass spectral analysis of the same biologically active fraction covering intensity of ions of MW. 621.3 to 629.3. Singly protonated ion at 625.5 found to be consistently associated with biological activity also showed the highest intensity.
Figure 14:
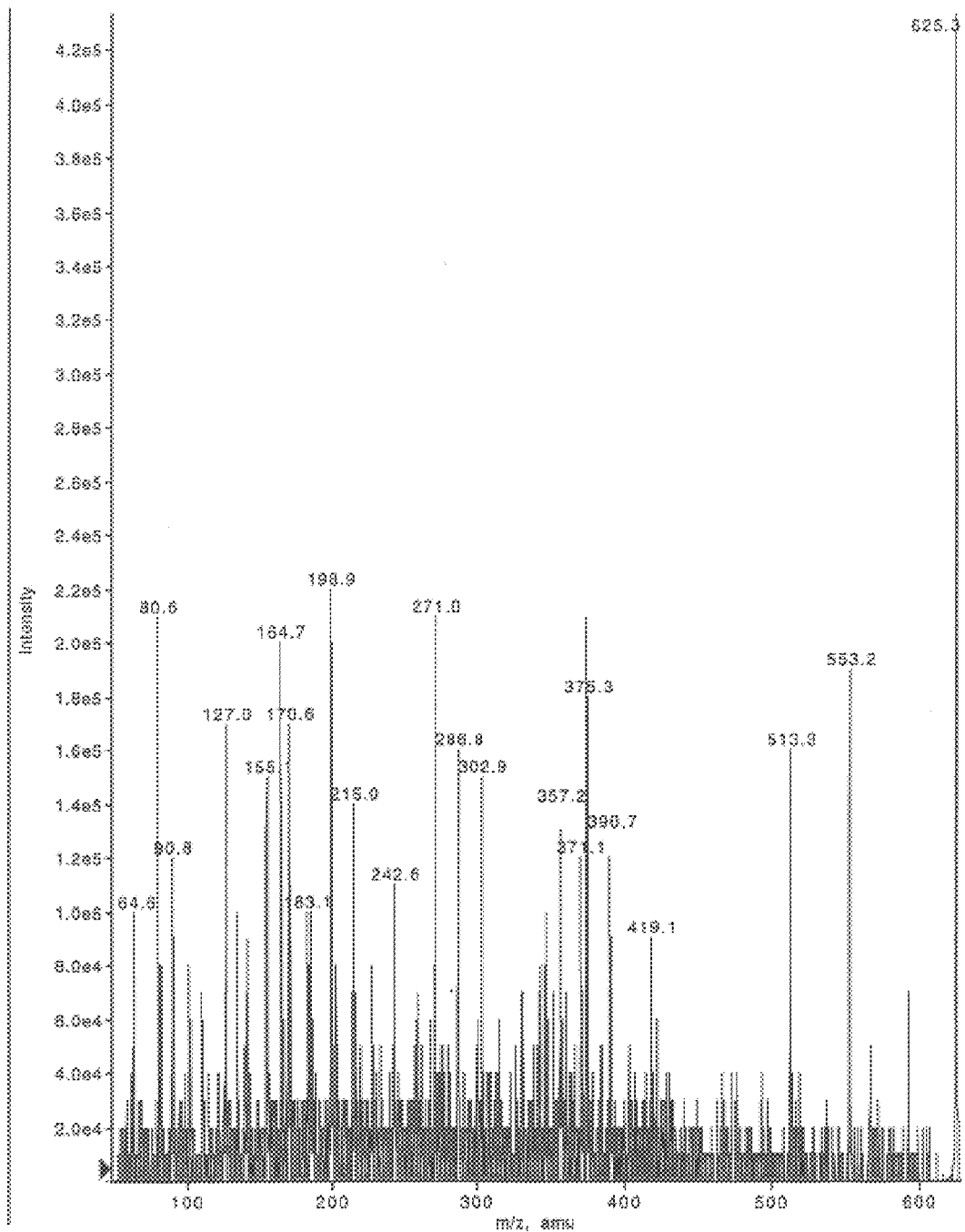
FIG. 14 shows a daughter ion analysis of 625.5 collision-induced dissociation using tandem mass spectrometry. The left vertical axis shows per cent relative intensity. The X axis shows mass over charge ratio.

The structure of the ion at 625.5 was examined by daughter ion analysis using collision-induced dissociation (CID) and mass spectral analysis of the resulting fragments. Using tandem mass spectrometry on the Sciex Machine. Reptimed purified as described above was injected through the ionspray interface and the ion at 625.5 was selected for CID. The mass spectrum of the resulting daughter ions are shown in FIG. 13. The major fragment of 625.5 had m/z ratios of 553.2, 513.3, 419.1, 390.7, 375.3, 371.1, 357.2, 302.9, 266.8. 271.0, 242.6, 215.0, 198.9, 183.1, 170.6. 164.7, 155.1, 127,0, 90.8, 80.6 and 64.6.

EXAMPLE 4
Suppression of Growth of Leukemic Cell Lines

Cell lines used in this study were the mouse myelomonocytic leukemia WEHI-3, obtained from the American Type Culture Collection (ATCC), Rockville Maryland, the mouse monocytic leukemia J774a (provided by Dr. M. Huff. University Hospital. London ON), the mouse myeloblast M1 (ATCC), the human promyelomonocytic leukemia HL-60 (provided by Dr. J. Harris, London Regional Cancer Centre). the human histiocytic lymphoma U-937 (ATCC). and the human chronic myelogenous leukemia K-562 (ATCC). Cell lines were maintained by regular passage in 25 cm$^2$ tissue culture flasks (Nunc plastics. Roskilde, Denmark) in RPMI-1640 medium supplemented with 10% feral bovine serum, 2 mM L-glutamine. 100 U/ml penicillin G. 100 $\mu$g/ml gentamycin (Gibco). Cells in log phase growth were plated at $2\times10^4$ cells/well in 96-well flat-bottom culture plates (Nunc) with or without dilutions of rat Reptimed purified by $C_{18}$ cartridge and P-2 gel filtration. Total volume per culture well was 200 $\mu$L. Cultures were incubated under standard conditions for 48 hours, including a 4-hour pulse with 0.5 $\mu$Ci/well $^3$H-thymidine (ICN-Flow, Mississauga ON). Cultures were harvested onto glass fibre filter paper (90×120 mm printed filtermat "A", Wallac, Turku, Finland) on an automatic 96-well cell harvester (Tomtec 96, Orange Conn.) and counted on a Microbeta 1450 liquid scintillation counter (LKB/Wallac) using an IBM PS/2 model 30 286 computer.

Figure 15:
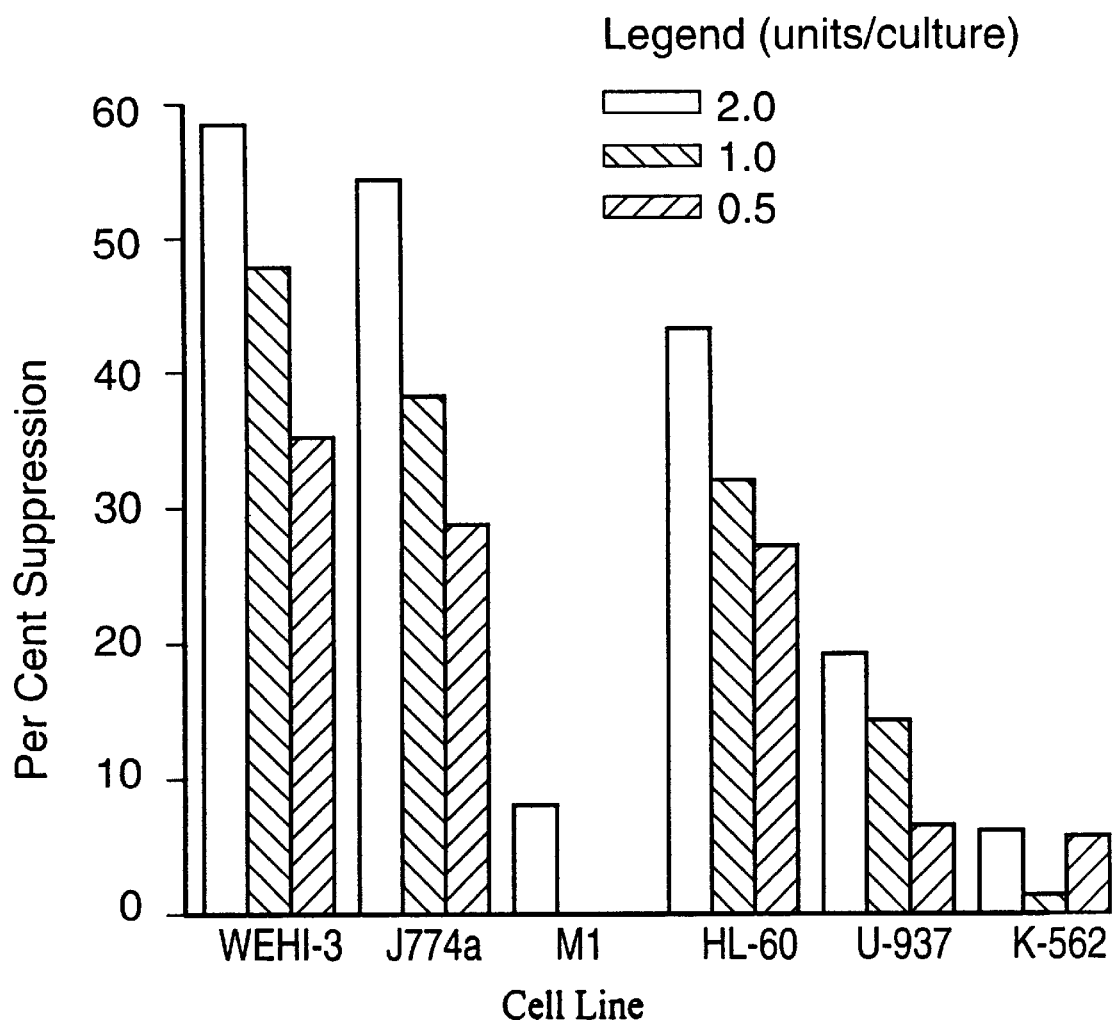
FIG. 15 shows suppression of growth of myeloid leukemia cell lines by $C_{18}$ cartridge and P-2 gel filtration-purified Reptimed. The Y axis shows per cent suppression of each cell line by various concentrations of Reptimed (open bars, 2.0 units/culture; hatched bars rising right, 1.0 units/culture; hatched bars rising right, 1.0 units/culture; hatched bars rising left, 0.5 units/culture). The X axis indicates the name of each cell line tested.

Constitutive proliferation for each cell line was as follows: 41486±2776 (WEHI-3), 8155±582 (J774a), 16047±904 (M1), 28228±1538 (HL-60), 70045±2603 (U-937), and 74073±1981 (K-562). Results are expressed as per cent suppression of constitutive proliferation of each cell line and are shown in FIG. 15. Data shown is based on the mean values of triplicate cultures. At 1.0 units/culture of Reptimed (the dose which suppresses proliferation of WEHI-3 cells by 50%), J774a cells were suppressed by 36%, HL-60 by 30%, U-937 by 13% and K-562 by 1%. M1 cells were not significantly suppressed. Repeated experiments confirmed that K-562 and M=I cells are insensitive to Reptimed at similar or higher concentrations; while J774a, HL-60 and U-937 are suppressed, but to a lesser extent than WEHI-3.

EXAMPLE 5
Suppression of Growth of Mouse Myeloid Colonies

BALB/c or C57Bl/6 mice were obtained from Charles River Breeding Laboratories (St. Constant, PQ). Mice were bred and maintained at the University of Western Ontario animal care facilities. Female mice of ages 6-12 weeks were used in all experiments.

Cell Culture Media

Unless otherwise indicated, complete RPMI medium consisted of RPMI-1640 supplemented with 10% fetal bovine serum, 2 mM L-glutamine, 100 U/ml penicillin G, 100 $\mu$g/ml streptomycin, and 25 $\mu$g/ml gentamicin (Gibco-BRL, Burlington ON).

Preparation of Conditioned Media

WEHI-3 murine myelomonocytic cells (ATCC) have been described as a source of IL-3 (21) and L-929 murine fibroblastic cells (ATCC) have been described as a source of murine M-CSF (22). WEHI-3 cells were grown in 25 cm$^2$ tissue culture flasks (Nunc plastics, Roskilde Denmark) in complete RPMI medium. At confluence WEHI-3 cells were harvested, washed once in HBSS (Gibco) by resuspension followed by centrifugation at 1500 rpm×7 minutes and re-cultured in 75 cm$^2$ tissue culture flasks (Nunc) at $1\times10^6$ cells/ml in complete RPMI medium. After 24 hours of incubation under standard conditions, cells were removed from the conditioned medium by centrifugation at 2000 rpm for 10 minutes.

L-929 cells grown as described for WEHI-3 cells were harvested using trypsin-EDTA (Gibco) followed by washing 3×in HBSS, then seeded into 75 cm$^2$ tissue culture flasks at $1\times10^4$ cells/ml in complete RPMI medium. Cells were grown for 9 days under standard conditions, then supernatants were decanted and centrifuged for 10 minutes at 2000 rpm. Conditioned media were filtered using a 0.8 $\mu$m Acrodisc syringe filter (Gelman) and stored frozen at $-20°$ C. until use.

Granulocyte-macrophage Colony-forming Unit (CPU-GK) Assay

Normal BM cells were aspirated from the femurs and tibias of 6–12 week old BALB/c or C57Bl/6 mice. The cells were washed three times and resuspended at a concentration of $1\times10^5$ cells/ml in RPMI-1640 supplemented with 20% FBS, 200 mM L-gluta=mine, 100 $\mu$g/ml gentamicin, 25 $\mu$g/ml fungizone (Gibco), $5\times10^{-5}$ M 2-mercaptoethanol (Sigma), 10% WEHI-3 conditioned medium and 0.3% agar (Difco, Detroit Mich.). 1.5 ml of cell suspension was plated in triplicate in 35 mm petri dishes (Lux, Miles Labs, Naperville Ill.) and allowed to solidify at room temperature for 10 minutes. The dishes were incubated for 7 days at 37° in a humidified atmosphere with 5% $CO_2$. Colonies containing more than 50 cells were counted using an inverted microscope (Olympus, Tokyo, Japan).

Macrophage Colony-forming Unit (CPU-M) Assay

Normal BALB/c or C57Bl/6 BM cells were prepared as described for the CFU-GM assay above. Cells were resuspended at a concentration of $5\times10^4$ cells/ml in RPMI-1640 supplemented with 20% FBS, 200 mM L-glutamine, 100 $\mu$g/ml gentamicin, 25 $\mu$g/ml fungizone (all from Gibco), $5\times10^{-5}$ M 2-mercaptoethanol (Sigma), 20% L-929 conditioned media and 0.3% agar. 1.5 ml of cell suspension was plated in triplicate in 35 mm petri dishes (Lux) and allowed to solidify at room temperature for 10 minutes. The dishes were incubated for 9 days at 37° C. in a humidified atmosphere with 5% $CO_2$. Colonies containing more than 50 cells were counted using an inverted microscope.

Figure 16A:
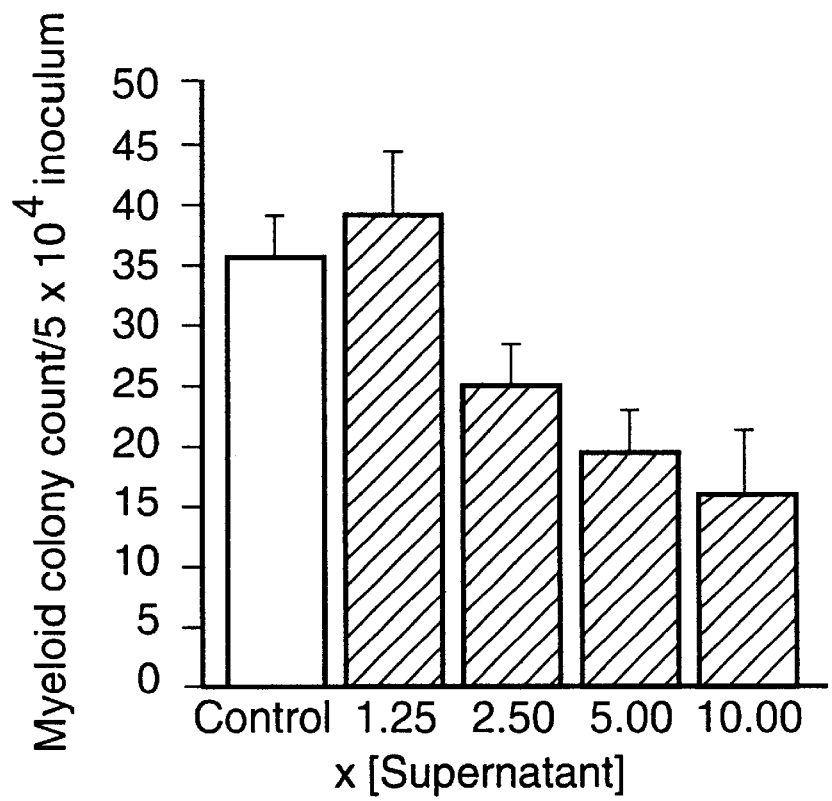
FIGS. 16A and B show suppression of growth of myeloid colonies by mouse Reptimed.
Figure 16B:
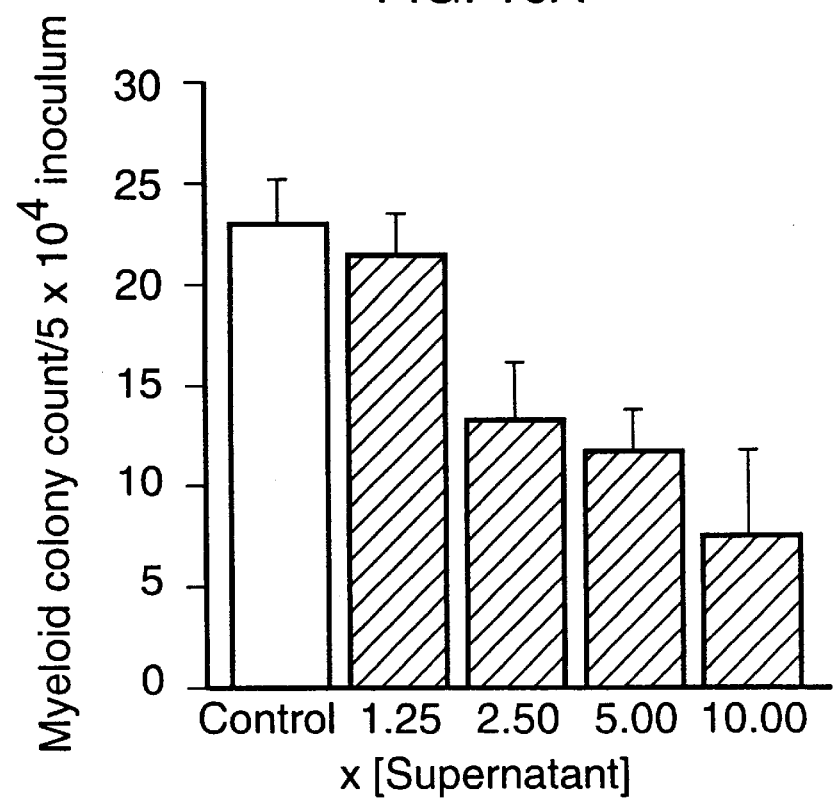
FIG. 16B shows M-CSF-induced macrophage colonies. The Y axis indicates mean myeloid colony counts per $5×10^4$ bone marrow cells inoculated. Cultures were treated with culture medium alone as a control (open bars) Or various dilutions of mouse Reptimed (hatched bars). Vertical error bars represent standard deviation. The X axis indicates the fold increase in Reptimed concentration from the original preparation.
Figure 17:
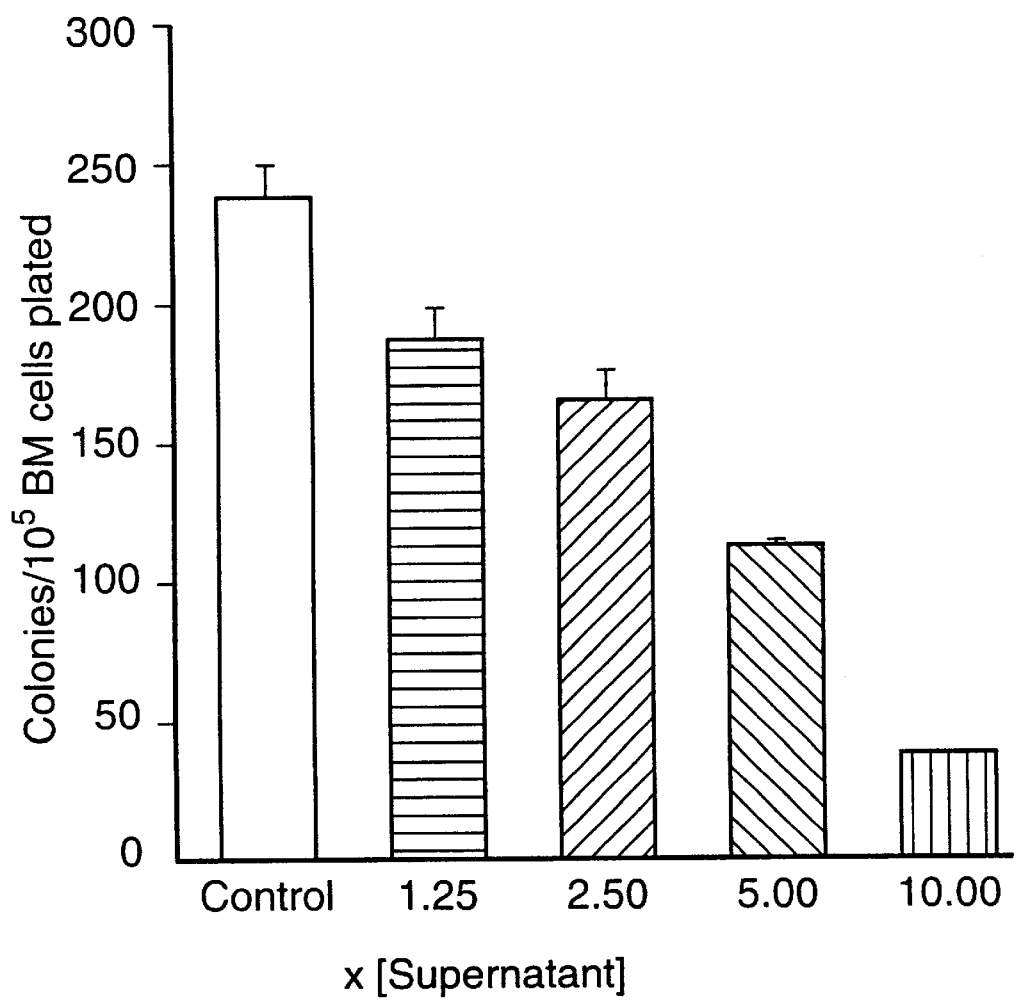
FIG. 17 shows suppression of growth of IL-3-induced granulocyte-macrophage colonies by rat Reptimed purified by $C_{18}$ cartridge. The Y axis indicates mean colony counts per $10^5$ bone marrow cells inoculated. Cultures were treated with culture medium alone as a control (open bar) or various dilutions of Reptimed (hatched bars). Vertical error bars represent standard deviation. The X axis indicates the fold increase in Reptimed concentration from the original preparation.

C18-cartridge purified mouse Reptimed was tested for its effects on myeloid colony formation. FIG. 16A shows that Reptimed suppresses IL-3-induced granulocyte-macrophage colony formation, and FIG. 16B shows that Reptimed suppresses M-CSF-induced macrophage colony formation. Suppression of myeloid colony formation was dose-dependent and not MHC-restricted, since Reptimed suppressed growth of colonies from several mouse strains. The same preparation had no effect on erythropoietin-induced erythroid colonies or LPS-induced sIg+ B cell colonies (data not shown). To confirm that Reptimed prepared from rat bone marrow is also suppressive, $C_{18}$-cartridge-purified rat Reptimed (prepared as described in Example 1) was tested for its effect on IL-3-induced mouse granulocyte-macrophage colony formation. The results, in FIG. 17, show that rat Reptimed suppressed granulocyte-macrophage colonies in a manner similar to Reptimed prepared from mouse bone marrow. The dilutions of Reptimed used in FIG. 16. (mouse) and FIG. 17 (rat) were prepared identically and are comparable in biological activity.

EXAMPLE 6

Prevention of Bladder Tumour Formation.

Tumour Cells. FANFT-induced (N[4-(5-nitro-2 furyl)-2 thiozolyl] formamide) MBT-2 transitional cell carcinoma of the bladder was maintained in vivo as a solid, subcutaneously growing tumour by serial transplantation in syngeneic C3H/He female mice (Charles River), and in vitro in RPMI 1640 medium plus 10% fetal calf serum. Single tumour cell suspensions were prepared by mincing the tumour under sterile conditions and adding to the minced tissue 5 ml. of an enzyme cocktail containing a mixture of 1% collagenase (Sigma, type II), 0.01% proteinase K (Sigma) and 0.01% DNA-ase (Sigma) in Dulbecco's PBS containing $Ca^{++}$ and $Mg^{++}$ salts. The cells were then washed twice with RPMI 1640 medium, resuspended to the required concentration and either inoculated subcutaneously (s.c.) into the flank region as heterotopic tumours or implanted intravesically into the bladders as orthotopic tumours.

Heterotopic Tumours. Heterotopic tumours were established by inoculation of $5\times10^5$ MBT-2 tumour cells subcutaneously (s.c.) in the flank region. Approximately 90% of all the inoculated animals developed s.c. tumours by day 12 after tumour cell inoculation. Heterotopic tumours represented solid mass with minimum or no necrosis at the early stage of growth but with increasing necrosis as tumours progressed in size.

Orthotopic Tumours. Orthotopic tumours were established by intravesical tumour cell implantation into bladders of female mice via the urethra as previously described. Briefly, mice were anaesthetized with a single dose of intraperitoneal sodium phenobarbital (130 mg/kg body weight). The bladder was catheterized via the urethra with a 24-gauge plastic intravenous cannula under sterile conditions. The bladder mucosa was then traumatized by instillation of 0.1 ml of 0.1N HCL solution for 15 seconds, neutralized with 0.1 ml of 0.1N KOH and flushed with sterile saline. A total of $5\times10^5$ MBT-2 tumour cells were instilled via the cannula and the urethra was compressed for 30 minutes to prevent premature bladder evacuation. Six days later, the animals were serially assessed by MRI for detection of intravesical tumours. MRI Protocol. Anaesthetized mice were placed in a 1.8 MHz volume imaging coil and imaged using a Bruker M5L 1.9/30 MR Imager. Whole animals were scanned transversely (4 contiguous, 3 mm slices) and sagitally (4, 5 mm. slices 2.5 mm gap) using $T_1$-weighted spin echo sequences. A 1 ml syringe containing a 1:100 dilution of Gadolinium-DTPA (a paramagnetic MRI contrast agent, Magnevist$^R$) was placed vertically over the urethra as an external (fiducial) marker for repetitive positioning in a 35 mm inner diameter loop gap resonator. To delineate bladder tumour tissue from normal bladder and normal abdominal contents high contrast images were obtained by using a bladder inflation technique using neat Gadolinium-DTPA. A specific volume (0.1 ml) of fluid was used for inflating the bladder. Thus, the tumour in the bladder appeared as signal-containing structure outlined against a black negative background. Mice with clinically palpable tumours and normal untreated mice were used as the "tumour-bearing control" group and "normal control" group respectively for MRI imaging.

Initially tolerance to Reptimed was assessed by treatment of normal mice with 3 multiple intravesical instillations and 3 intraperitoneal inoculations of factor (doubling dilutions in normal saline, ranging from 1 in 100 to 1 in 400). Mice tolerated repeated intraperitoneal and intravesical administration of 1 in 100 dilutions well with no apparent toxicity. The intravesical/intraperitoneal route and the 1 in 100 dilution were subsequently used for treatment of MBT-2 tumour-bearing mice.

Assessment of treatment with Reptimed: The direct in vivo anti-tumour action of Reptimed was evaluated on the growth of heterotopic and orthotopic MBT-2 bladder tumours as follows:

(i) —Treatment of Heterotopic Tumours. The anti-tumour effect was evaluated against small (approx. 10 mm in diameter) s.c. tumours. Two groups of mice were used (n=5/group):

Group 1 (heterotopic, treated with Reptimed): mice received one initial s.c. injection of $5\times10^5$ tumour cells and 0.1 ml of 1 in 100 dilution of C18 cartridge purified, mouse Reptimed on day 0. The animals were subsequently inoculated intraperitoneally with 0.1 ml of 1 in 100 dilution of Reptimed on days 3 and 5 after tumour cell inoculation.

Group 2 (control, heterotopic, not treated with Reptimed): mice received an s.c. tumour cell inoculum alone (5×10⁵/0.1 ml) on day 0. The animals were subsequently inoculated intraperitoneally with normal saline (0.1 ml) at day 0 and at days 3 and 5 after tumour cell inoculation. Twenty one days following inoculation the mice in each group were examined for presence of palpable s.c. tumours and the tumour volumes were assessed.

(ii) —Treatment of Orthotopic Tumours. The effectiveness of Reptimed therapy on the outgrowth and subsequent progression of orthotopic MBT-2 tumours was evaluated on the following two groups of mice (n=10/group):

Group 3 (orthotopic, treated with Reptimed): mice received one initial intravesical instillation of C18 cartridge purified, mouse Reptimed (0.1 ml of 1:100 dilution) with 5×10⁵ MBT-2 tumour cells on day 0. The mice were subsequently injected intraperitoneally with 0.1 ml Reptimed of 1:100 dilution at days 3 and 5 post tumour implant.

Group 4 (control, orthotopic, not treated with Reptimed): mice were instilled intravesically with 0.1 ml saline and 5×10⁵ MBT-2 tumour cells at day 0. The mice were subsequently instilled intravesically and injected intraperitoneally with 0.1 ml normal saline at days 0, 3 and 5 post tumour implant. Group 3 and Group 4 mice were serially imaged by MRI 3 times a week from day 6 to day 33 after tumour implantation.

MRI Monitoring. The MRI scans of treated bladders were compared to those of control, untreated bladders. Tumour volumetric measurements were performed using a technique for quantitating tissue volumes that has been applied in the clinical setting(23). Briefly, the MRI scans of tumour-bearing mice were analyzed using a PC-based Image Processing package ("Image-Pro Plus") that allows standard image manipulations such as shifting, rotating and statistical analysis on selected areas of interest. Measurement of tumour surface areas was done by mapping out intraluminal regions of interest and delineating tumour tissue from the surrounding normal bladder tissue and the occupied urine within the bladder.

Histology. For histologic examination, mice were sacrificed after completion of therapy and cystectomy was performed. Histological examination was performed with haematoxylin-phloxine-saffron (HPS) staining on formalin fixed whole bladder sections from the cystectomy specimen. The bladders were examined for: tumour incidence and histologic grade and stage. All light microscopy sections were examined and correlated with MRI findings.

Figure 18A:
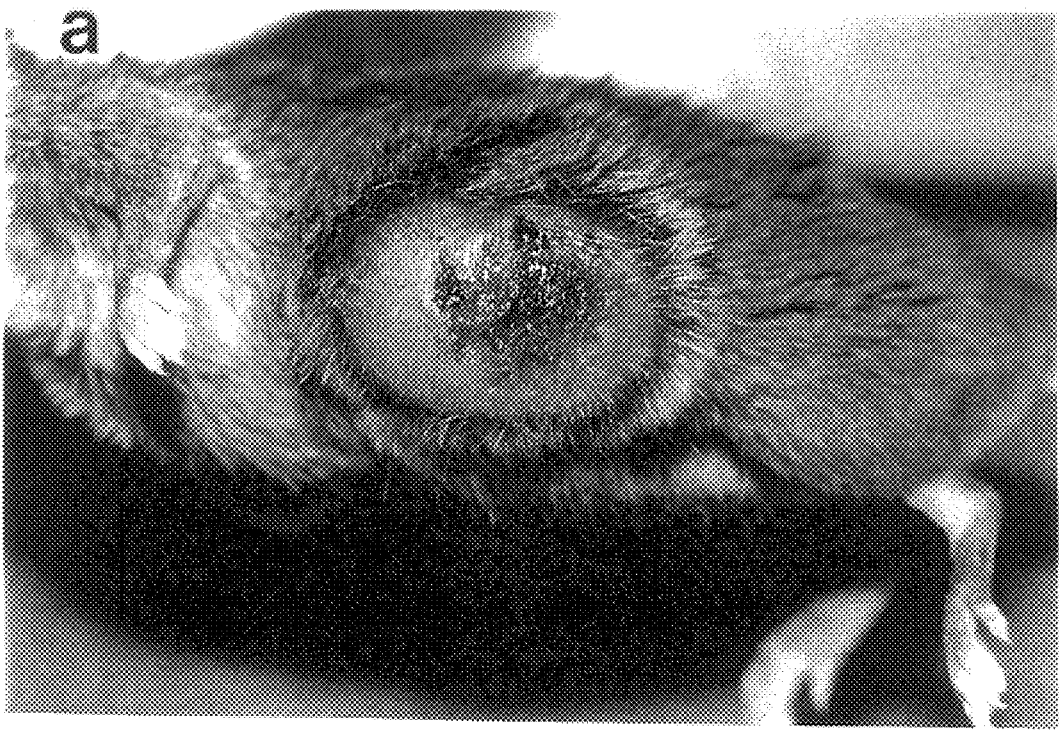
FIGS. 18A and B show the effect of Reptimed on the growth of heterotopic subcutaneous (s.c.) MBT-2 tumours at 21 days after tumour injection: (a) control tumour-bearing mice without Reptimed treatment; (b) mice inoculated s.c. with Reptimed in admixture with tumour cells and then i.p. with multiple inoculations of Reptimed (q×3).
Figure 18B:

Effect of Reptimed on growth of heterotopic KBT-2 Tumours. All mice treated with Reptimed (group 1) showed a complete inhibition of tumour growth by day 21 following tumour cell implantation , as seen in FIG. 128b. In contrast, all group 2 (control) untreated mice inoculated with tumour cells alone had s.c. tumours after the same time period, as seen in FIG. 18a.

Figure 19A:
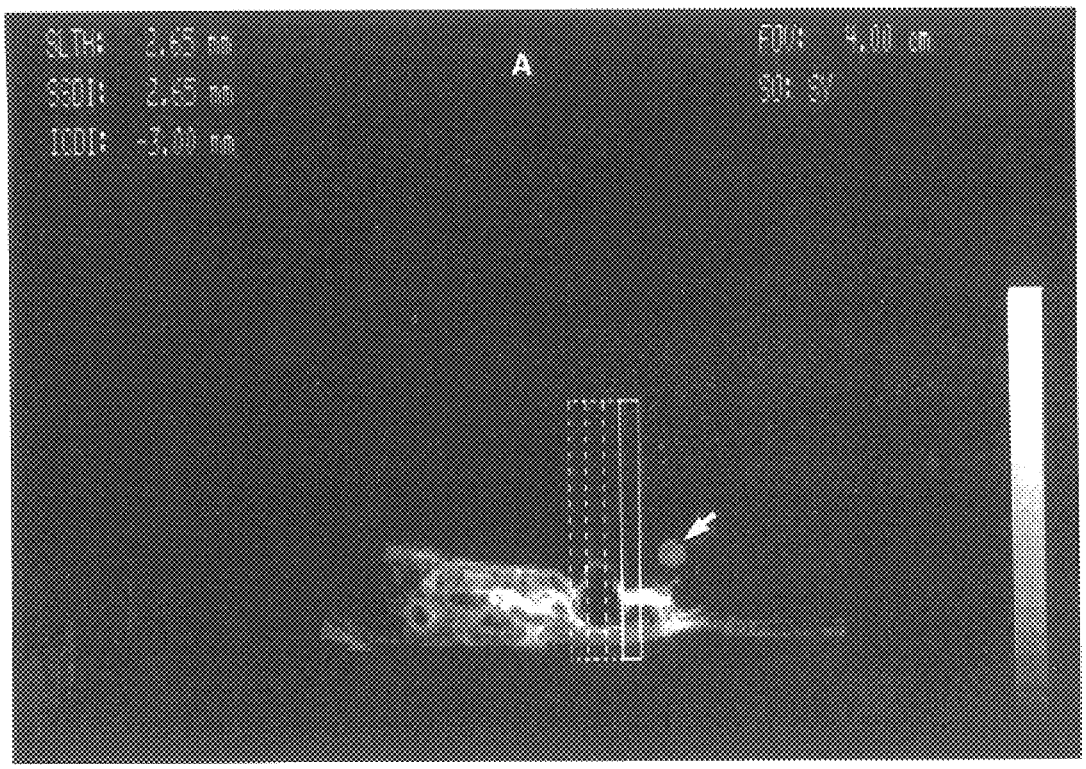
Figures 20A, 20B, 20C, 20D, 20E:
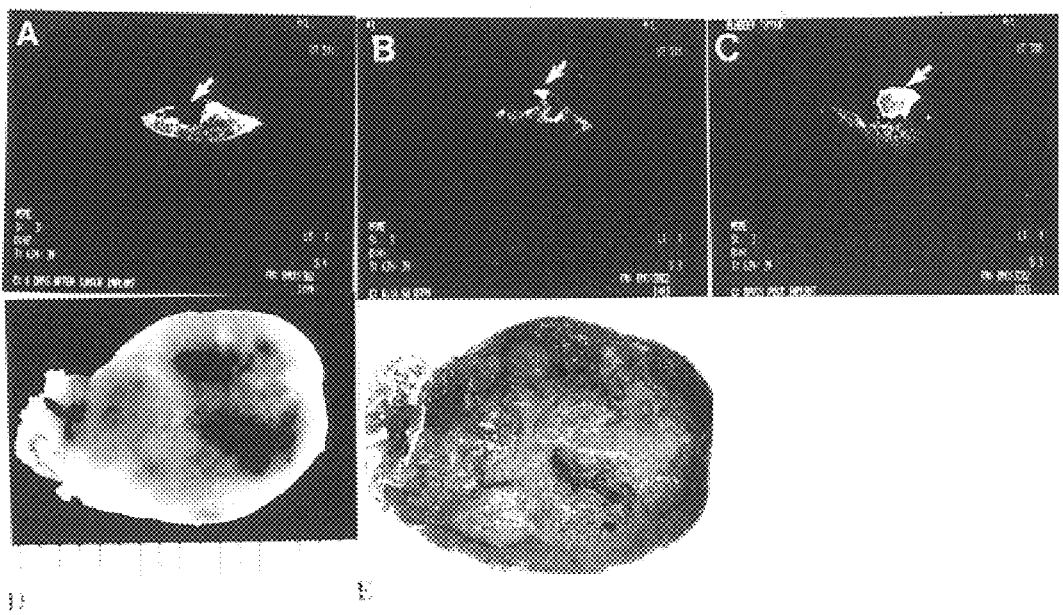
FIGS. 20A–E show MR images of control bladder; 20A: 6 days post MBT-2 tumour implant; 20B: 18 days post implant, partially filled with tumour; 20C: 21 days post implant, bladder completely filled with tumour; 20D: corresponding gross mount on day 21; 20E: corresponding light microscopy on day 21.

Effect of Reptimed on growth of Orthatopic MBT-2 Tumours. FIGS. 19A to 19E illustrate representative MRI scans of a control bladder (tumour implant and no Reptimed) in a sagittal plane with 4 contiguous, 3 mm slices covering inflated bladder as labelled with contrast agent relative to the external marker as indicated by solid white arrow (FIG. 19A). FIGS. 19B and C illustrate MR images of a control bladder in a transverse plane at days 6 and 14 post tumour implant respectively. No visible tumour was detectable on MRI at day 6 (FIG. 19B). When imaged at day 14, MRI revealed the bladder partially filled with tumour (FIG. 19C). Serial MR imaging of a control tumour-bearing mouse at day 21 post tumour implant showed extensive bladder involvement, with tumour almost completely filling the lumen (FIGS. 20A–C). FIG. 19D, E and FIG. 20D, E illustrate the corresponding gross mounts and light microscopy of bladders for the control tumour-bearing mice at days 14 and 21 post tumour implant respectively.

Figure 21A:
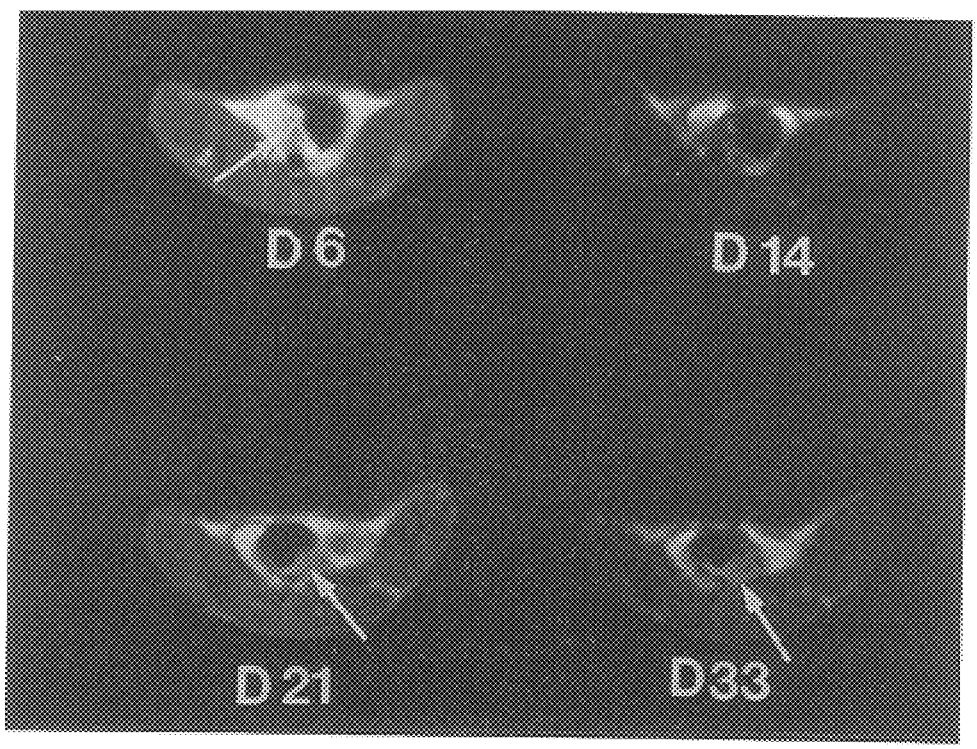
FIGS. 21A and B show 21A: serial MRI of representative Group 3 (orthotopic tumour, treatment with Reptimed) bladder at Days 6, 14, 21 and 33 post tumour implant. Presence of intraluminal tumour growth is indicated by the arrow; 21B: serial MRI of representative control bladder at Days 6, 14, 21 and 33 post tumour implant. Presence of intraluminal tumour growth is indicated by the arrow.
Figure 21B:
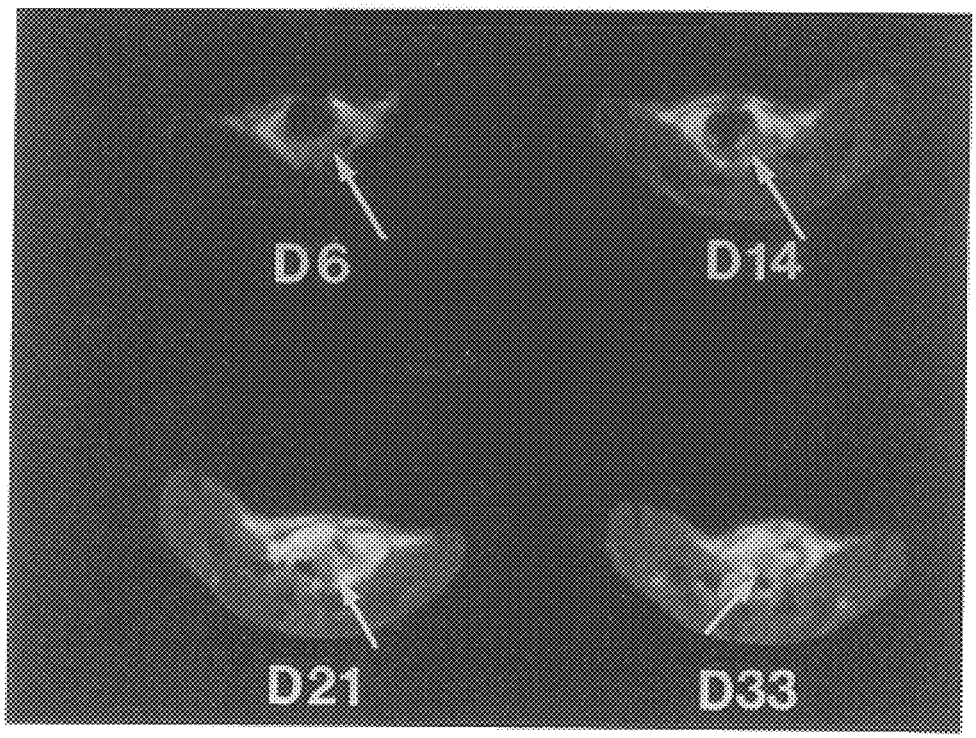
Figure 22A:
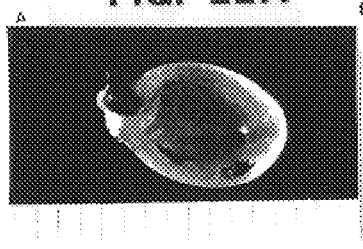
FIGS. 22A–F show histopathology examination of whole mount bladder sections; 22A and 22B: show gross pathology and histology of treated bladders showing no visible tumour at Day 33 post tumour implant; 22C: corresponding histology at day 33 showing normal epithelium with foci of carcinoma in situ; 22D and 22E: corresponding gross pathology and histology of control untreated bladders showing extensive tumour involvement at Day 33 post tumour implant; 22F: corresponding histology at day 33 showing deeply invasive transitional cell carcinoma of the bladder.
Figure 22B:
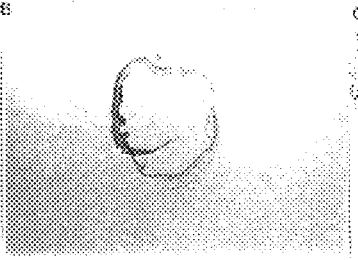
Figure 22C:
Figure 22D:
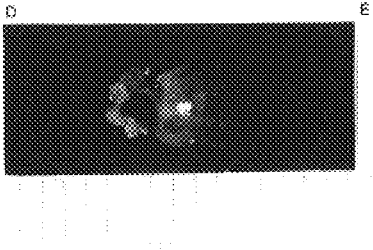
Figure 22E:
Figure 22F:
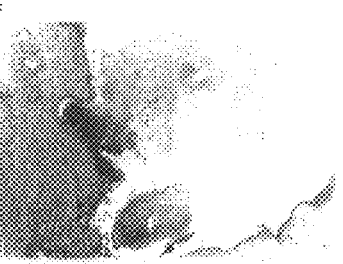

FIGS. 21A and B illustrate the course of tumour growth evident from serial MRI scans of treated mice (representative of Group 3) and control untreated mice (representative of Group 4) from day 6 till day 33 post tumour implant. Significant tumour growth inhibition was evident from day 14 post tumour implant in the treated compared to untreated animals (FIGS. 21A, B). Sequential MRI scans on day 21 revealed areas of residual intraluminal tumours. No significant tumour growth was apparent on MRI at day 33 post tumour implant. This was confirmed by gross pathology and histology examination of the corresponding whole mount bladder sections revealing mostly normal epithelium with foci of carcinoma in situ in the treated group (FIGS. 22A–C). Histological examination of bladders of the control untreated group revealed deeply invasive tumours (FIGS. 22D–F).

Quantitation of tumour surface areas (mm²) of intravesical tumours from four individual control untreated and seven individual treated mice is summarized in Table 1. Significant tumour growth inhibition ($p<0.005$–$p<0.001$) was observed in the treated group compared to the control untreated group at days 18, 24 and 28 post tumour implant.

EXAMPLE 7

Suppression of the Mixed Lymphocyte Reaction.

The mixed lymphocyte reaction (MLR) defines an allogeneic recognition, and subsequent proliferation, of a responding population of lymphocytes against a (MHC) histoincompatible stimulator population of lymphocytes. In an in vitro murine MLR, two MHC-mismatched strains are used (e.g. C57BL/6 (H-2$^b$) as the responder population; Balb/c (H-2$^d$) as the stimulator population). The C57BL/6 responders at 4.0×10⁵/well were co-cultured with 6.0×10⁵/well Balb/c stimulator cells in a 96 well flat-bottom plate (37° C./5% $CO_2$). The Balb/c stimulators were previously irradiated with 2500 rads in order to prevent their proliferation. After a 5 day culture, the proliferation of the responding C57BL/6 population was measured by ³-TdR incorporation.

Figure 23:
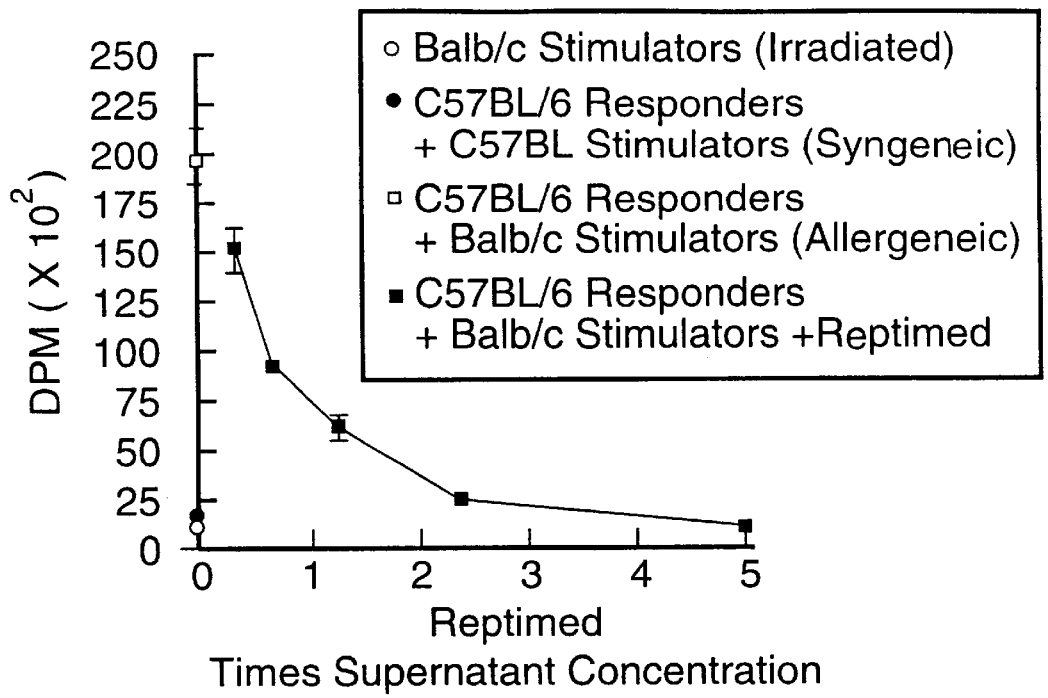
FIG. 23 shows the suppression of the mixed lymphocyte reaction by Reptimed.

Rat Reptimed was purified by $C_{18}$/P2 gel purification as described in Example 1 and its ability to suppress the proliferation of the responding lymphocyte population was assessed by adding it in a dilution series to the cultures at the beginning of the assay. As shown in FIG. 23, Reptimed suppressed H-TdR incorporation in the responding lymphocytes in a dose-dependent manner.

EXAMPLE 8

Suppression of IL-2 Production in Antigen-specific T Cells.

When mature T cells are stimulated through the T cell receptor (TCR) by their specific antigen, they are induced to produce their appropriate cytokine. This ability to respond to a specific antigen and to produce cytokine can be maintained in an immortalised hybridoma cell line. Such a hybridoma was used to examine the ability of Reptimed to down-regulate induction of synthesis of the cytokine IL-2 in T cells.

The hybridoma used was a myelin basic protein (MBP)-specific T cell hybridoma derived from the somatic cell hybridization of T lymphocytes from MBP-immunized SJL mice with the parental thymoma cell line BW5147. In this system, syngeneic antigen presentation cells take up the specific antigen and present it to the T cell hybridomas in the context of self-MHC. The T hybridomas recognize the antigen in the context of self-MHC via their T cell receptor (TCR) and are subsequently stimulated to produce IL-2. After 24 hours in standard culture conditions (37° C./5% $CO_2$) the cells were centrifuged, and the resultant supernatant (containing IL-2) was removed and stored at −20° C. The IL-2 produced was then quantified by using a murine IL-2 enzyme-linked immunoabsorbent assay (ELISA).

Antigen presentation cells (APCs) were lethally irradiated spleen cells from a SJL mouse (syngeneic to the T cell hybridomas). MBP antigen was used at 50 μg/ml, APCs at $2.5 \times 10^5$/well, and T cell hybridomas at $6.0 \times 10^4$/well in cRPMI tissue media. Reptimed ($C_{18}$, P2 gel filtration semi-purified from rat) was added to the cultures in various and the dilutions. IL-2 produced was quantified by using a murine IL-2 ELISA.

Figure 24:
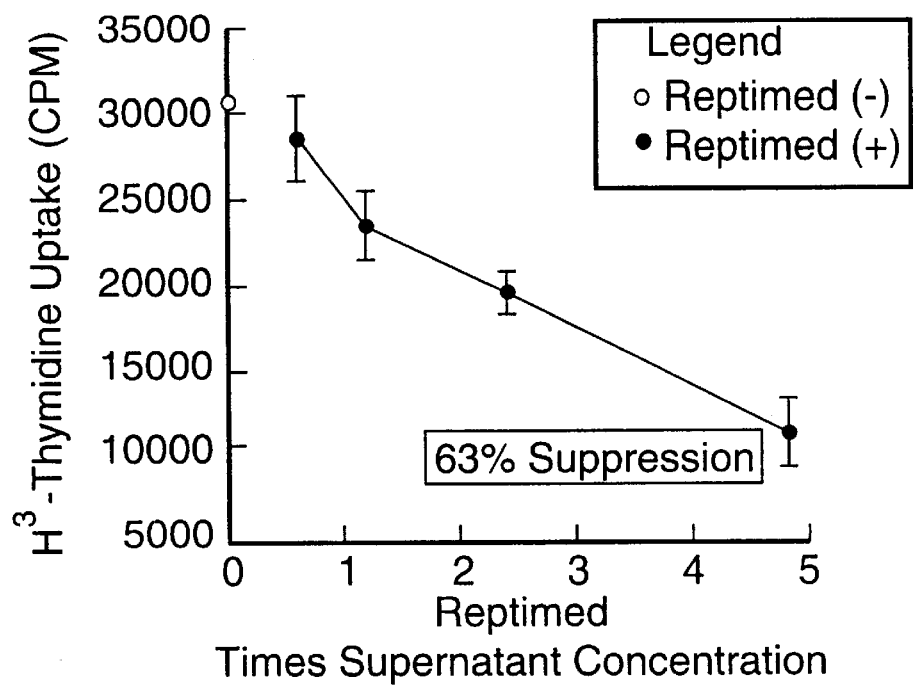
FIG. 24 shows suppression of proliferation of unstimulated MBP-specific T cell hybridomas by Reptimed.
Figure 25:
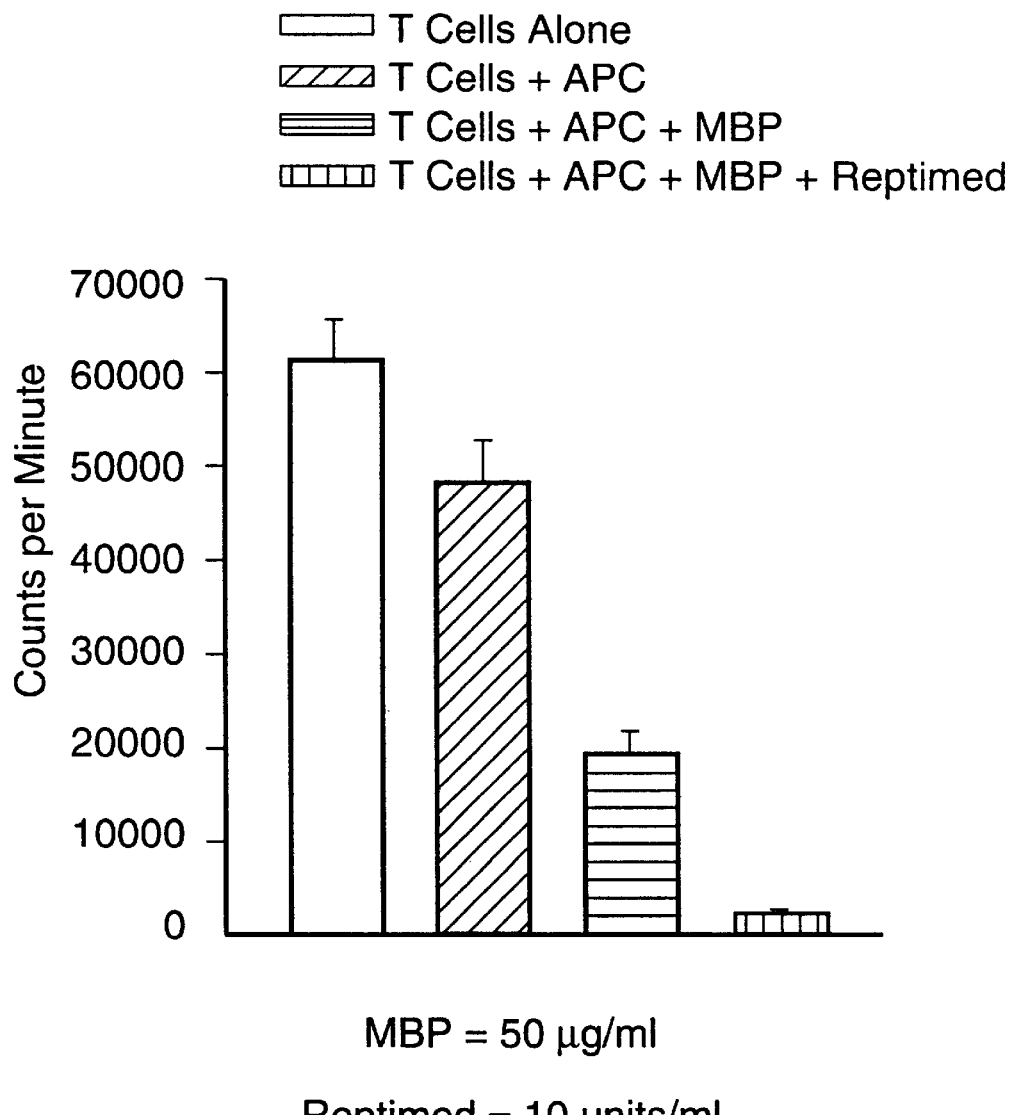
FIG. 25 shows the suppression of proliferation of MBP-specific T cell hybridomas (stimulated with MBP) by Reptimed.

FIG. 24 shows the dose-dependent suppression of $^3$H-Tdr incorporation in the unstimulated MBP-specific T cell hybridomas indicating inhibition of proliferation. FIG. 25 shows the suppression of proliferation of the T cell hybridomas after stimulation with MBP via syngeneic antigen presenting cells (APCs). FIG. 26 shows the down regulation of IL-2 production by Reptimed in the T cell hybridomas as demonstrated with ELISA.

EXAMPLE 9

Suppression of TNF-α Production in Activated Macrophages.

Mature nacrophages are induced to produce cytostatic molecules such as TNF-α and nitric oxide (NO) upon priming with IFN-γ, and activation with lipopolysaccharide (LPS). TNF-α is a pivotal protein that takes part in many immunological reactions and cytokine interactions, but it is also known to be a mediator of histopathological tissue damage. Reptimed was tested in a well established TNF-α cytotoxicity assay, which includes ThF-α production quantified by relative killing of a TNF-α sensitive cell (24) Nestel line, L-929.

TNF-α Production: Peritoneal cells were collected from mice injected 3 days previously with thioglycolate medium (10% wt/vol). The cells were washed twice and adjusted to $2 \times 10^6$ cells/ml in ice-cold HBSS and 100 μl aliquots were plated into 96-well flat bottomed microtiter plates. After a 1.5 hour incubation (standard culture conditions), the cultures were washed vigorously four times with warm HBSS to remove nonadherent cells, the wash medium was removed, and 100 μl of assay medium either alone or containing additional reagents (e.g. IFN-γ, LPS and Reptimed) was added to the adherent macrophage monolayers. After a 24 hour incubation (37° C./5% $CO_2$), the culture supernatants were collected and frozen at −70° C. until used in the L-929 cytotoxicity assay.

An appropriate number of macrophage cultures were primed to produce TNF-α in the presence or absence of various dilutions of rat Reptimed (purified by $C_{18}$ cartridge, P-2 gel purification as described in Example 1).

TNF-α quantification: Subconfluent monolayers of L-929 fibrosarcoma cells were trypsinized, washed, and $6 \times 10^4$ cells/well in complete media were plated into 96-well microtiter plates. The cells were allowed to adhere for 1 hour, the supernatant was removed, and 50 μl of RPMI 1640 supplemented with 10% FCS and 2 μg/ml actinomycin D were added. Culture supernatants to be assayed for TNF-α production were added, and after an 18 hour incubation 25 μl of 5 mg/ml 3-(4,5-dimethylthiazol-2-yl)- 2,5-diphenyltetrazolium bromide (MTT) were added. After a further 3–4 hour incubation, the reduced MTT was solubilized and the plate was read at 570 nm on a ELISA plate reader (690 nm reference wavelength).

Figure 27:
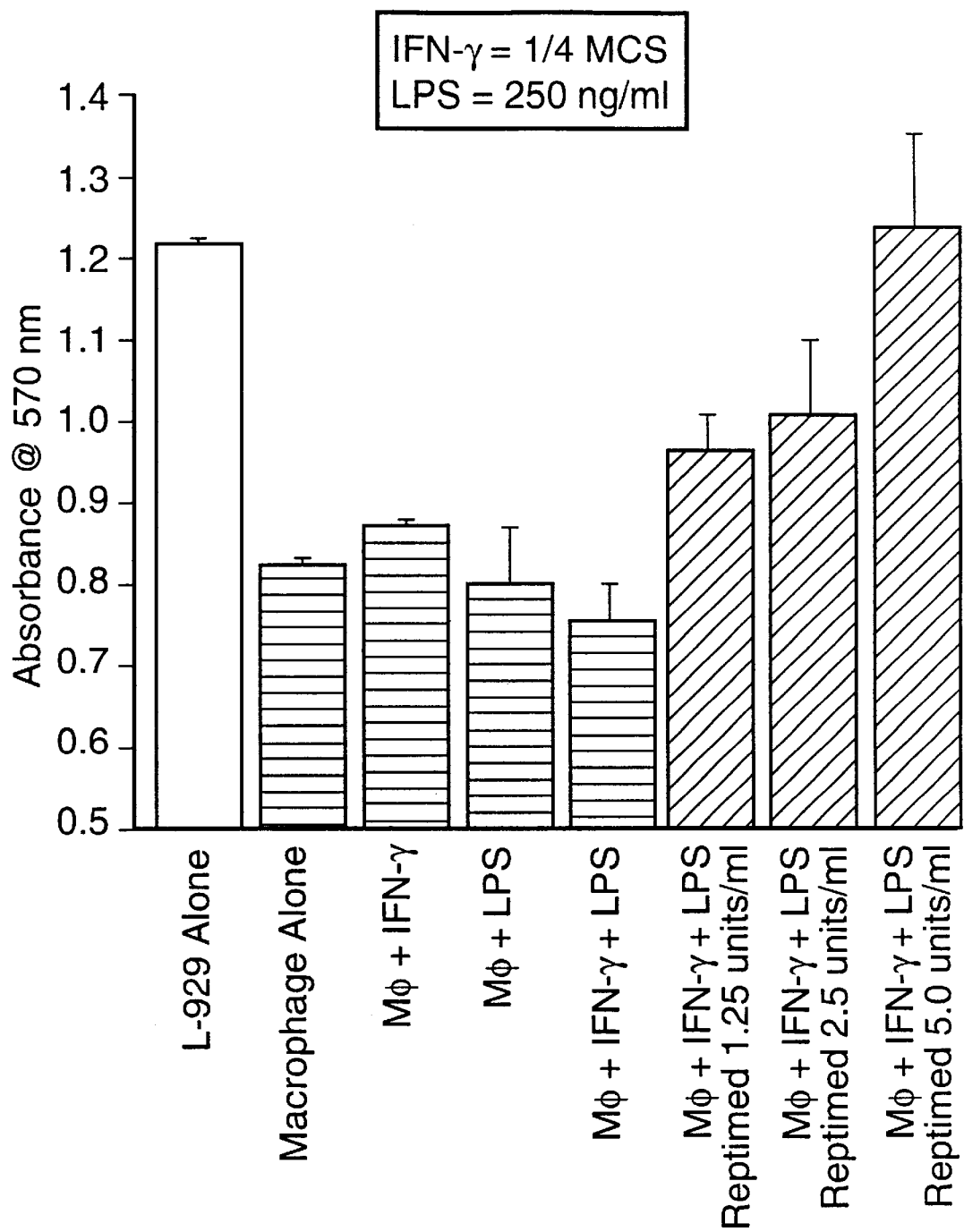
FIG. 27 shows the suppression of macrophage TNF-α production by Reptimed in a L-929 cytotoxicity bioassay.

Reptimed-treated macrophages produced significantly less TNF-α than did the positive controls (i.e. IFN-γ primed and LPS activated). FIG. 27 shows the relative amounts of TNF-α produced by the macrophages, expressed as the cell viability of the L-929 target cells (i.e. absorbance at 570 nm), with or without priming and stimulation. It shows also the improved viability of the L-929 target cells when exposed to supernatants from macrophages primed and stimulated in the presence of Reptimed, reflecting the suppression of macrophage TNF-α production by Reptimed.

Down-regulation of TNF-α mRNA: By using the technique of reverse transcriptase-polymerase chain reaction (RT-PCR), the relative quantity of TNF-α mRNA was observed after murine peritoneal macrophages were primed with IFN-γ, activated with LPS, and incubated with or without Reptimed. Primers specific for TNF-α were utilised for amplification; as a control, primers for a housekeeping gene, glucose-6-phosphate dehydrogenase (G6PDH), were used.

Peritoneal cells were collected from mice injected 3 days previously with thioglycolate medium (10% wt/vol). The cells were washed twice and adjusted to $2 \times 10^6$ cells/ml in ice-cold HBSS and 1 ml aliquots were plated into 24-well flat bottomed microtiter plates. After a 1.5 hour incubation (37° C./5% $CO_2$) the cultures were washed vigorously four times with warm HBSS to remove nonadherent cells, the wash medium was removed, and 1 ml of assay medium either alone or containing additional reagents (e.g. IFN-γ, LPS and Reptimed) was added to the adherent monolayers. After a 12 hour incubation (37° C./5% $CO_2$) the culture supernatants were removed and 1 ml of Trizol Reagent (Gibco) were added to the wells in order to lyse the macrophages and protect the RNA. Total RNA was purified as specified by Trizol Reagent protocols supplied by Gibco/BRL. This procedure includes macrophage monolayer homogenization, phase separation, RNA precipitation, RNA wash, and redissolving the RNA in DEPC-$H_2O$. Total RNA was checked for purity by running 2 μl of RNA sample with 2 μl sample buffer and 1 μl of ethidium bromide on a 1% agarose gel, and observing the 28S, 18S, and 5S rRNA brands.

With pure RNA, a CDNA library was constructed by the process of reverse transcription as carried out with the Superscript II System (Gibco) which includes the enzyme reverse transcriptase. The cDNA synthesis reaction mixture includes oligo dT, 5×first strand buffer, 0.1 M DTT, 10 mM dNTP mix, reverse transcriptase (200 units/reaction), d$H_2O$, and purified RNA. The reaction was allowed to run for 2 hours at 42° C.

The PCR amplification of the appropriate cDNA includes a reaction mixture containing 5 μl cDNA, 1 μl forward primer, 1 μl reverse primer, 5 μl 10×PCR buffer, 1 μl 10 mM dNTP mixture, 2 μl of 50 mM $MgCl_2$, 30 μl of d$H_2O$), and 5 μl of taq polymerase (2 units/reaction). 100 μl of mineral oil was overlaid over the reaction mixture in the PCR eppendorf tubes, and the reactions were subject to 30 cycles of standard PCR in a thermal cycler. The temperatures used included a denaturing temperature of 95° C., an annealing temperature of 58° C. (specific for TNF-α and G6PDH primers), and a DNA extending temperature of 72° C. The resultant PCR products, in addition to DNA molecular weight markers from φX174 DNA (digested with Hae restriction enzyme), were run on a 1.5% agarose gel containing ethidium bromide, which is shown in FIG. 28.

The expected size of the PCR product for TNF-α was determined by the number of nucleotide bases lying within the forward and reverse primers on the specific genetic sequence. The expected PCR product for TNF-α for these primers is 500 bases which is what is observed in the gel as the TNF-α band lies just below the 603 band from the DNA marker lane.

Figure 28:
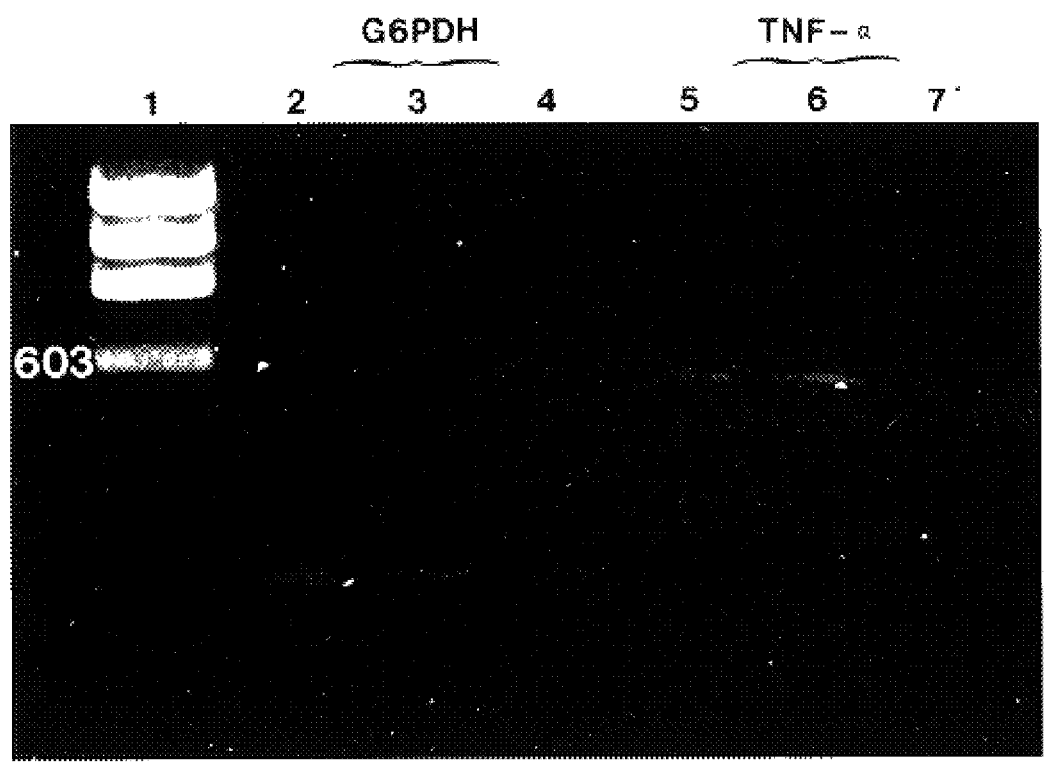
FIG. 28 shows the suppression of TNF-α mRNA in activated murine peritoneal macrophages by Reptimed. PCR products were run on a 1.5% agarose gel. Lane #1: DNA markers from φX174 DNA. Lanes 2–4 were primed for G6PDH and were from the following culture conditions: Lane 2=Macrophages ($2.5 \times 10^6$/well) alone; Lane 3=Macrophages+10% MCS (IFN-γ source)+LPS (100 ng/ml); Lane 4=Macrophages+10% MCS+LPS (100 ng/ml) +Reptimed (3 units/ml). Lanes 5–7 were primed for TNF-α and were from the following culture conditions: Lane 5=Macrophages ($2.5 \times 10^6$/well) alone; Lane 6=Macrophages+10% MCS (IFN-γ source)+LPS (100 ng/ml); Lane 7=Macrophages+10% MCS+LPS (100 ng/ml)+Reptimed (3 units/ml).

The results indicate that Reptimed does not regulate housekeeping gene mRNA levels (FIG. 28, lane 4) but does have a pronounced suppressive effect on TNF-α mRNA levels in activated murine macrophages (FIG. 28, lane 7).

EXAMPLE 10
Production of Reptimed by Cell Population Enriched for ER-MP12+ Myeloid Progenitor Cells ER-MP12 is an antibody developed against cell surface antigens on cloned early mouse myeloid progenitor cells. To obtain significant numbers of purified ER-MP12+ BM cells, use was made of magnetic Dynabeads coupled to a goat anti-rat IgG (Dynal, Oslo, Norway) which was further bound to the ER-MP12 antibody (Cedarlane/BMA). The ER-MP12 antibody was incubated with the Dynabeads coated with the goat anti-rat IgG, at a ratio of 2 µg ER-MP12/1 mg beads, overnight at 4° C. in a plastic 5 ml test tube with constant mixing on a test tube rotator. Dynabeads were collected using a Dynal MPC-1 magnetic particle concentrator (Dynal, Oslo, Norway) and washed 4 times by suspending the immunomagnetic beads in 4 ml cold HBSS supplemented with 1% bovine serum albumin for 30 minutes at 4° C.

Mouse (C57Gl/6) bone marrow (BM) cells were Percoll fractionated and Percoll fractions 2 and 3 were combined. A portion of this combined fraction was mixed with the ER-MP12 immunomagnetic beads at a ratio of 3 beads/BM cells in a plastic 15 ml screw top tube and gently mixed in a test tube rotator for 30 minutes at 4° C. A portion of the combined fraction was retained for measurement of control Reptimed production (FIG. 29: unfractionated).

Beads and ER-MP12+ BM cells were then isolated from ER-MP12- cells using the MPC-1 and washing 3 times with cold HBSS/1% BSA. Following shedding from beads over 24 hours, ER-MP12+ and ER-MP12- BM cells were separately collected by centrifugation at 1500 rpm for 10 minutes, resuspended in HBSS and viable cells counted using trypan blue exclusion. Purified cell populations were immediately cultured as described in Example 1 in serum free HBSS, supernatants were collected every 24 hours,for 3 days and each sample was purified by $C_{18}$ cartridge and P-2 gel filtration and tested for Reptimed activity in the WEHI-3 assay described in Example 1 ($1 \times 10^4$ WEHI-3 cells/well). Combined Percoll fractions 2 and 3 (unfractionated) were used as control.

Units of activity, representing the dilution of Reptimed added to give 50% suppression of WEH1-3 proliferation, was calculated from the linear regression of the dilution curves. Control proliferation of WEH1-3 cells was 14633±6504.2 CPM. ER-MP12+ at 24, 48, 72 & 96 h, p<0.01; ER-MP12- at 24 h, p<0.05.

Figure 29:
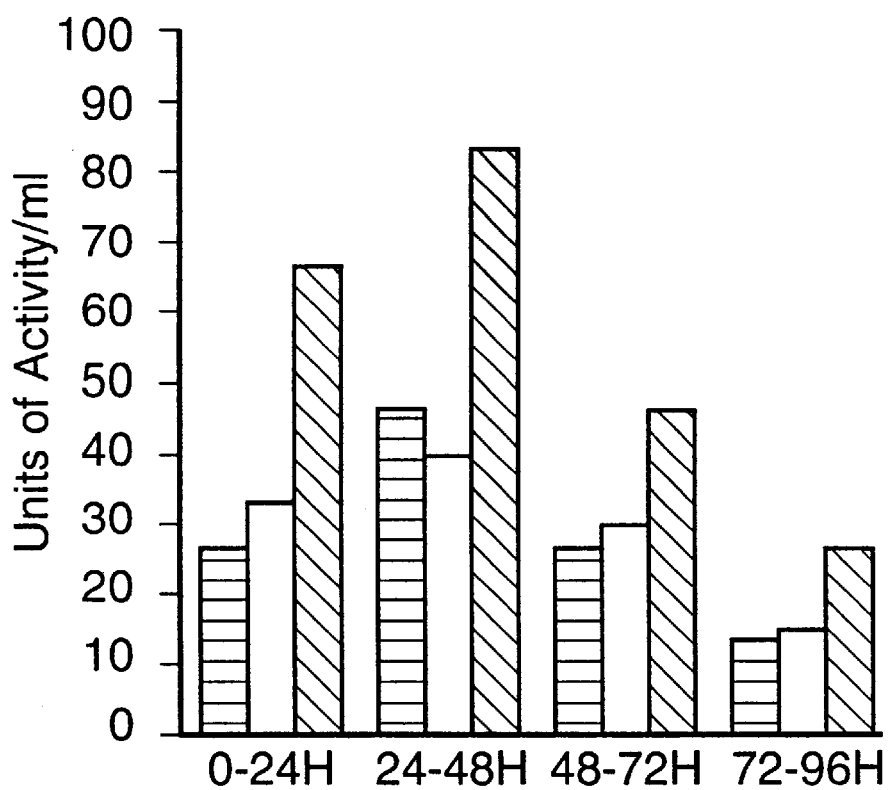
FIG. 29 shows production of Reptimed (expressed,as units of activity/ml culture medium) by control cells (Percoll separated fraction of C57Bl/6 BM cells):solid bars; by ER-MP12$^+$ fraction of control cells: diagonal hatching and by ER-MP12$^-$ fraction of control cells: open bars, over time periods shown on X axis.

As shown in FIG. 29, Reptimed production was increased in the ER-MP12+ BM cell fraction over each of the 24 hour periods, relative to ER-MP12 cells and the unfractionated cells.

EXAMPLE 11
IL-3 Stimulates the Production of Reptimed

Figure 30:
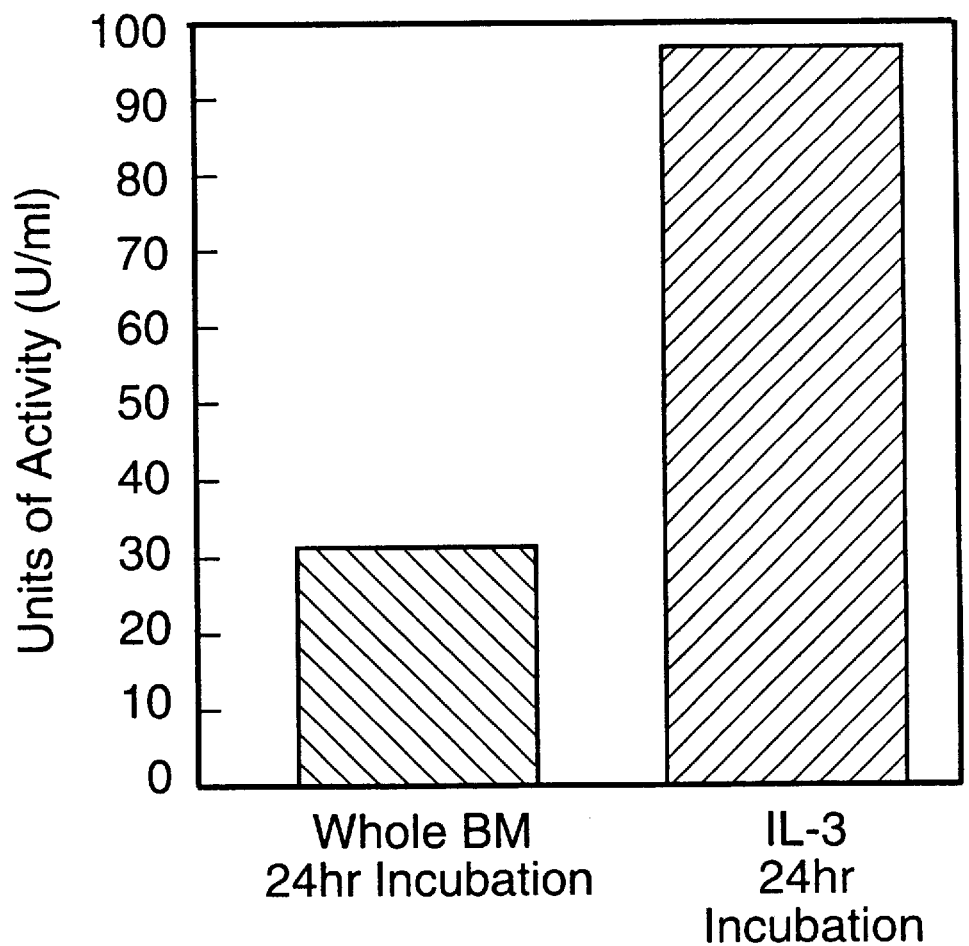
FIG. 30 shows Reptimed production (expressed as units of activity/ml) of C57Bl/6 BM cells after culture in the presence of 10% WEHI-3 CM cells (solid bar) or in the presence of RPMI (hatched bar) for 24 hours.

Murine (C57B1/6) BM cells ($1 \times 10^7$ cells/ml) were cultured for 24 hours with 10% WEHI-3 CM cells in complete RPMI culture medium or with RPMI medium alone, washed 3 times with HBSS and cultured as described in Example 1 for an additional 48 hours. Supernatants were collected every 24 hours and pooled before purification. Production of Reptimed was tested in the WEHI-3 proliferation assay. As seen in FIG. 30, culture cells stimulated Reptimed production over control levels. Units of activity, representing the number of cells etc. (see legend of FIG. 30) and showed significantly increased with WEHI-3 CM cells (FIG. 30). This correlates well with the data showing that Reptimed is produced by ER-MP12+early myeloid progenitors. IL-3 is an early acting cytokine which is known to stimulate proliferation of early myeloid progenitors.

EXAMPLE 12
Suppression of Cell Surface MAb-stimulated T Cell Proliferation by Reptimed Human peripheral blood lymphocytes (PBL) were purified to enrich for T cells by application to a 5 g nylon wool column. Non-adherent cells were eluted by washing the column with 40 ml HBSS at 37° C. Eluted cells were washed, then resuspended in complete medium and cultured at a concentration of $1 \times 10^6$ cells/ml in 96-well flat-bottom plates (Nunc,Denmark). Mouse MAbs used were against human cell surface antigens. The concentration required for maximal stimulation in tissue culture was predetermined. MAbs were added to a final concentration of: 12F6 (αCD3) 1 µg/ml, 7G5 (αCD7) 2 µg/ml and MT3 (αCD45) 1.5 µg/ml. TPA (Sigma, St. Louis, Mo.) was added at a final concentration of 20 ng/ml. All MAb stimulated cultures, except αCD3, were cultured for 5 days including a 6 h pulse with [$^3$H] thymidine (0.5 µCi/well). Experiments using aCD3 MAb were completed with Ficoll-paque isolated PBLs without the addition of TPA. These cells were cultured for 3 days including a 6 h pulse with [$^3$H] thymidine.

Parallel cultures were incubated in the absence or presence of 5×rat Reptimed. Addition of TPA alone was used as negative control.

Figure 31A:
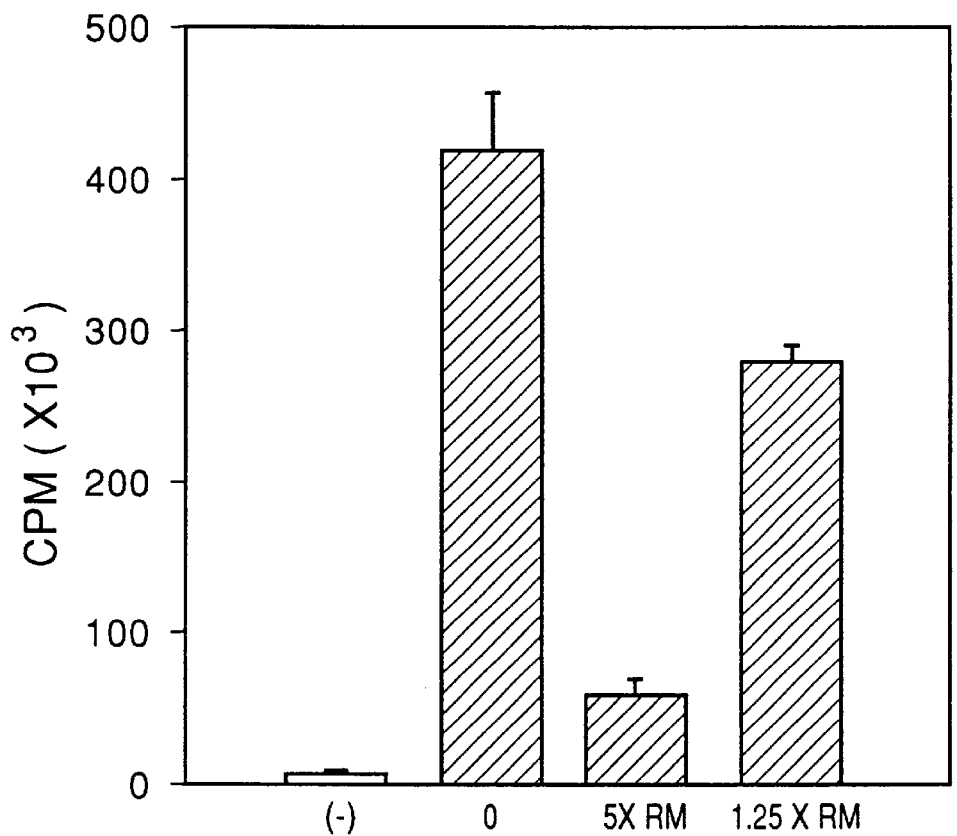
FIG. 31A shows inhibition of αCD3 antibody-induced T cell proliferation by Reptimed (αCD3: 1.0 μg/ml).
Figure 31B:
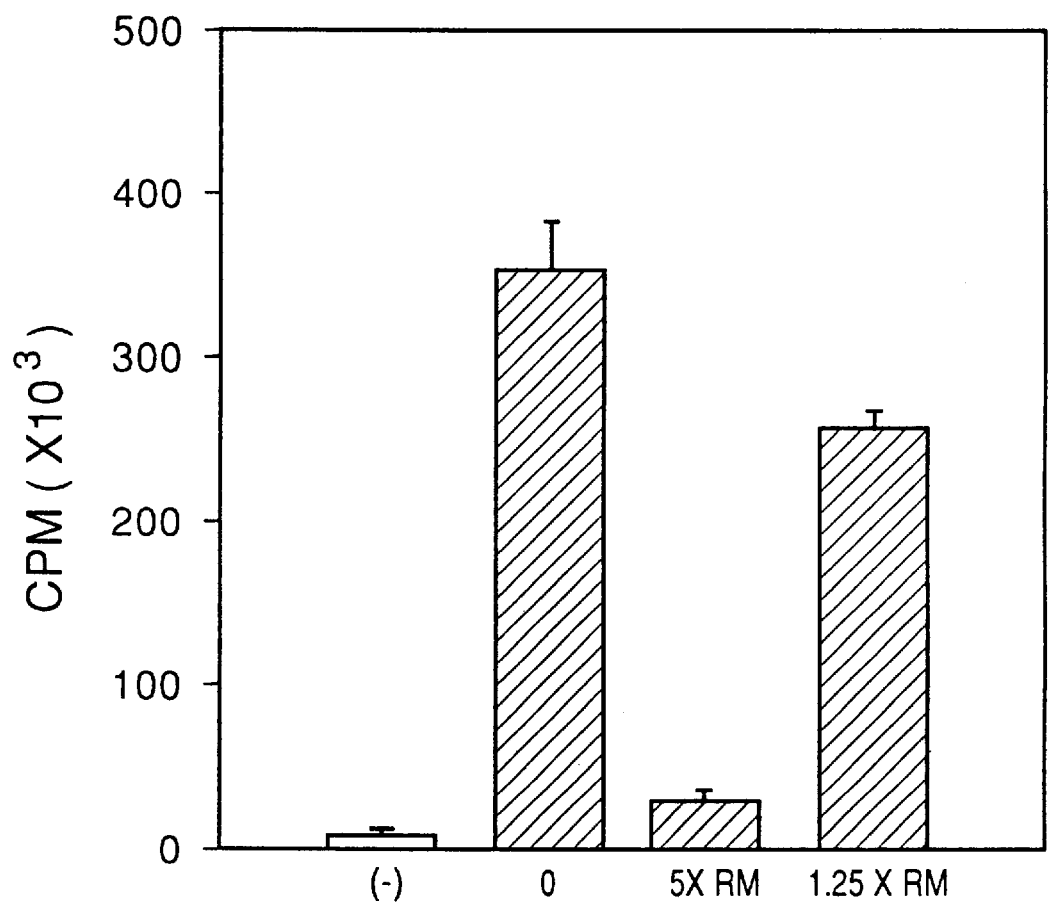
FIG. 31B shows inhibition of αCD7 antibody-induced T cell proliferation by Reptimed (αCD7: 2 μg/ml).
Figure 31C:
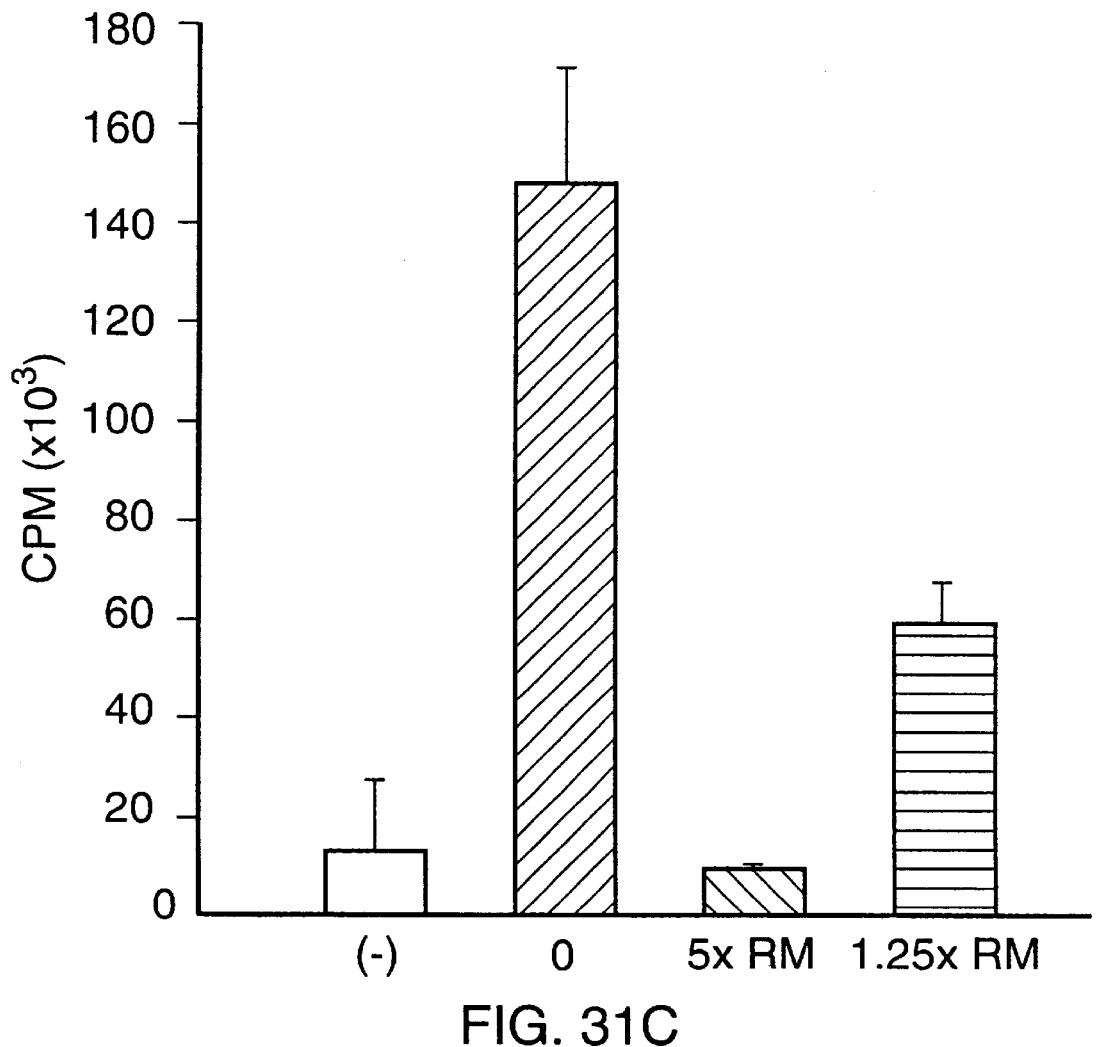
FIG. 31C shows inhibition of αCD45 antibody-induced T cell proliferation by Reptimed (αCD45: 1.5 μg/ml).

FIGS. 31A to 31C show that Reptimed was able to suppress cell proliferation induced by all three MAbs in a dose dependent manner.

EXAMPLE 13
Suppression of Myelin Basic Protein (MBP) Specific Lymph Node T Cells MBP was dissolved in saline and emulsified in an equal volume of complete Freunds adjuvant (Difco Laboratories, Detroit, Mich.) supplemented with 600 µg/ml of *Mycobacterium tuberculosis* H37RA (Difco). Six- to 10-week-old female SJL/J mice were injected subcutaneously with a total volume of 0.1 ml containing 400 µg MBP and 30 µg *M.tuberculosis* distributed over four sites draining into the inguinal and axillary lymph nodes. Ten to 12 days later the draining lymph nodes were aseptically removed and processed into a single cell suspension. Lymph node cells were cultured at $4 \times 10^5$ cells/ml and, transferred to 96 well flat-bottom plates (Nunc, Denmark). MBP was added to a final concentration of 50 µg/ml. The cell cultures were incubated at 37° C. for 72 h and various concentrations of C18-cartridge purified rat Reptimed were added at Day 0, Day 1 or Day 2. Cultures were pulsed for 12 h with 0.5 µCi/well [$^3$H] thymidine (ICN, Mississauga, Ontario) and harvested onto glass fibre filter paper on an automatic 96-well harvester (Tomtec 96) and counted on a Microbeta 1450 liquid scintillation counter (LKB/Wallac) using an IBM PS/2 model 30 286 computer.

Figure 32:
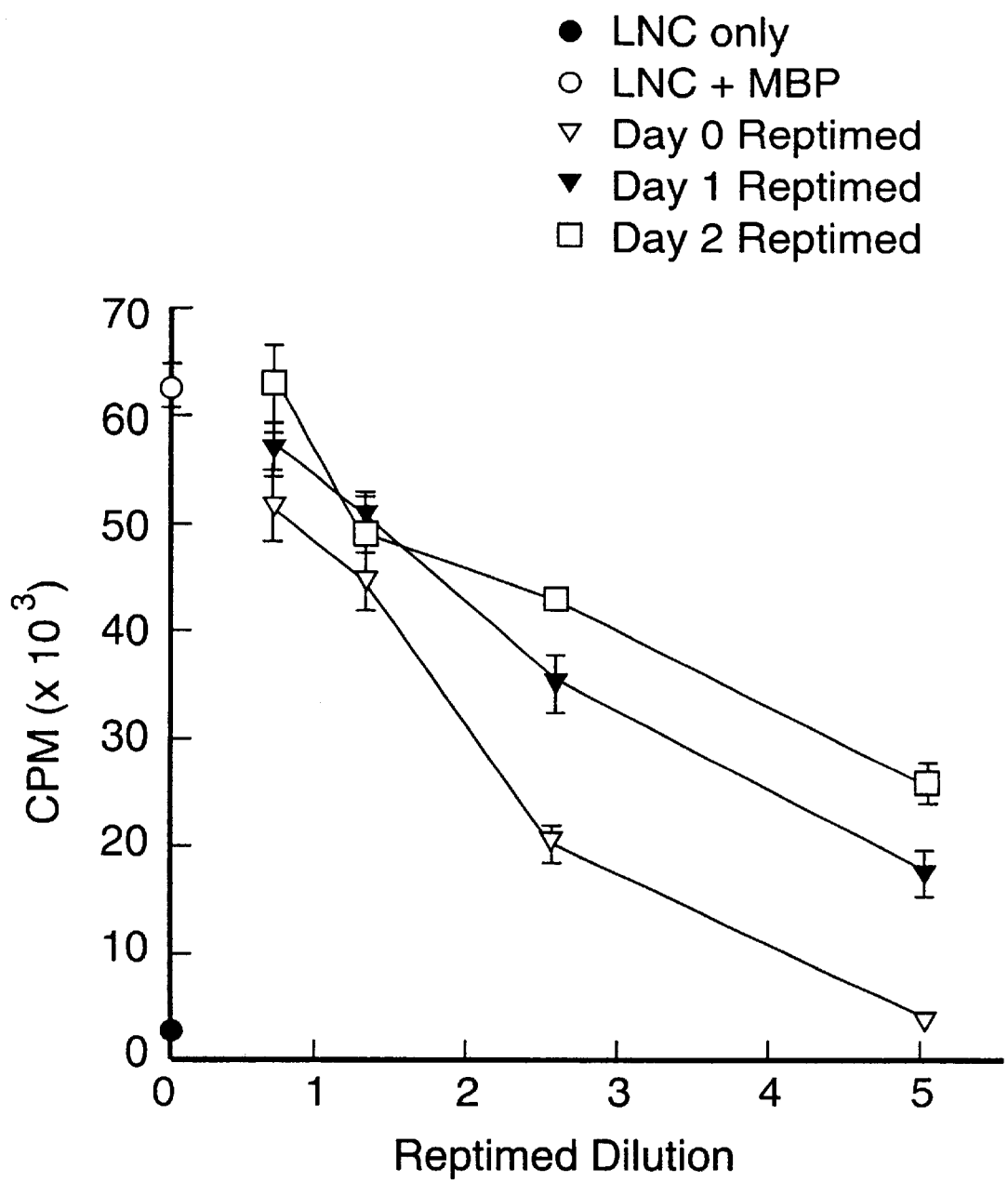
FIG. 32 shows the inhibition of MBP-stimulated lymph node cell proliferation by Reptimed: ● is level of proliferation of control unstimulated cultures; O is level of proliferation in response to 50 μg/ml MBP. Parallel cultures were treated with various concentrations of Reptimed (x axis) from Day 0 (▽), Day 1 (▼) or Day 2 (□). Proliferation was measured on Day 3 by $^3$H thymidine uptake, expressed as CpMx10$^3$ (Y axis). Vertical bars represent standard deviation.

Antigen specific proliferation was inhibited most drastically when Reptimed was added at Day 0 (time 0) of the cell culture as shown in FIG. 32. Addition at Day 1 (24 h) and Day 2 (48 h) was also able to inhibit [$^3$H] thymidine uptake, but to a lesser extent.

EXAMPLE 14

Reptimed Prevents Cells From Entering G0 to S Phase of the Cell Cycle.

Figure 33:
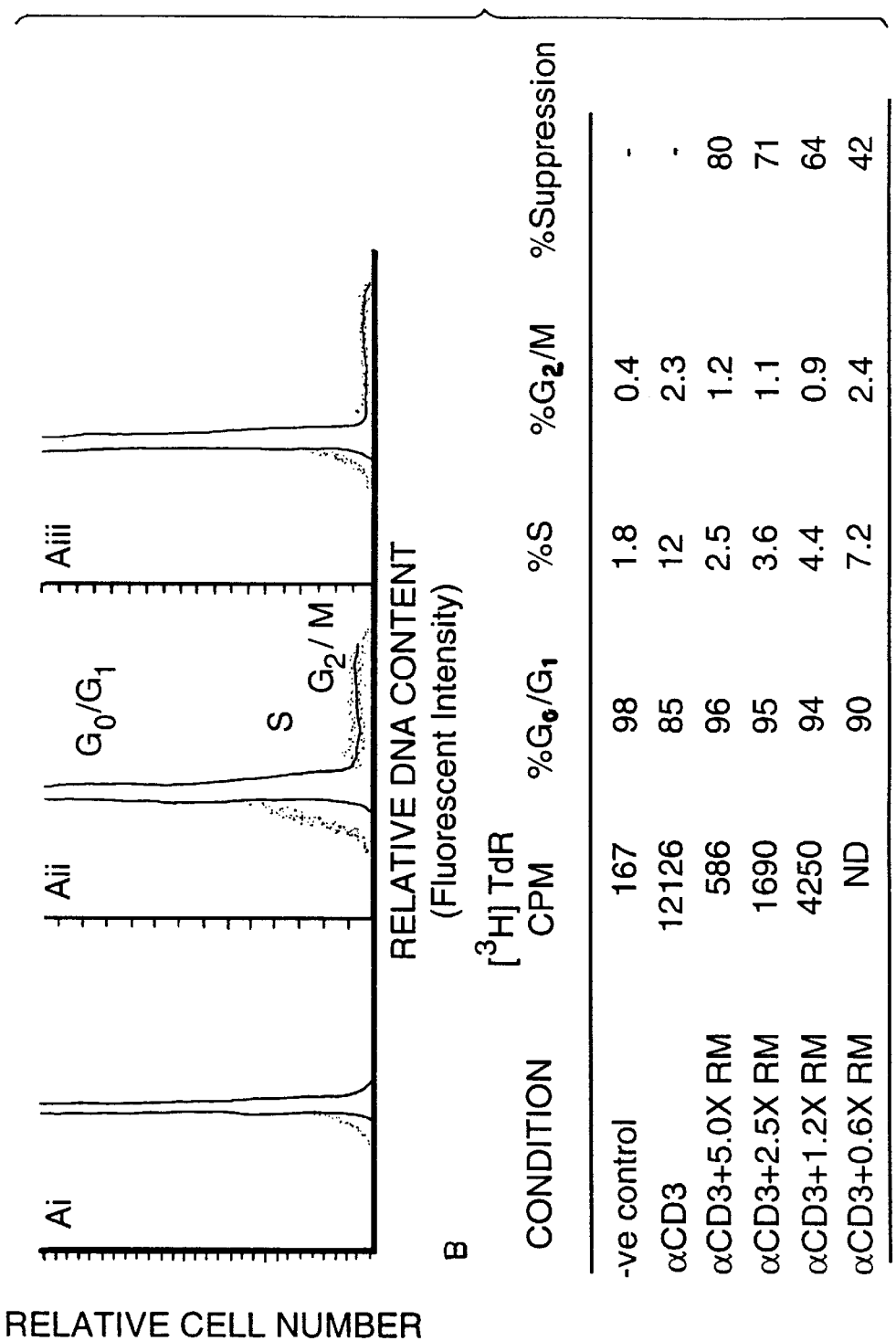
FIG. 33 shows the effect of Reptimed on the cell cycle: Panel A shows a single peak which represents unstimulated PBLs which are in the G0/G1 phase of the cell cycle (Ai) and PBLs stimulated with aCD3 (1 μg/ml) in the absence (Aii) and presence (Aiii) of 5×Reptimed; Panel B shows cell proliferation, expressed as CPM $^3$H thymidine uptake and percentages of cell cycle segments.

Human PBLs were isolated and cultured at $1\times10^6$ cells/ml in 12×75 mm sterile tubes (Falcon) for 72 h. Cells were resuspended and transferred (100 µl/well) in duplicate, to 96-well flat-bottom plates. Fresh complete medium (100 µl) containing 0.5 µCi [$^3$H] thymidine was added to each well for 6 h before harvesting to determine simultaneous [$^3$H] thymidine incorporation. The remaining 800 µl of cells were transferred to non-sterile 5 ml (12×75 mm) polypropylene FACS tubes (Diamed). Cold PBS (pH 7.2; Sigma) was added to each tube to wash the cells. Cells were resuspended in 875 µl of cold PBS gently. Then 125 µl of cold 2% paraformaldehyde (BDH Inc.) was added and the mixture was vortexed immediately. Cells were incubated on ice for 1 h, then washed and resuspended in 1 ml of 0.2% Tween 20 (Sigma) in PBS. After a 15 min incubation (37° C.), cells were washed in cold PBS. Cells were resuspended in 600 µl of cold propidium iodide solution (10 µg/ml propidium iodide (Calbiochem), 11.25 K units RNAse (0.89 U/ml) (Boehringer Mannheim)). The cells were incubated for a minimum of 30 min on ice in the dark. Analysis was performed using a FACSCAN (Becton Dickinson, Mississauga, Ontario), employing LYSYS software for running the cells and CELLFIT for cell cycle analysis. The results are shown in FIG. 33. Panel 33A: αCD3 MAb stimulated PBLs were cultured at $1\times10^6$ cells/ml for 72 h. Cells were fixed with 0.25% paraformaldehyde, permeabilized in 0.2% Tween 20, then incubated with propidium iodide solution containing RNAse. Panel Ai: unstimulated PBLS; Aii: αCD3 (1 µg/ml) stimulated; Aiii: αCD3+5× Reptimed treated cells. Panel B: Simultaneous [$^3$H]TdR uptake (72 h with 6 h pulse) and percentages of cell cycle segments. Relative percentages of cells in each segment of cycle were calculated using CELLFIT software. Percent suppression of cells in S phase were calculated comparing Reptimed treated cells to αCD3+ve controls. These two sets of data are described together since [$^3$H]TdR uptake occurs in the S phase of the cell cycle. Thus, a decrease in [$^3$H]TdR uptake signifies a decrease in S phase activity of the PBLs which supports the cell cycle data.

$G_0$ is the term used to designate a cell in resting state. After stimulation the time to traverse from $G_0$ through to S (synthesis) phase is short. Cells in culture however proliferate at a rate dependent on the fraction of cells in cycle, rather than the cycling time which is of constant duration. CELLFIT software (Becton Dickinson) calculates the number of cells analyzed in $G_0/G_1$ (2N complement of DNA), S phase (>2N, <4N) and $G_2/M$ (4N DNA). FIG. 33A reveals the fact that resting lymphocytes have very few cells in cycle (>2N). The vast majority of cells in these cultures were in $G_0$ phase (98%). However after stimulation with αCD3 (1 µg/ml), 15% of the cells were cycling at 72 h. Reptimed was found to prevent cells from entering the S phase in a dose-dependent manner. Treatment with the highest concentration of Reptimed caused an 80% reduction of cells entering the S phase as compared with the untreated control.

Simultaneous [$^3$]TdR uptake data was also obtained in these experiments and is shown in FIG. 33B. The results are identical to the experiments in which the cell cycle was measured. That is, the higher the concentration of Reptimed, the fewer cells in cycle and hence the less [$^3$H]TdR uptake observed. FIG. 33A(iii) demonstrates that Reptimed-treated cells have noticeably fewer cells in S and $G_2$+M phases as compared to the positive control (FIG. 33Aii).

EXAMPLE 15

Downregulation of CD45 Phosphatass in Stimulated Thymocytes.

Methods: The enzymatic activity of CD45 was assayed in Balbic thymocytes. Thymuses were isolated from 6–10 week old Balb/c mice and processed into a single cell suspension with 5 ml PBS (pH 7.2; Sigma). Thymocytes were cultured at $1\times10^7$ cells/ml and transferred (1 ml/well) to 24 well-flatbottom plates (Nunc Plastics, Roskilde, Denmark). The cells were stimulated with 2.5 µg/ml Con A (ICN Immunobiologicals, Lisle, Ill.) with or without 5×rat Reptimed (C18-cartridge purified). Control cells were treated with 500 ng/ml lonomycin (Calbiochem, La Jolla, Calif.). After a 10 min incubation (37 C), cells were washed in PBS and lysed with NP-40 lysis buffer (150 mM NaCl, 50 mM Hepes;pH 7.2, 2 mM EDTA, 2 mM PMSF, 10 µg/ml Leupeptin, 0.5% NP-40 detergent). RNA and DNA were removed by centrifuging cell lysate at 13K rpm for 15 min. Supernatant was transferred to 1.7 ml micro-centrifuge tubes (Diamed, Mississauga, Ontario) and precleared with 40 µl/tube of 50% goat α-rat IgG bound agarose beads (Sigma #6592, St. Louis Md.). After 20 min incubation (4° C. rotating), suspension was centrifuged at 13K rpm for 6–8 secs and supernatant was transferred to 1.7 ml tubes containing 20 µl of αCD45 conjugated goat α-rat IgG bound agarose beads. After 45 min incubation (4° C. rotating) suspension was centrifuged at 13K rpm for 6–8 secs and washed 3× with resuspension buffer (150 mM NaCl, 50 mM Hepes; pH 7.2, 2 mM EDTA, 2 mM PMSF, 10 µg/ml leupeptin, 1 mM dithreithiotol (DTT). To each tube containing 20 µl immunoprecipitated CD45 bound agarose beads, 360 µl phosphatase buffer (100 mM Hepes;pH 7.2, 5 mM EDTA, 125 mM DTT) was added. After a 10 min incubation (37 C), 20 µl of (20 mg/ml) p-nitrophenyl phosphate (PNPP) was added to each tube and allowed to incubate for 10 min in a 37 C waterbath. Equal volume 5M NaOH was added to each tube and 100 µl samples were transferred to 96-well flatbottom plates (Nunc). Optical density was measured at 405 nm on Titertek Multiskan spectrophotometer (Flow Laboratories, Mississauga, Ontario).

Figure 34:
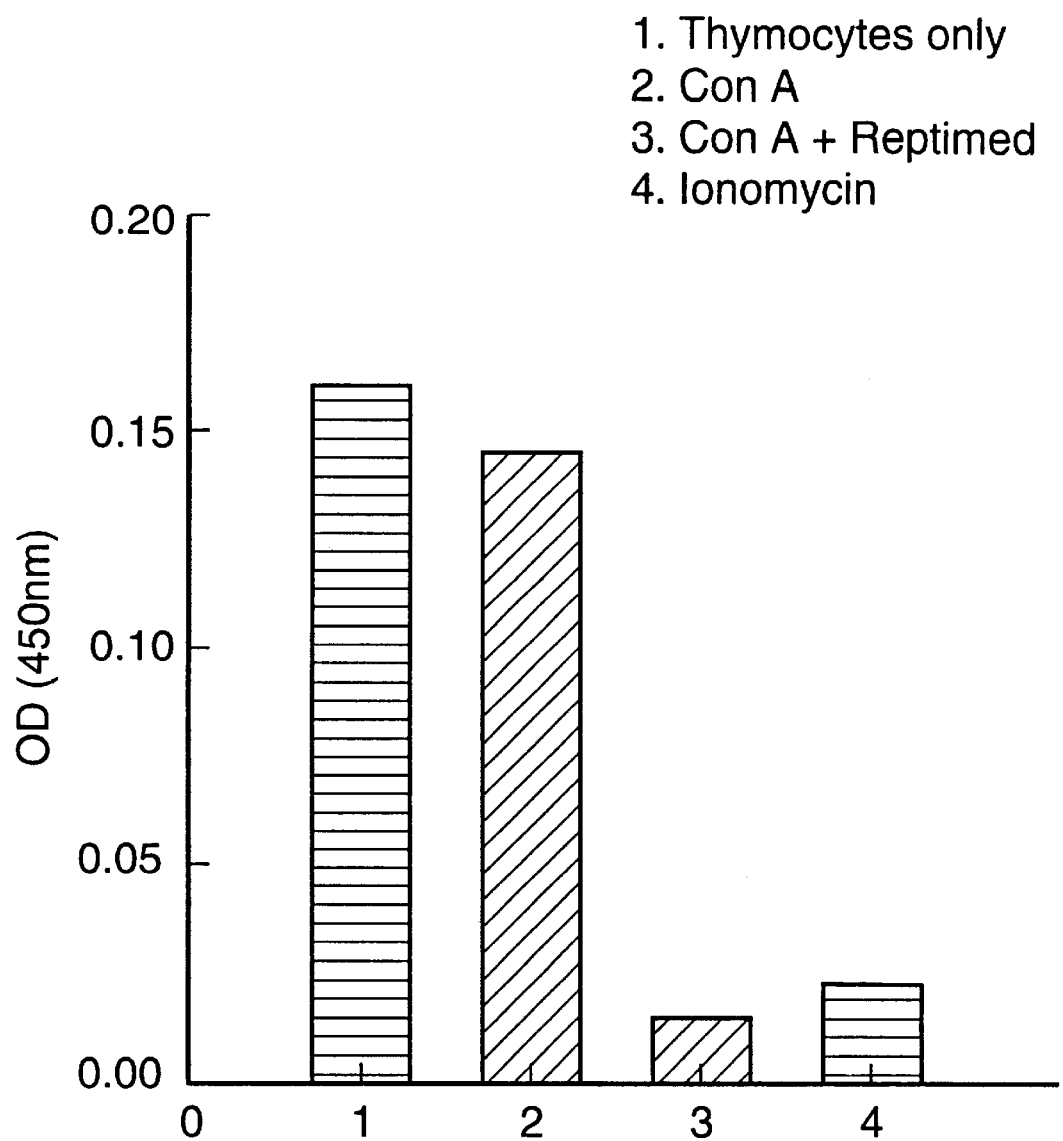
FIG. 34 shows inhibition of CD45 phosphatase activity by Reptimed: Thymocytes were (1) incubated without stimulating agent; or were (2) stimulated with 2.5 μg/ml Con A only ; (3) with Con A plus Reptimed (5×) or (4) with 500 ng/ml ionomycin only. This data is representative of 12 repeated experiments. p value obtained using ANOVA was <0.001.

FIG. 34 shows that treatment of stimulated thymocytes with Reptimed dramatically reduced phosphatase activity of CD45 by up to 80%. The inhibition of the enzymatic activity of CD45 by Reptimed was similar to levels of inhibition achieved by ionomycin control, a known downregulator of CD45 phosphatase.

EXAMPLE 16

Tyrosine Phosphorylation

Figure 35A:
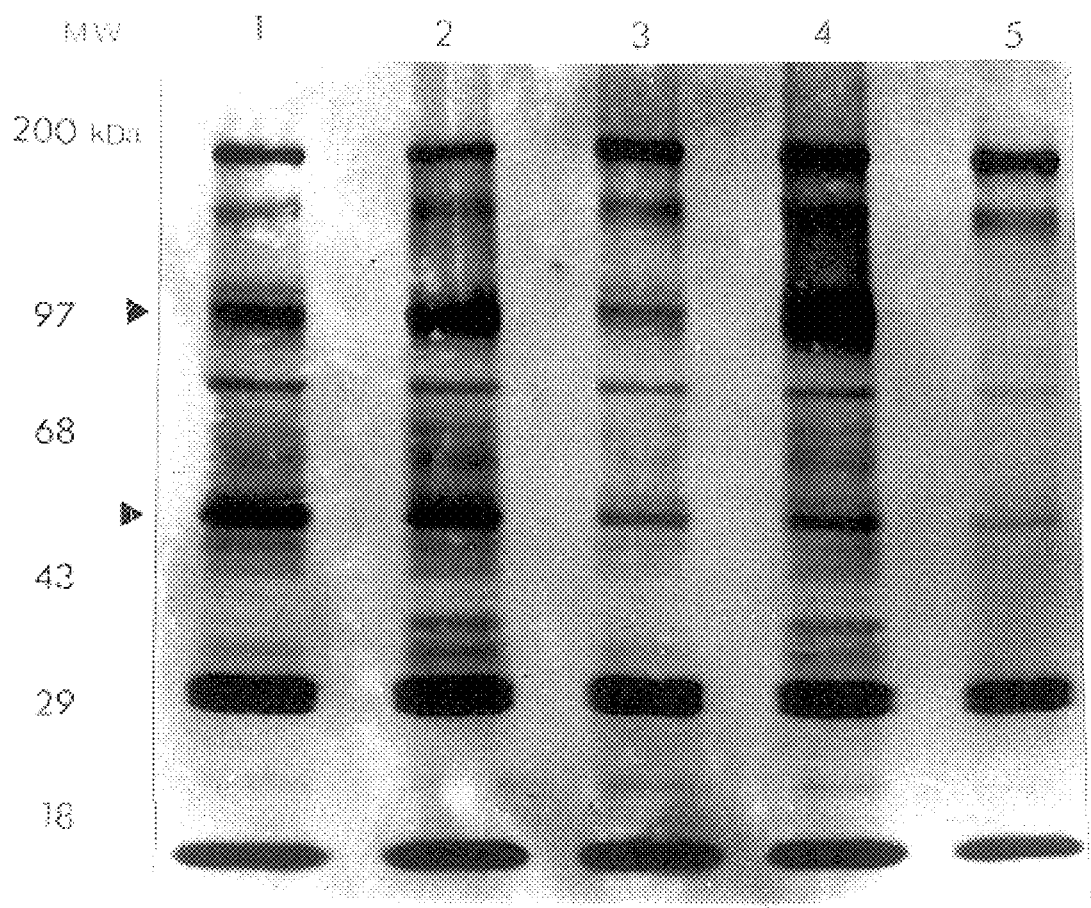
FIG. 35A shows tyrosine phosphorylation of unstimulated Balb/c thymocytes (Lane 1); Balb/c thymocytes stimulated with 2.5 μg/ml Con A (Lane 2); treated with 5×Rat Reptimed (Lane 3); 2.5 μg/ml Con A plus 5×Reptimed (Lane 4); or 500 ng/ml ionomycin only (Lane 5).

Balb/c thymocytes (FIG. 35A) or murine T cell hybridoma A1.1 cells (FIGS. 35B and C) cultured at $5\times10^6$ cells/well were preincubated with either 5× or 0.63×rat C18 purified Reptimed for 1 hour prior to stimulation. Balb/c thymocytes were stimulated with 2.5 µg/ml Con A, while A1.1 cells were stimulated with purified anti-cell surface MAb 2C11 (α CD3) (FIG. 35B: 2 µg/ml; FIG. 35C: 5 µg/ml). After a 10 min. stimulation at 37° C., cells were lysed with SDS, centrifuged at 90000 rpm to remove DNA and RNA and the proteins were precipitated using acetone. The acetone was then blown off and the proteins were lyophilized. The proteins were run on a 5–17% gradient gel and then transferred to PVDF (Immibilon P) membrane. The PVDF membrane was checked for protein transfer using Ponceau S and then was blocked using evaporated milk (Carnation brand). The membrane was washed and probed using an aphosphotyrosine MAb, 4G10, and then treated with horse radish peroxidase conjugated IgG 2b. Enhanced chemiluminescence was used for autoradiography.

Figure 35B:
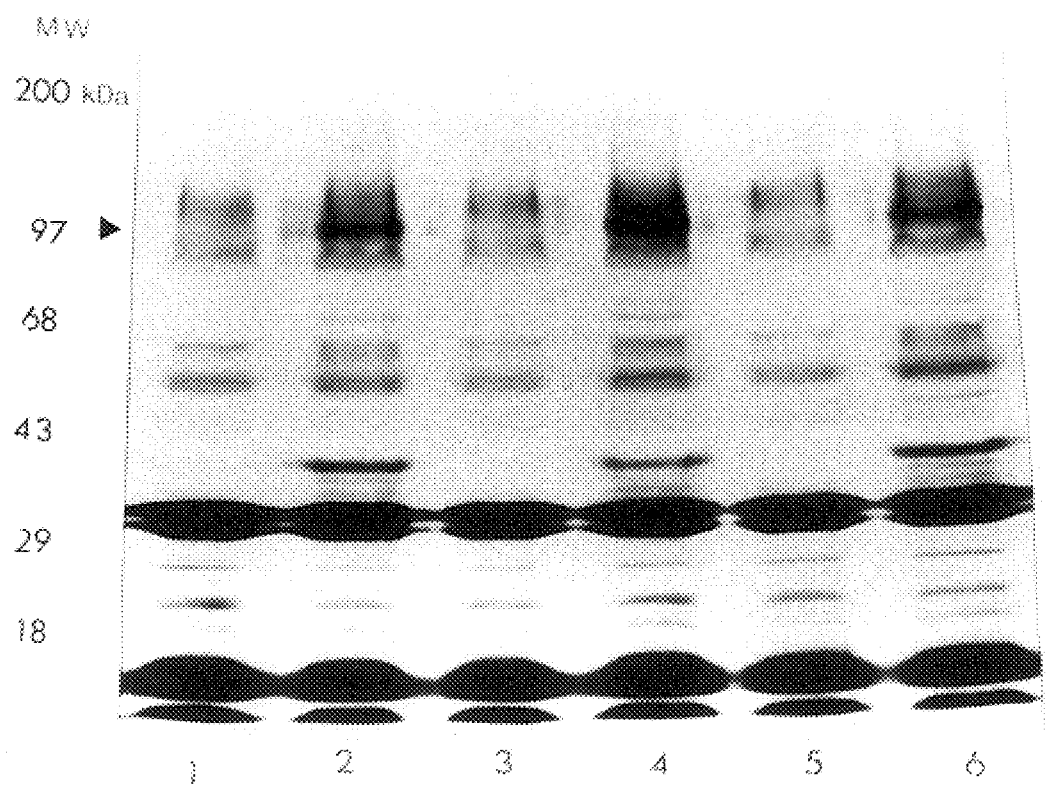
FIG. 35B shows tyrosine phosphorylation of unstimulated A1.1 cells (mouse T cell hybridoma) (Lane 1); A1.1 cells stimulated with 2 μg/ml αCD3 MAb (Lane 2), treated with 5×Rat Reptimed alone (Lane 3), treated with 2 μg/ml αCD3 plus 5×Reptimed (Lane 4), or with 0.63×Reptimed only (Lane 5) or 2 μg/ml αCD3 plus 0.63×Reptimed (Lane 6).
Figure 35C:
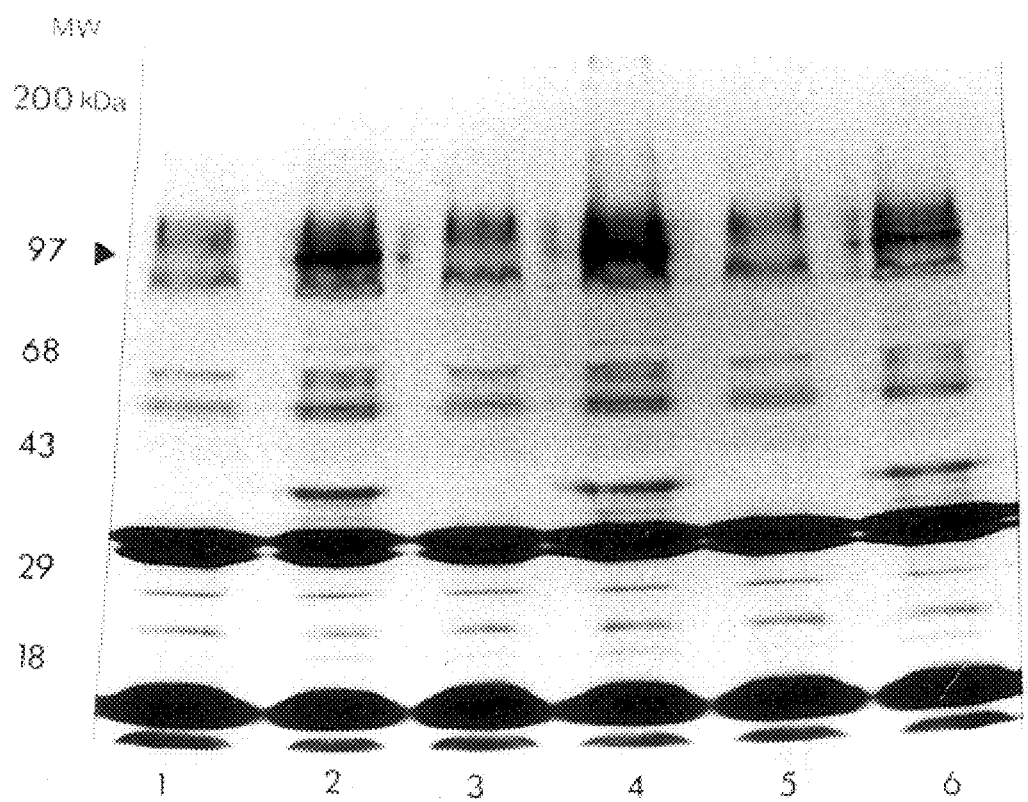
FIG. 35C shows tyrosine phosphorylation of unstimulated A1.1 cells (mouse T cell hybridoma) (Lane 1); A1.1 cells stimulated with 5 μg/ml αCD3 MAb (Lane 2); treated with 5×Rat Reptimed alone (Lane 3); treated with 5 μg/ml αCD3 plus 5×Reptimed (Lane 4); or 0.63×Reptimed only (Lane 5); or 5 μg/ml aCD3 plus 0.63×Reptimed (Lane 6).

The highest dose of Reptimed produced a hyperphosphorylation of a 95–105 molecular weight species in both Balb/c thymocytes (FIG. 35A) and A1.1 cells FIGS. 35B and C). In Balb/c thymocytes, Reptimed was also able to produce a dephosphorylation of a 55–60 MW species. As the dose of Reptimed was diluted, the phosphorylation state of these proteins returned to levels similar to the control.

EXAMPLE 17

The Effect of Reptimed on Na—K—Cl Cotransport and cAMP-dependent Protein Kinase Activity Reptimed Inhibits Na—K—Cl Cotransport as Measured by $^{86}$Rb Uptake Jurkat cells were centrifuged for 15 min at 300×g and resuspended in Dulbecco's modified Eagle's medium (DMEM; ionic composition: 1.8 mM $CaCl_2$, 5.4 mM KCl, 0.8 mM $MgSO_4$, 110 mM NaCl, 0.9 mM $NaH_2PO_4$, 0.25 μM $Fe(NO_3)_3$; GIBCO, Grand Island, N.Y.) with 10 mM N-2 hydroxyethylpiperazine-N'-2 ethanesulfonic acid (HEPES), pH 7.4 at a final concentration of 5–10×10$^6$ cells/ml. Cells were either untreated or treated with 5×C18 purified rat Reptimed or 1 μm isoproterenol. $^{86}$Rb was added at a concentration of 1–2 μCi/ml. Assays were stopped by aliquoting 100 μl of the reaction mixture into chilled microcentrifuge tubes prefilled with 100 Al of 3 mM $BaCl_2$ and 0.1 ImM of ouabain solution layered over 100 μl of a 3:1 of mazola oil to n-butylphthalate mixture. Cells were rapidly sedimented through the oil interface (1 min at 15,000 g). centrifuge tube tips containing the tip pellets were clipped in the vials and radioactivity was determined by scintillation spectroscopy (Beckman LS 6000).

Figure 36A:
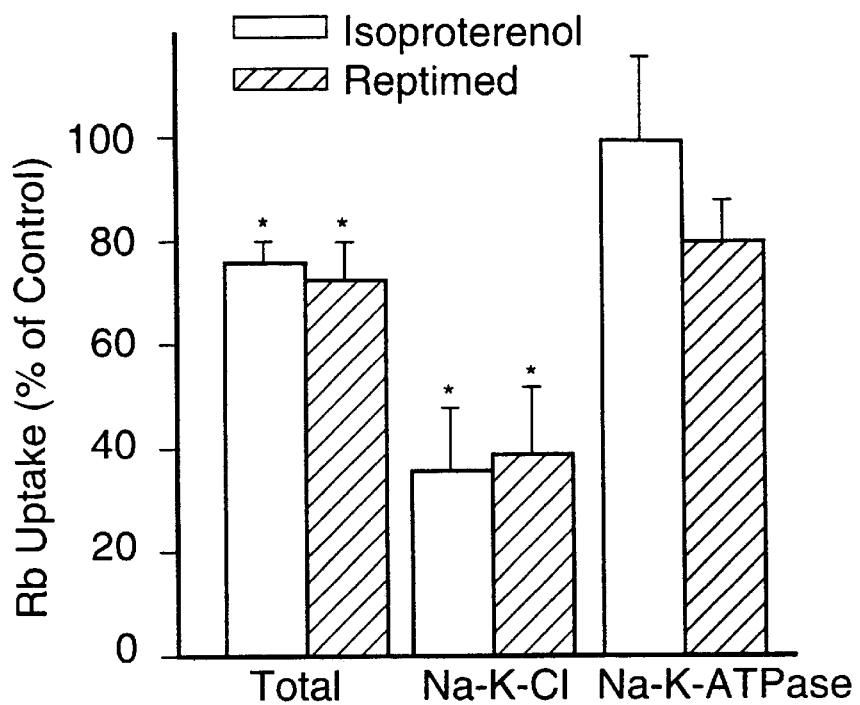
FIG. 36A shows the effect of Reptimed on total $^{86}$Rb uptake, Na—K—Cl cotransport dependent uptake, and Na—K ATPase-dependent uptake (negative control) in Jurkat cells treated with 5×Rat Reptimed (open bars) or with 1 μm isoproterenol, a known downregulator of Na—K—Cl cotransport as a positive control (hatched bars). Data represent the mean +/- sem from 6 experiments. *=p<0.05 vs. control uptake (Untreated Jurkat cells only).

FIG. 36A shows that Reptimed (hatched bar) inhibited Na—K—Cl cotransport (36+/−13% of untreated Jurkat cell control, $p<0.001$) at levels similar to isoproterenol (38+/−8% of control, $p<0.001$), a known downregulator of Na—K—Cl cotransport.

Reptimed Increases cAMP-dependent Protein Kinase Activity in Jurkat Cells

Figure 36B:
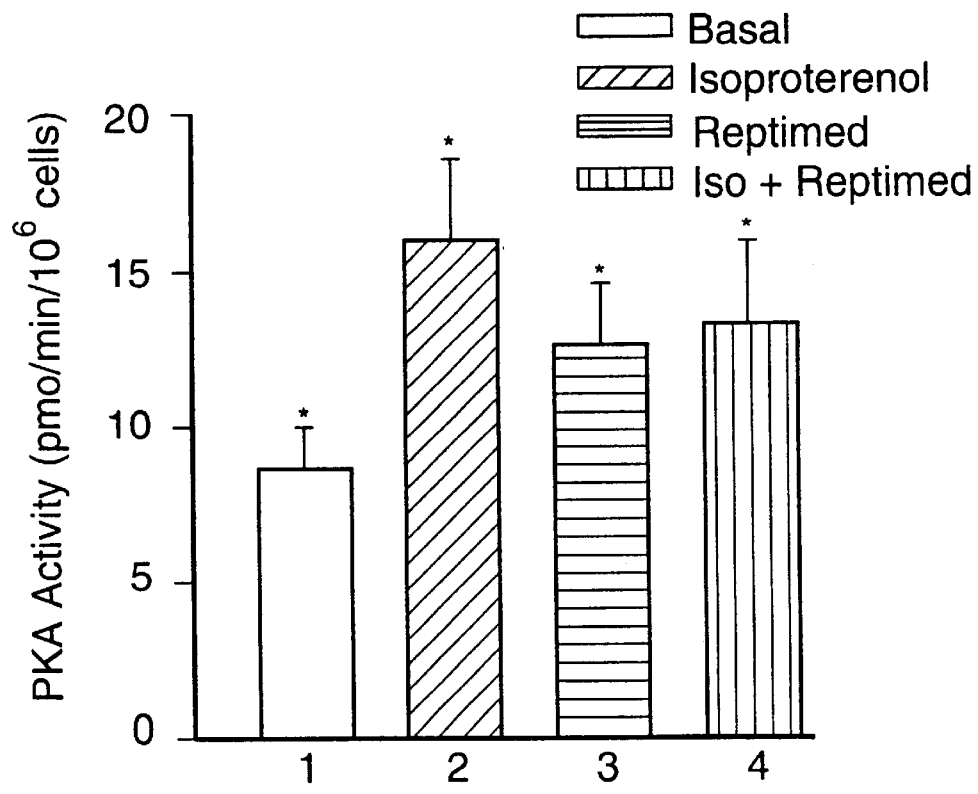
FIG. 36B shows the effect of Reptimed on cAMP-dependent protein kinase (PKA) activation in Jurkat cells expressed as pmol/min/$10^6$ cells. 1: Basal PKA activity of Jurkat cells; 2: PKA activity of isoproterenol [1 μm] treated Jurkat cells; 3: 5×Rat Reptimed treated Jurkat cells; 4: isoproterenol [1 μm] plus 5×Reptimed treated Jurkat cells.

Cyclic AMP-dependent protein kinase (PKA) activity was assayed in digitonin-permeabilized cells. Jurkat cells were centrifuged at 300×g for 15 min and resuspended in Hanks' balanced salt solution without calcium and with 0.5 mM EDTA, 1 mm magnesium sulfate, and 1 mg/100 ml digitonin. Jurkat cells were incubated for 15 min at 4° C. and then washed twice as above in Hanks' solution without digitonin and finally resuspended at a final concentration of 10 to 20×10$^6$ cells/ml for assay. Cells were either untreated, treated with 5×rat C18 purified Reptimed, or with 1 μm isoproterenol, or with both 5×Reptimed and 1 μm isoproterenol. PKA activity was assessed by the phosphorylation of the synthetic PKA substrate (Kemptide-Sigma Chemical Corporation, St. Louis, Mo.). Phosphorylated substrate was separated by adherence to phosphocellulose. After six washes in phosphoric acid, radioactivity on the phosphocellulose strips was assessed by scintillation spectroscopy. FIG. 36B shows that Reptimed produced an increase in cAMP-dependent kinase (PKA) activity similar to that product by isoproterenol, a known stimulator of PKA activity. Reptimed treatment of Jurkat cells produced a significant increase in PKA activity (basal activity=9+/−1 pmol phosphoprotein/min/10$^6$ cells, Reptimed-stimulated activity=13+/−2 pmol phosphoprotein/min/10$^6$ cells). Isoproterenol also produced a significant increase in PKA activity however co-incubation of Reptimed and isoproterenol resulted in no significant additive effect (to 14+/−2 pmol/min/10$^6$ cells).

EXAMPLE 18

Treatment of Autoimmune Disease by Reptimed in NZB/W Mice.

Female NZB/W mice were obtained from the Jackson laboratory (Bar Harbor, Me.). Four week old mice were divided into two groups, a control group and a Reptimed treatment group. On a bi-weekly basis, mice were injected intraperitoneally with either 0.2 ml of 100×C18 purified mouse Reptimed or 0.2 ml phosphate buffered saline-control. At four week intervals, groups of treated or untreated mice were sacrificed. Kidneys were used for histological analysis and spleens were used to enumerate cells capable of producing antiDNA antibodies.

Histology

Kidneys were removed from each sacrificed mouse, and thin sections were cut and fixed immediately in glutaraldehyde. The remainder of the kidneys was fixed in 10% buffered formalin. Tissue for light microscopy was processed and stained with haematoxylin-eosin and Masson's trichrome. Tissue for electron microscopy was rinsed in 0.1 cacodylate buffer and counterfixed in osmium tetroxide. Tissue was then embedded in Epon Araldite and cut into semi-thin sections, 0.5 to 1 micron thick that were stained with toluidine blue. One block with a complete glomerulus was selected for each mouse, thin-sectioned, and the 60 to 90 micron sections were stained with lead acetate and uranyl nitrate, put on 300 nw mesh grids and read on a Zeiss 109 electron microscope.

Histology Classification

Kidney samples were classified according to the WHO Kidney Histology Classification, as follows:

WHO Kidney Histology Classification

I. Normal light microscopy. Occasional mesangial hypercellularity on electron microscopy.

IIA. Early mesangial swirling on light microscopy. Mesangial swirling on electron microscopy with early mesangial dense deposits and occasional subendothelial deposit.

IIB. Some capillaries appear closed on light microscopy with obvious mesangial swirling. Electron microscopy shows swollen endothelial cells with obvious occasional subendothelial and mesangial dense deposits.

III. Some glomeruli show hypercellularity, closed loops, and mesangial thickening. Electron microscopy shows mesangial dense deposits plus mesangial thickening.

Deposits are seen in subendothelial and epimembranous locations. Pyknotic nuclei in some capillary loops. White cells and platelets seen in capillaries.

IV. Light microscopy shows fibrotic glomeruli with crescents and hypercellularity. Tubular dilatation is seen. Electron microscopy shows swollen endothelial cells and dense deposits on both sides of the basement membrane.

Anti DNA Antibody Production

Standard spleen cell cultures were maintained for 5 days before assessing their ability to produce anti-DNA antibodies. Briefly, anti-single stranded DNA (ss-DNA) antibody producing cells were assayed on glass slides in agarose. Cells were harvested and washed twice with BSS. 100 μl of cell suspension and 50 μl of a 5% solution of ssDNA coupled sheep red blood cells (SRBC) were mixed with 500 μl of a 0.5% solution of agarose (Mandel Scientific, Guelph, Ont.). Plaque forming cells (PFC) were developed at 37° C. with a 1% solution of rabbit anti-mouse Ig (Cedarlane, Hornby, Ont.) and 10% solution of Hemo-Lo guinea pig complement.

Figure 37:
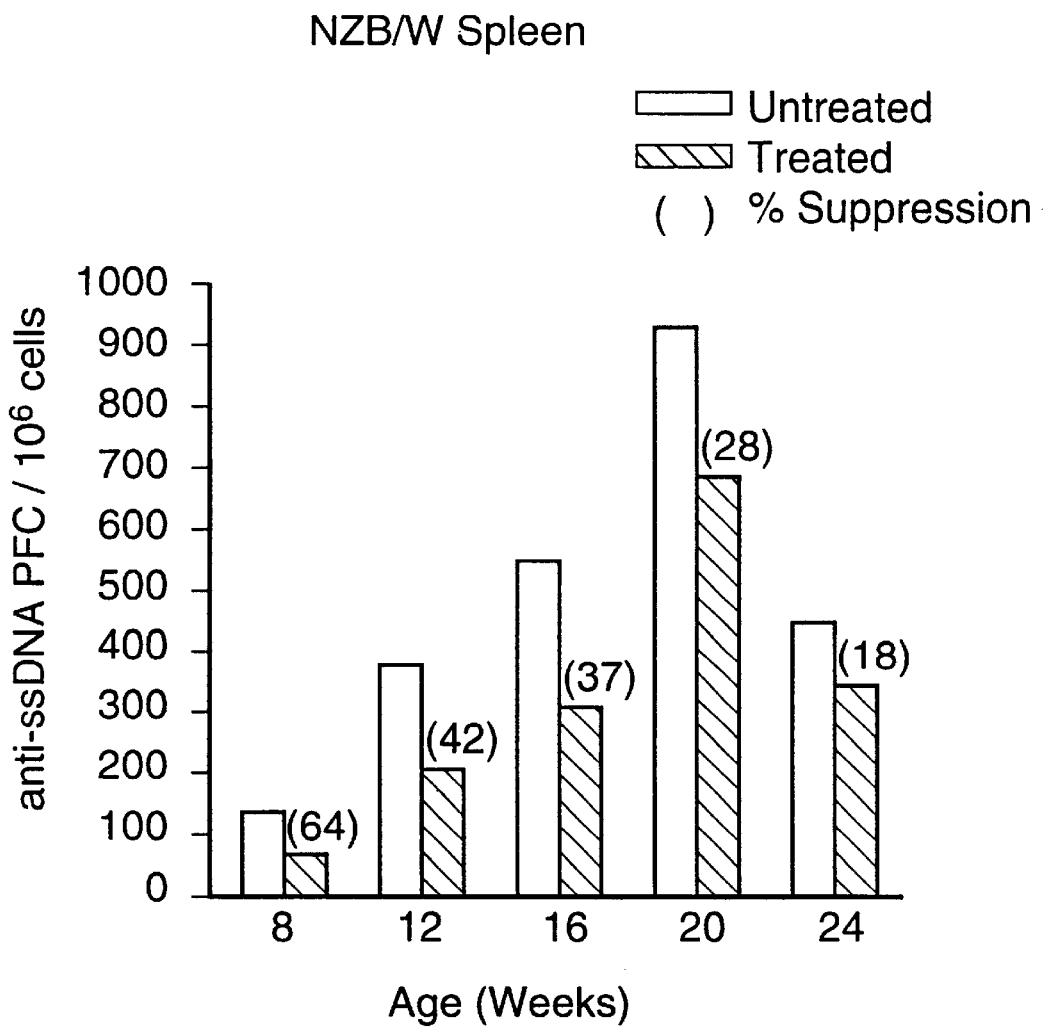
FIG. 37 shows anti-ssDNA production of spleen cells from Reptimed treated (hatched bars) and control (open bars) NZB/W mice at various ages, expressed as PFC/$10^6$ cells. At each age, the PFC values shown are the average for three mice in each group.

Spleens removed from Reptimed treated and control NZB/W mice at four week intervals were treated as described above and anti-ssDNA antibody production was assessed as PFC/10⁶ cells. As shown in FIG. 37, Net anti-ssDNA PFC were determined by subtracting the background PFC response against SRBC from the response against DNA—coupled SRBC.

Kidney Histology of Treated and Untreated Mice

Table 2 summarizes the histological grading of kidney sections from individual mice treated with and without Reptimed. There was definite retardation in the progression of renal lesions in Reptimed treated NZB/W mice.

Figure 38:
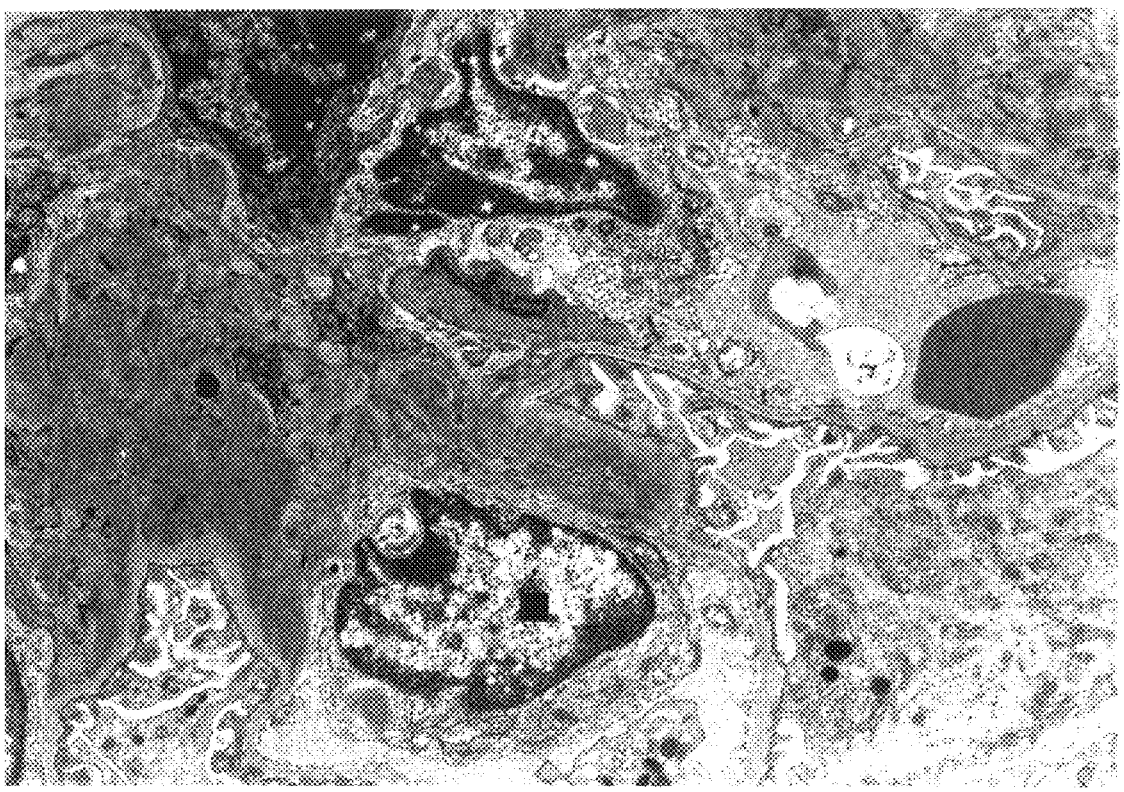
FIG. 38 shows an electron micrograph of a control NZB/W mouse kidney at 24 weeks. EM magnification×126, 000. WHO Class III: Abundant dense deposits in mesangium (●), swollen endothelial cells (■).
Figure 39:
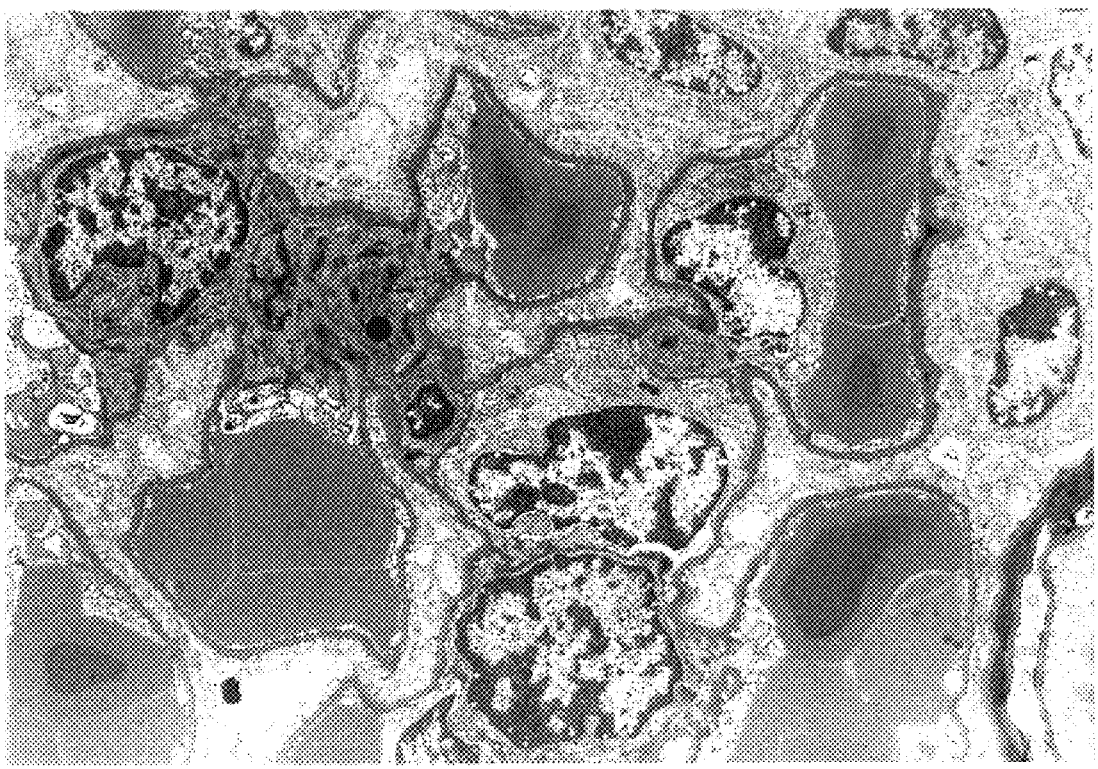
FIG. 39 shows an electron micrograph of a Reptimed treated NZB/W mouse kidney at 24 weeks. EM magnification×27,000. Very early dense deposits in mesangium (●).

FIGS. 38 and 39 are electronmicrographs of kidney biopsies from PBS injected control or Reptimed treated NZB/W mice. At 8 weeks, all animals were graded in Class I (normal by light microscopy, and no significant change in the mesangium). At 12 and 16 weeks, treated mice were still Class I, while non-treated ones were Class IIA (no significant change by light microscope and dense deposits in the mesangium), or IIB (abundant dense deposits and hypercellularity, most of the lesions confined to the mesangium). At 20 and 24 weeks, 2 mice in the treated group had progressed to Class IIA or IIB, one to Class III (more mesangial involvement plus endothelial cell damage with platelets and fibrin occluding the capillary loops, small subendothelial deposits). In the non-treated group, one mouse was IIA at 20 weeks and IIB at 24 weeks, and the other two were Class III or IV (lobular glomeruli with fibrosis, hypercellularity, crescents, and abundant deposits, both mesangial and subendothelial in most of the glomeruli). In one case class V epimembranous deposits were found at 24 weeks.

EXAMPLE 19

Suppression of anti-CD3 Mab-stimulated Proliferation of Human T Cells

Human peripheral T cells were isolated using Ficoll-paque density centrifugation and nylon wool separation procedures. The cells were resuspended in complete medium and cultured at 1×10⁶ cells/ml in 96 well flat-bottom plates. Cells were treated with αCD3 MAb at 1.0 µg/ml, either alone or with the further addition of 5×rat Reptimed, cyclosporin (10 µg/ml), or rapamycin (10 µg/ml).

The cells were cultured for 3 days including a 6 hr. pulse with ³H-thymidine (0.5 µCi/well). Proliferation was determined as described in Example 12.

Figure 40:
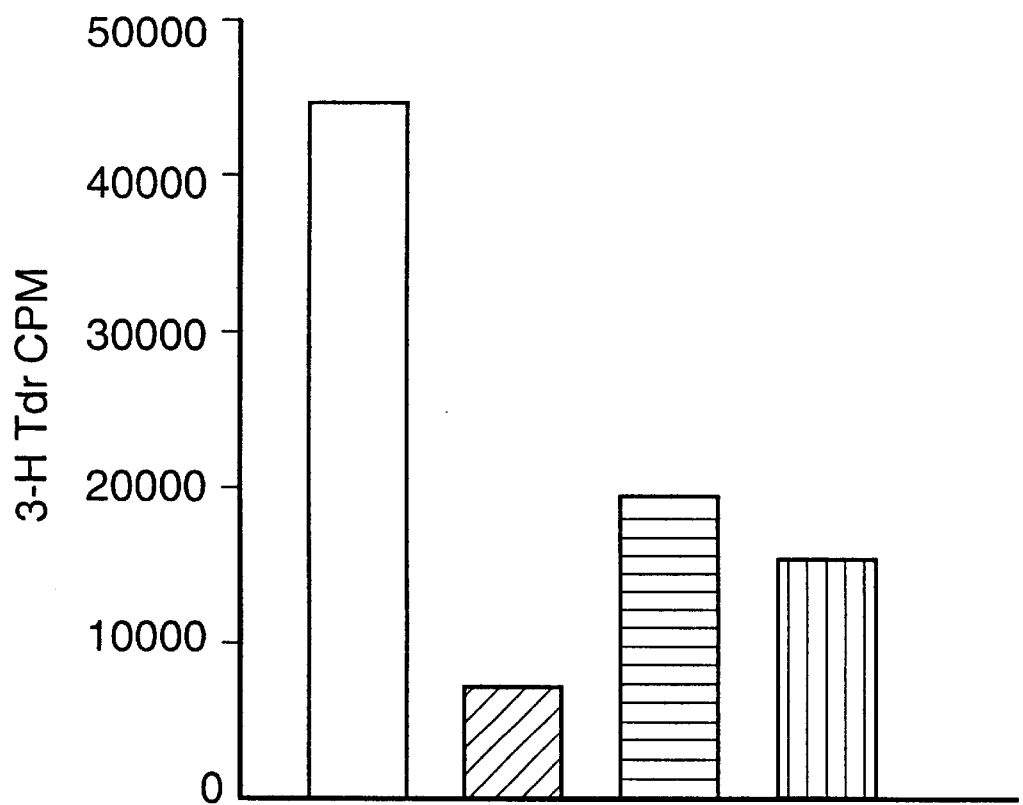
FIG. 40 shows T cell proliferation, expressed as $^3$H thymidine uptake in CPM, in response to 1.0 μg/ml αCD3 MAb alone (open bar) or with the addition of 5×Rat Reptimed (diagonal hatching), cyclosporin 10 μglml (horizontal hatching) or rapamycin 10 μg/ml (vertical hatching).

The results are shown in FIG. 40 and indicate that Reptimed is as good an inhibitor of T cell proliferation as cyclosporin and rapamycin.

Although preferred embodiments of the invention have been described herein in detail, it will be understood by those skilled in the art that variations may be made thereto without departing from the spirit of the invention or the scope of the appended claims.

TABLE 1

Quantitation of Tumour Sizes by MRI
Following Reptimed Treatment
Tumour Areas¹ (mm²) at Days Post Tumour Implant:

| Animal #: | 14 | 18 | 24 | 28 |
|---|---|---|---|---|
| #1 (control TB1)² | 64.6 | 133.0 | D.⁴ | |
| #2 (control TB2) | 105.6 | 206.1 | 293.8 | D. |
| #3 (control TB3) | 64.3 | 230.6 | 315.6 | D. |
| #4 (control TB4) 203.5 | 89.0 | 113.0 | 124.7 | |
| Av. of Controls 203.5 | 80.9 | 170.7 | 244.0 | |
| ± S.E. | ± 10.0 | ± 28.2 | ± 52.3 | |

TABLE 1-continued

Quantitation of Tumour Sizes by MRI
Following Reptimed Treatment
Tumour Areas¹ (mm²) at Days Post Tumour Implant:

| Animal #: | 14 | 18 | 24 | 28 |
|---|---|---|---|---|
| #5 (exp. Reptimed1)³ 8.3 | 122.9 | 34.4 | 36.1 | |
| #6 (exp. Reptimed2) 154.6 | 34.8 | 48.1 | 92.9 | |
| #7 (exp. Reptimed3) 189.3 | 64.6 | 58.2 | 117.8 | |
| #8 (exp. Reptimed4) N.D.T.⁵ | 30.4 | 47.5 | 0.96 | |
| #9 (exp. Reptimed5) 14.3 | N.D.T. | 54.5 | 40.2 | |
| #10 (exp. Reptimed6) 6.4 | N.D.T. | 55.5 | 3.3 | |
| #11 (exp. Reptimed7) 21.6 | N.D.T. | 45.2 | 38.2 | |
| Av. of Reptimed-treated 65.8** | 63.1 | 49.0** | 47.0*** | |
| ± S.E. 41.5 | ± 21.3 | ± 8.0 | ± 21.7 | T± |

¹Measurement of surface area was performed using a PC-base image processing ("Image-Pro Plus") program on intralumenal regions of tumours delineated from the surrounding normal bladder tissue and the urine occupying the bladder lumen.
²TB = control untreated tumour-bearing mice instilled intravesically with 0.1 ml saline × 1 at the time of tumour cell implantation (day 0) and intraperitoneally/intravesically with 0.1 ml saline × 3 at days 0, 3, and 5 post tumour implant.
³exp. Reptimed = Reptimed-treated mice instilled intravesically with 0.1 ml Reptimed (1:100) × 1 at the time of tumour cell implantation (day 0) and intraperitoneally/intravesically with 0.1 ml Reptimed (1:100) × 3 at days 0, 3 and 5 post tumour implant.
⁴D. = Died of overwhelming tumour burden.
⁵N.D.T. = Not detectable tumour.
p < 0.005, and p < 0.0001 by Student's t-test for Reptimed-treated compared to control untreated tumours imaged at the same time points.

TABLE 2

Effects of treatment with Reptimed on renal
pathology in individual NZB/W mice.
WHO Renal pathology classification age in weeks

| | 8 | 12 | 16 | 20 | 24 |
|---|---|---|---|---|---|
| Control | I | IIA | IIA | IIA | IIB |
| (Sham treated) | I | IIA | IIB | III | V |
| NZB/W | I | IIB | IIB | III | IV |
| Reptimed treated | I | I | I | IIA | IIA |
| NZB/W | I | I | I | IIB | IIB |
| | I | I | I | III | III |

TABLE 3

Purification Table of Reptimed

| Step | Volume (ml) | Purification Factor | % Recovered of Activity | % Enrichment of Biological Activity |
|---|---|---|---|---|
| Supernatant | 6000 | — | | |
| C18 Extraction | 30 | — | | |
| P2 Gel Filtration | 3.0 | 33 | 75 | 25 |
| Fast-Q Ion Exchange | 3.0 | 3.9 | 36 | 1.4 |
| Amino-HPLC | 0.5 | 4.9 | 8.9 | 0.4 |
| C8-HPLC | 0.5 | 219 | 30 | 65.7 |
| TOTALS | | 138108 | | 920 |

References

1. Sporn, M. B., A. B. Roberts, L. M. Wakefield and R. K. Assoian. *Science* 233:532, 1986.
2. Ahuja, S. S., F. Paliogianni, H. Yamada, J. E. Balow and D. T. Boumpas. *J.Immunol.* 150:3109, 1993.
3. Hilton, D. J. *Trends.Biochem.Sci.* 17:72, 1992.
4. Oppenheim, J. J., C. O. C. Zachariae, N. Mukaida and K. Matsushima. *Ann.Rev.Immunol.* 9:617, 1991.
5. Broxmeyer, H. E., B. Sherry, S. Cooper, L. Lu, R. Maze, M. P. Beckmann, A. Cerami and P. Ralph. *J.Immunol.* 150:3448, 1993.
6. Lenfant, M., J. Wdzieczak-Bakala, E. Guittet, J-C. Prome, D. Sotty and E. Frindel. *Proc.Natl.Acad.Sci.USA* 86:779, 1989.
7. Paukovits, W. R. and O. D. Laerum. *Z.Naturforsch* 37c:1297, 1982.
8. Pelus, L. M. and H. R. Strausser. *Life Sci* 20:903, 1977.
9. Rola-Pleszczynski, M. *Immunol.Today* 6:302, 1985.
10. Marcus, D. M. *Mol Immunol* 21:1083, 1984.
11. Mortari, F., M. A. Bains and S. K. Singhal. *J.Immunol.* 141:1133, 1988.
12. Keller, J. R., C. Mantel, G. K. Sing, L. R. Ellingsworth, S. K. Ruscetti and F. W. Ruscetti. *J.Exp.Med.* 168:737, 1988.
13. Williams, R. L., D. J. Hilton, S. Pease, T. A. Willson, C. L. Stewart, D. P. Gearing, E. F. Wagner, D. Metcalf, N. A. Nicola and N. M. Gough. *Nature* 336:684, 1988.
14. Verfaillie, C.M., P.M. Catanzarro and W-N. Li. *J.Exp.Med.* 179:643, 1994.
15. Bogden, A. E., P. Carde, E. Deschamps de Paillette, J-P. Moreau, M. Tubiana and E. Frindel. *Ann.NY.Acad.Sci.* 126, 1991.
16. Paukovits, W. R., M-H. Moser and J. B. Paukovits. *Blood* 81:1755, 1993.
17. Laerum, O. D., A. Aakvaag, S. Frostad, T. Kalland, P. Langen and H. R. Maurer. *Int.J.Cell Cloning* 8:431, 1990.
18. Paukovits, W. R., M. Guigon, K. A. Binder, A. Hergl, O. D. Laerum and R. Schulte-Hermann. *Cancer Res* 50:328, 1990.
19. Kaucic, K., A. Grovas, R. Li, R. Quinones and S. Ladisch. *Exp.Hematol.* 22:52, 1994.
20. Hansen, M. B., S. E. Nielsen and K. Berg. *J Immunol Met* 119:203, 1989.
21. Ymer, S., W. Q. J. Tucker, C. J. Sanderson, A. J. Hapel, H. D. Campbell and I. G. Young. *Nature* 317:255, 1985.
22. Stanley, E. R. and L. J. Guilbert. *J Immunol Met* 42:253, 1981.
23. Weinshenker, B. G., Bass, B. Karlik, S., Ebers, G. C. and Rice, G. P. A., *Neurology,* 41:1047, (1991).
24. Nestel, F. P. Price, K. S., Seemayer, T. A., and Lapp, W. S., *J. Exp. Med.* 175:405, 1992.
25. Glassey et al., *Biotechnology and BioEngineering,* 32:1055, 1988.

What is claimed is:

1. A purified, water soluble, non-peptide, negatively charged factor characterised by a molecular weight of about 625 daltons and movement as a single peak on reverse phase high performance liquid chromatography and having the following biological activities:
    (a) prevention or reduction of IL-2 production by activated T lymphocytes;
    (b) prevention or reduction of TNF-alpha production by activated macrophages;
    (c) prevention or reduction of proliferation of activated T lymphocytes; and
    (d) inhibition of mixed lymphocyte reaction.
2. The factor of claim 1 having the further biological activity of inhibition of tumor growth in a mammal.
3. The factor of claim 2 having the further biological activity of inhibition of leukemia cell proliferation.
4. The factor of claim 3 having the further biological activity of inhibition of a graft versus host reaction in a mammal.
5. The factor of claim 1 wherein the factor is derived from mammalian bone marrow cells.
6. The factor of claim 5 wherein the bone marrow cells are myeloid progenitor cells.
7. A pharmaceutical composition comprising an effective amount of the factor of claim 1 and a pharmaceutically acceptable carrier.

* * * * *